(12) United States Patent
Kim et al.

(10) Patent No.: US 11,280,716 B2
(45) Date of Patent: Mar. 22, 2022

(54) OPTICAL DETECTING SYSTEM

(71) Applicant: THE WAVE TALK, INC., Daejeon (KR)

(72) Inventors: Young Dug Kim, Gyeonggi-do (KR); Seung Bum Yang, Daejeon (KR); Kyoung Man Cho, Seoul (KR); Dong Jun Jeong, Daejeon (KR); Nam Kyun Kim, Gyeonggi-do (KR)

(73) Assignee: THE WAVE TALK, INC., Daejeon (KR)

(*) Notice: Subject to any disclaimer, the term of this patent is extended or adjusted under 35 U.S.C. 154(b) by 0 days.

(21) Appl. No.: 17/109,804

(22) Filed: Dec. 2, 2020

(65) Prior Publication Data
US 2021/0102883 A1    Apr. 8, 2021

Related U.S. Application Data

(63) Continuation of application No. 16/492,577, filed as application No. PCT/KR2019/005944 on May 17, 2019, now Pat. No. 11,156,541.

(30) Foreign Application Priority Data

May 18, 2018  (KR) .................. 10-2018-0057326
Jul. 3, 2018    (KR) .................. 10-2018-0077193
(Continued)

(51) Int. Cl.
*G01N 15/06*     (2006.01)
*G01N 33/18*     (2006.01)
(Continued)

(52) U.S. Cl.
CPC ............. *G01N 15/06* (2013.01); *B01D 47/00* (2013.01); *G01N 33/1826* (2013.01);
(Continued)

(58) Field of Classification Search
CPC ............... G01N 15/06; G01N 33/1826; G01N 2015/0693; G02B 27/48; B01D 47/00; B01D 47/02; B01D 2252/103
See application file for complete search history.

(56) References Cited

U.S. PATENT DOCUMENTS 5,904,752 A  *  5/1999  Willeke ................. B01D 45/10
                                                          95/216
6,540,381 B1     4/2003  Douglass, II
(Continued)

FOREIGN PATENT DOCUMENTS

DE  102014108630 A1   12/2015
JP  2000235004 A       8/2000
(Continued)

OTHER PUBLICATIONS

International Application No. PCT/KR2019/005944, International Search Report and Written Opinion, dated Sep. 10, 2019.
(Continued)

*Primary Examiner* — Maurice C Smith
(74) *Attorney, Agent, or Firm* — Marshall, Gerstein & Borun LLP

(57) ABSTRACT

According to an embodiment of the present disclosure, provided is an optical detection system for detecting a laser speckle generated by multiple scattering of a wave irradiated toward a sample from a wave source, and based on a change in the laser speckle over time, detecting the presence of microbes in the sample in real time.

9 Claims, 33 Drawing Sheets

(30) Foreign Application Priority Data

May 17, 2019 (KR) ........................ 10-2019-0057746
May 17, 2019 (KR) ........................ 10-2019-0057747

(51) Int. Cl.
    *B01D 47/00*     (2006.01)
    *G02B 27/48*     (2006.01)
    *B01D 47/02*     (2006.01)

(52) U.S. Cl.
    CPC .............. *G02B 27/48* (2013.01); *B01D 47/02* (2013.01); *B01D 2252/103* (2013.01); *G01N 2015/0693* (2013.01)

(56) References Cited

U.S. PATENT DOCUMENTS

| | | |
|---|---|---|
| 10,001,467 B2 | 6/2018 | Park et al. |
| 10,345,216 B2 | 7/2019 | Clayton et al. |
| 2004/0031322 A1 | 2/2004 | Greenwood |
| 2004/0070756 A1* | 4/2004 | Rastopov ............ G01N 15/0211 356/338 |
| 2004/0083790 A1* | 5/2004 | Carlson ................... B03C 3/49 73/28.02 |
| 2005/0200848 A1 | 9/2005 | Levine et al. |
| 2005/0225752 A1 | 10/2005 | Takai et al. |
| 2007/0206193 A1 | 9/2007 | Pesach |
| 2009/0139399 A1* | 6/2009 | Kang .................... B01D 53/18 95/24 |
| 2009/0244922 A1 | 10/2009 | Hayakawa et al. |
| 2010/0186524 A1* | 7/2010 | Ariessohn ............ G01N 1/2202 73/863.22 |
| 2011/0067994 A1* | 3/2011 | Moorhead .......... B01D 53/1487 203/42 |
| 2011/0242837 A1 | 10/2011 | Cornelissen et al. |
| 2014/0043856 A1 | 2/2014 | Thompson et al. |
| 2015/0276571 A1 | 10/2015 | Hajjarian et al. |
| 2016/0032233 A1* | 2/2016 | Chen ...................... C12M 29/24 435/252.1 |
| 2017/0240949 A1 | 8/2017 | Brutinel et al. |
| 2018/0010426 A1 | 1/2018 | Randle |
| 2019/0154550 A1* | 5/2019 | Wu ........................... G01N 1/22 |
| 2019/0212276 A1 | 7/2019 | Kim et al. |
| 2019/0275183 A1* | 9/2019 | Kamiko .................... A61L 2/10 |

FOREIGN PATENT DOCUMENTS

| | | |
|---|---|---|
| JP | 2017-525366 A | 9/2017 |
| KR | 2004-0094817 A | 11/2004 |
| KR | 20070001177 A | 1/2007 |
| KR | 2008-0057507 A | 6/2008 |
| KR | 20110059006 A | 6/2011 |
| KR | 2016-0013646 A | 2/2016 |
| KR | 2016-0120269 A | 10/2016 |
| KR | 10-2017-0058251 A | 5/2017 |
| KR | 20170046706 A | 5/2017 |
| KR | 20170136989 A | 12/2017 |
| KR | 10-2018-0055301 A | 5/2018 |
| KR | 101939779 B1 | 1/2019 |
| WO | WO-2004/051240 A1 | 6/2004 |
| WO | WO-2015/063481 A2 | 5/2015 |
| WO | WO-2016/028996 A1 | 2/2016 |

OTHER PUBLICATIONS

Office Action, Korean Patent Application No. 10-2018-0057326, dated Oct. 25, 2019.
Bazylev et al., Laser digital speckle anemometry of flows in microchannels of PEM fuel cells, Journal of Engineering Physics and Thermophysics, 79:1230-43 (2006).
European Patent Application No. 19804589, Extended European Search Report, dated Jul. 5, 2021.

\* cited by examiner

FIG. 25

|  | Prediction → | | | | | | | | | | | | |
|---|---|---|---|---|---|---|---|---|---|---|---|---|---|
| PBS | 132 | 0 | 0 | 0 | 0 | 0 | 0 | 0 | 0 | 0 | 0 | 0 | 0 |
| B. subtilis ×10³ | 0 | 132 | 0 | 0 | 0 | 0 | 0 | 0 | 0 | 0 | 0 | 0 | 0 |
| ×10⁵ | 0 | 0 | 132 | 0 | 0 | 0 | 0 | 0 | 0 | 0 | 0 | 0 | 0 |
| ×10⁷ | 0 | 0 | 0 | 132 | 0 | 0 | 0 | 0 | 0 | 0 | 0 | 0 | 0 |
| E. coli | 0 | 0 | 0 | 0 | 132 | 0 | 0 | 0 | 0 | 0 | 0 | 0 | 0 |
|  | 0 | 0 | 0 | 0 | 0 | 132 | 0 | 0 | 0 | 0 | 0 | 0 | 0 |
|  | 0 | 0 | 0 | 0 | 0 | 0 | 132 | 0 | 0 | 0 | 0 | 0 | 0 |
| P. aeruginosa | 2 | 0 | 0 | 0 | 0 | 0 | 0 | 130 | 0 | 0 | 0 | 0 | 0 |
|  | 1 | 0 | 0 | 0 | 0 | 0 | 0 | 0 | 131 | 0 | 0 | 0 | 0 |
|  | 0 | 0 | 0 | 0 | 0 | 0 | 0 | 0 | 0 | 132 | 0 | 0 | 0 |
| S. aureus | 6 | 0 | 0 | 0 | 2 | 0 | 0 | 0 | 0 | 0 | 124 | 0 | 0 |
|  | 0 | 0 | 0 | 0 | 0 | 3 | 0 | 0 | 0 | 0 | 0 | 129 | 0 |
|  | 0 | 0 | 0 | 0 | 0 | 0 | 0 | 0 | 0 | 0 | 0 | 0 | 132 |

Ground truth ↓

OPTICAL DETECTING SYSTEM

CROSS-REFERENCE TO RELATED APPLICATION

The present application is a continuation of U.S. patent application Ser. No. 16/492,577, filed Sep. 9, 2019, which claims priority to U.S. National Stage of International Patent Application No. PCT/KR2019/005944 filed May 17, 2019, which claims the benefit of priority of Korean Patent Application No. 10-2019-0057747 filed May 17, 2019, Korean Patent Application No. 10-2019-0057746 filed May 17, 2019, Korean Patent Application No. 10-2018-0077193 filed on Jul. 3, 2018, and Korean Patent Application No. 10-2018-0057326 filed on May 18, 2018, the respective disclosures of which are each incorporated herein by reference in their entireties.

TECHNICAL FIELD

The present disclosure relates to an optical detection system for detecting microbes or impurities.

BACKGROUND ART

Human beings coexist with other lifeforms. Invisible lifeforms, as well as visible lifeforms, coexist with human beings, and directly/indirectly affect human lives. Among them, microbes or fine lifeforms affecting health states of human beings are not visible to human eyes, but exist around human beings and trigger various illnesses.

In order to measure invisible microbes, a microbe culture method, a mass spectrometry method, a nuclear magnetic resonance method, etc. is used according to the related art. When the microbe culture method, the mass spectrometry method, and the nuclear magnetic resonance method are used, it takes a long time to culture bacteria and precise and complicated equipment that is very expensive is necessary.

Alternately, a method of measuring microbes by using an optical method may be used. For example, a Raman spectrometry or a multispectral imaging method may be used as the optical method, but a complicated optical system is necessary, professional knowledge about the complicated optical system and laboratory level equipment are also necessary, and measurement takes a long time. Thus, it may be difficult for the general public to access the system.

DESCRIPTION OF EMBODIMENTS

Technical Problem

Provided is an optical detection system capable of detecting microbes or impurities in real time by using a chaotic wave sensor.

Solution to Problem

According to an aspect of the present disclosure, an impurity detection system includes: a pipe unit comprising a body portion formed with an inner space penetrating through a first cross section and a second cross section such that a fluid introduced through the first cross section is discharged through the second cross section and a multiple scattering amplification region configured to amplify the number of times a first wave incident between the first cross section and the second cross section in a fluid located in the inner space is multiply scattered; a wave source configured to irradiate the first wave toward the fluid of the pipe unit; a detector arranged outside the pipe unit and configured to detect a laser speckle generated by multiple scattering of the irradiated first wave in the fluid for each preset first time and a controller configured to obtain a temporal correlation of the detected laser speckle using the detected laser speckle and estimate the presence of impurities in the fluid in real time based on the obtained temporal correlation, wherein one or more emission holes configured to guide a second wave emitted by being multiply scattered in the fluid to the detector are formed in the body portion of the pipe unit.

Advantageous Effects of Disclosure

The optical detection system according to embodiments of the present disclosure may use a variation in a temporal correlation of a laser speckle, thereby estimating existence of impurities or concentration of impurities in a sample rapidly at low cost.

BRIEF DESCRIPTION OF DRAWINGS

FIG. 25 is a graph comparing prediction microbe information (prediction) obtained by measuring airborne bacteria through machine learning according to an embodiment of the present disclosure and actual microbe information (ground truth).

BEST MODE

Figure 1:
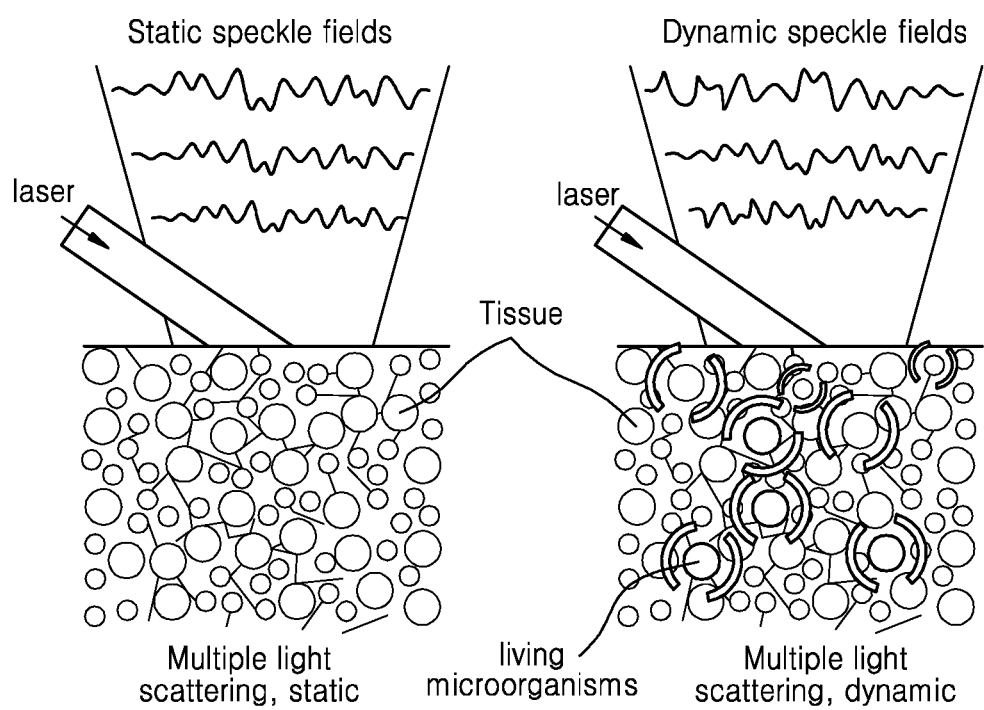
FIG. 1 is a diagram illustrating principles of a chaotic wave sensor according to an embodiment of the present disclosure.

According to an aspect of the present disclosure, a pipe unit includes: a body portion comprising a first cross section, a second cross section facing the first cross section, and an inner surface penetrating the first cross section and the second cross section to form an inner space, wherein the inner surface of the body portion comprises a multiple scattering amplification region in which a pattern for amplifying the number of times a first wave incident between the first cross section and the second cross section in a fluid located in the inner space is multiply scattered is formed, and wherein the pattern is formed by arranging a plurality of grooves having a preset depth d from the inner surface at a preset interval Λ.

The depth d and the interval Λ of the pattern may be determined based on the wavelength λ of the first wave.

The depth d of the pattern may be determined to satisfy an equation below, wherein n is a refractive index of the fluid.

$$\frac{\lambda}{2*n} \le d$$

The interval Λ of the pattern may be determined to satisfy an equation below, wherein θ denotes a scattering angle of the first wave scattered by the pattern.

$$\frac{1}{\Lambda} = \frac{\sin\theta}{\lambda}$$

The body portion may include one or more emission holes configured to guide a second wave emitted by being multiple scattered in the fluid to a detector for detecting.

When two or more emission holes are formed, the two or more emission holes may be disposed at different positions of the body portion.

According to another aspect of the present disclosure, an impurity detection system includes: a pipe unit comprising a body portion formed with an inner space penetrating through a first cross section and a second cross section such that a fluid introduced through the first cross section is discharged through the second cross section and a multiple scattering amplification region configured to amplify the number of times a first wave incident between the first cross section and the second cross section in a fluid located in the inner space is multiply scattered; a wave source configured to irradiate the first wave toward the fluid of the pipe unit; a detector disposed outside the pipe unit and configured to detect a laser speckle generated by multiple scattering the irradiated first wave in the fluid for each preset first time and a controller configured to obtain a temporal correlation of the detected laser speckle using the detected laser speckle and estimate the presence of impurities in the fluid in real time based on the obtained temporal correlation, wherein one or more emission holes configured to guide a second wave emitted by being multiple scattered in the fluid to the detector are formed in the body portion of the pipe unit.

The body portion may include an inner surface surrounding the inner space, the multiple scattering amplification region may be provided in the inner surface of the body portion and formed with a pattern for amplifying the number of times the first wave is multiply scattered, and the pattern may be formed by arranging a plurality of grooves having a preset depth d from the inner surface at a preset interval Λ.

The depth d and the interval Λ of the pattern may be determined based on the wavelength λ of the first wave.

The depth d of the pattern may be determined to satisfy an equation below, $$\frac{\lambda}{2*n} \le d$$

wherein n is a refractive index of the fluid.

The interval Λ of the pattern may be determined to satisfy an equation below, $$\frac{1}{\Lambda} = \frac{\sin\theta}{\lambda}$$

wherein θ denotes a scattering angle of the first wave scattered by the pattern.

The second wave emitted from the one or more emission holes may have a power range of 1 mW/cm² or more in order for the detector to detect the laser speckle at a preset measurement speed or more.

The measurement speed of the detector may be set such that a time for the fluid to pass through the one or more emission holes is greater than a time between first times.

When two or more emission holes are formed, the two or more emission holes may be disposed at different positions along a circumferential direction of the body portion, and the detector may be provided to correspond to the number of the two or more emission holes.

The first wave may have a wavelength range of 200 nm to 1.8 μm. According to an aspect of the present disclosure, a microbial population counting method includes providing a sample placement unit including a plurality of split cells each including a culture material, distributing samples to be measured to the plurality of split cells, irradiating waves sequentially to the plurality of split cells, sequentially detecting individual wave information emitted from samples includes in each split cell in association with the sequentially irradiated waves, determining the presence of microbe in each split cell using the individual wave information, and calculating a microbial population in the sample using the number of split cells in which the microbe is present.

The individual wave information may be information obtained by detecting a laser speckle generated by multiple scattered from the sample accommodated in each of the plurality of split cells for each preset time.

The determining of the presence of the microbe may include obtaining a temporal correlation of the detected laser speckle using the detected laser speckle and determining the presence of the microbe in the corresponding split cell based on the obtained temporal correlation.

The individual wave information may include first image information of a laser speckle detected at a first time, second image information of a laser speckle detected at a second time, and third image information of a laser speckle detected at a third time among the laser speckle emitted from the corresponding split cell, wherein the first to third times are different times, and the determining of the presence of the microbe may include determining the presence of the microbe by using a difference between the first image information to the third image information.

The plurality of split cells may be arranged in the form of a matrix, and the number thereof may be greater than a predicted microbial population included in the sample.

According to another aspect of the present disclosure, a microbial population counting system includes a sample placement unit including a plurality of split cells each including a culture material, configured to distribute and accommodate samples to be measured to the plurality of split cells, a wave source configured to irradiate waves sequentially to the plurality of split cells, a detector configured to sequentially detect individual wave information emitted from samples includes in each split cell in association with the sequentially irradiated waves, and a controller configured to determine the presence of microbe in each split cell using the individual wave information and calculate a microbial population in the sample using the number of split cells in which the microbe is present.

The individual wave information may be information obtained by detecting a laser speckle generated by multiple scattered from the sample accommodated in each of the plurality of split cells for each preset time.

The controller may obtain a temporal correlation of the detected laser speckle using the detected laser speckle and determine the presence of the microbe in the corresponding split cell based on the obtained temporal correlation.

The individual wave information may include first image information of a laser speckle detected at a first time, second image information of a laser speckle detected at a second time, and third image information of a laser speckle detected at a third time among the laser speckle emitted from the corresponding split cell, wherein the first to third times are different times, and the controller may determine the presence of the microbe by using a difference between the first image information to the third image information.

The plurality of split cells may be arranged in the form of a matrix, and the number thereof may be greater than a predicted microbial population included in the sample.

According to another aspect of the present disclosure, an airborne bacteria measuring device includes a collection unit including a storage tank configured to accommodate a collection liquid therein, an inhalation flow path configured to inhale external air to guide an external air to the collection liquid in one side of the storage tank, and an exhaust flow path configured to discharge the air of the storage tank to the outside in the other side of the storage tank, a wave source configured to irradiate a wave toward the collection liquid of the collection unit, an image sensor configured to time serially measure a wave speckle generated by multiple scattering the wave in the collection liquid, and a controller configured to detect the presence of microbe in the collection liquid according to a change in the measured wave speckle over time.

The controller may obtain a temporal correlation of the wave speckle and detect the presence of the microbe in the collection liquid based on the obtained temporal correlation.

The collection unit may further include a collection liquid discharge pipe configured to discharge the completely detected collection liquid and a collection liquid flow pipe configured to flow a new collection liquid into the storage tank.

The airborne bacteria measuring device may further include a first valve installed in the collection liquid flow pipe and selectively opening and closing the collection liquid flow pipe and a second valve installed in the collection liquid discharge pipe and selectively opening and closing the collection liquid discharge pipe, and the controller may control an operation of the first valve or the second valve by a preset program.

The airborne bacteria measuring device may further include a sterilization unit configured to sterilize the completely detected collection liquid in the storage tank, and the controller may control an operation of the second valve to discharge the collection liquid after a sterilization process of the collection liquid is completed.

The airborne bacteria measuring device may further include a filter unit installed in the inhalation flow path and configured to filter a substance having a predetermined size or more included in the external air introduced into the inhalation flow path.

The collection unit may further include a multiple scattering amplifier configured to reflect at least a part of the wave emitted from the collection liquid to the collection liquid to amplify the number of times of multiple scattering in the collection liquid.

The controller may identify a type or concentration of microbe present in the collection liquid based on a change in the wave speckle over time.

The controller may learn a microbial classification criteria based on the change of the wave speckle over time measured in time series order, and identify the type or concentration of microbe present in the collection liquid using the microbial classification criteria.

According to another aspect of the present disclosure, an optical detection system includes a wave source, an optical unit configured to transferring a wave generated in the wave source to a first path or a second path, a first speckle generation unit disposed on the first path and including a static scattering medium to scatter the first wave incident along the first path and generate a first speckle, a first image sensor configured to detect the first speckle in time series order, a sample accommodation unit disposed on the second path and including a sample to be measured, a second image sensor configured to detect an optical signal generated in the sample in time series order, and a controller configured to obtain a temporal correlation of the first speckle using the detected first speckle and control an operation of the second image sensor based on the obtained temporal correlation of the first speckle.

The sample accommodation unit may include a second speckle generation unit configured to scatter a second wave incident along the second path and generate a second speckle.

The controller may obtain a temporal correlation of the second speckle detected using the detected second speckle, and estimate the presence or concentration of microbe in the sample based on the obtained temporal correlation of the second speckle.

The controller may determine a change in the property of the first wave based on the temporal correlation of the first speckle, and control an operation of the second image sensor according to the change in the property of the first wave.

The controller may calculate a temporal correlation coefficient of the first speckle and operate the second image sensor only when the temporal correlation coefficient of the first speckle corresponds to a preset range.

The controller may calculate the temporal correlation coefficient of the first speckle and use the temporal correlation coefficient of the first speckle to calibrate a detection signal of the second image sensor.

The first speckle generation unit and the second speckle generation unit may be integrally formed.

The second speckle generation unit may further include a multiple scattering amplifier including a multiple scattering material to amplify the number of times of multiple scattering of the second wave in the sample.

According to another aspect of the present disclosure, an optical detection system includes a wave source, an optical unit configured to transferring a wave generated in the wave source to a first path or a second path, a first speckle generation unit disposed on the first path and including a static scattering medium to scatter the first wave incident along the first path and generate a first speckle, a second generation unit disposed on the second path and including a sample to be measured to scatter a second wave incident along the second path and generate a second speckle, a second shutter disposed between the first optical unit and the second speckle generation unit, an image sensor configured to detect the first speckle or the second speckle in time series order, and a controller configured to obtain a temporal correlation of the first speckle using the detected first speckle by the image sensor and control an operation of the second shutter based on the obtained temporal correlation of the first speckle.

The controller may obtain a temporal correlation of the second speckle detected using the detected second speckle, and estimate the presence or concentration of microbe in the sample based on the obtained temporal correlation of the second speckle.

The controller may determine a change in the property of the first wave based on the temporal correlation of the first speckle, and control an operation of the second shutter according to the change in the property of the first wave.

The controller may calculate a temporal correlation coefficient of the first speckle and open the second shutter to detect the second speckle only when the temporal correlation coefficient of the first speckle corresponds to a preset range.

The optical detection system may further include a first shutter disposed between the first optical unit and the first speckle generation unit, and the controller may control the first shutter to be closed while the second shutter is opened.

The second speckle generation unit may further include a multiple scattering amplifier including a multiple scattering material to amplify the number of times of multiple scattering of the second wave in the sample.

According to another aspect of the present disclosure, an optical detection system includes a wave source, an optical unit configured to transferring a wave generated in the wave source to a first path or a second path, a first speckle generation unit disposed on the first path and including a control group sample to scatter the first wave incident along the first path and generate a first speckle, a first image sensor configured to detect the first speckle in time series order, a second generation unit disposed on the second path and including a measurement group sample and a medium to scatter a second wave incident along the second path and generate a second speckle, a second image sensor configured to detect the second speckle in time series order, and a controller configured to estimate a first concentration of the control group sample and a second concentration of the measurement group sample using the detected first speckle and the detected second speckle, and determine the presence of live bacteria in the measurement group sample using the first concentration and the second concentration.

The controller may obtain a temporal correlation of the first speckle detected using the detected first speckle, and then estimate the first concentration of the control group sample using the temporal correlation of the first speckle, obtain a temporal correlation of the second speckle detected using the detected second speckle, and then estimate the second concentration of the measurement group sample using the temporal correlation of the second speckle.

The measurement group sample may be a sample diluted m times the control group sample, and the controller may obtain a growth time at which the second concentration is equal to the first concentration and then derive a ratio of live bacteria and dead bacteria in the measurement group sample using the growth time.

The second speckle generation unit may further include a multiple scattering amplifier including a multiple scattering material to amplify the number of times of multiple scattering of the second wave in the sample.

Other aspects, features and advantages of the present disclosure will become better understood through the accompanying drawings, the claims and the detailed description.

Mode of Disclosure

The exemplary embodiments will be described below in more detail with reference to the accompanying drawings. Those components that are the same or are in correspondence are rendered the same reference numeral regardless of the figure number, and redundant explanations are omitted.

As the present disclosure allows for various changes and numerous embodiments, particular embodiments will be illustrated in the drawings and described in detail in the written description. The attached drawings for illustrating one or more embodiments are referred to in order to gain a sufficient understanding, the merits thereof, and the objectives accomplished by the implementation. However, the embodiments may have different forms and should not be construed as being limited to the descriptions set forth herein.

While such terms as "first," "second," etc., may be used to describe various components, such components must not be limited to the above terms. The above terms are used only to distinguish one component from another.

An expression used in the singular encompasses the expression of the plural, unless it has a clearly different meaning in the context.

In the present specification, it is to be understood that the terms such as "including," "having," and "comprising" are intended to indicate the existence of the features or components disclosed in the specification, and are not intended to preclude the possibility that one or more other features or components may exist or may be added.

It will be understood that when a unit, region, or component is referred to as being "formed on" another layer, region, or component, it can be directly or indirectly formed on the other layer, region, or component. That is, for example, intervening units, regions, or components may be present.

It will be understood that when an element is referred to as being "connected" or "coupled" to another element, it does necessarily not mean direct and/or fixed connection or coupling of to the two elements or intervening elements may be present, unless it has a clearly different meaning in the context.

It will be further understood that the terms "comprises," "comprising," "includes" and/or "including," when used herein, specify the presence of stated features or components, but do not preclude the presence or addition of one or more other features or components.

Sizes of components in the drawings may be exaggerated for convenience of explanation. In other words, since sizes and thicknesses of components in the drawings are arbitrarily illustrated for convenience of explanation, the following embodiments are not limited thereto.

Hereinafter, principles of a chaotic wave sensor according to an embodiment of the present disclosure will be described with reference to FIG. 1.

FIG. 1 is a diagram illustrating principles of a chaotic wave sensor according to an embodiment of the present disclosure.

When light is irradiated to a material having a uniform internal refractive index, e.g., glass, the light is refracted in a constant direction. However, when coherent light such as a laser is irradiated to a material having a non-uniform internal refractive index, multiple scattering that is very complicated occurs in the material.

Referring to FIG. 1, in light or waves (hereinafter, referred to as waves for convenience' sake) irradiated from a wave source 120, some of the waves scatter through complicated paths due to the multiple scattering pass through a test target surface. Waves passing through multiple points in the test target surface generate constructive interference or destructive interference, and the constructive/destructive interference of the waves generates grain patterns (speckles).

In the present specification, the waves scattered in the complicated paths are referred to as "chaotic wave", and the chaotic wave may be detected through laser speckles.

The left side of FIG. 1 shows a state in which a laser is irradiated to a stabilized medium. When interference light (e.g., laser) is irradiated to the stabilized medium, in which internal component material does not move, a stabilized speckle pattern without a variation may be observed.

However, as shown at the right side of FIG. 1, when the medium has a non-stabilized internal component that is moving, such as bacteria, the speckle pattern varies.

That is, fine activity of life, e.g., movement of microbes, may finely change an optical path according to time. Since the speckle pattern is generated due to interference of the waves, a fine change in the optical path may cause variation in the speckle pattern. Accordingly, when a temporal variation in the speckle pattern is measured, the activities of microbes may be rapidly measured. As described above, when the variation in the speckle pattern according to time is measured, existence of the microbes and concentration of the microbes may be identified, and further, kinds of the microbes may be identified.

In the present specification, a structure for measuring the variation in the speckle pattern is defined as a chaotic wave sensor.

In the present specification, embodiments of an optical detection system having various applications such as technology of detecting impurities in a fluid, technology of counting microbial population, airborne bacteria measuring technology and wave correction technology while having a basic idea of detecting microbe or impurities present in a static medium by using the chaotic wave sensor as described above will be described. At this time, the optical detection system may be called a different name for each embodiment, and may be designated with a different name or numeral for the convenience of description even if it includes components that perform the same function. Here, the medium may be applied to any material or state having a static property.

Figure 2:
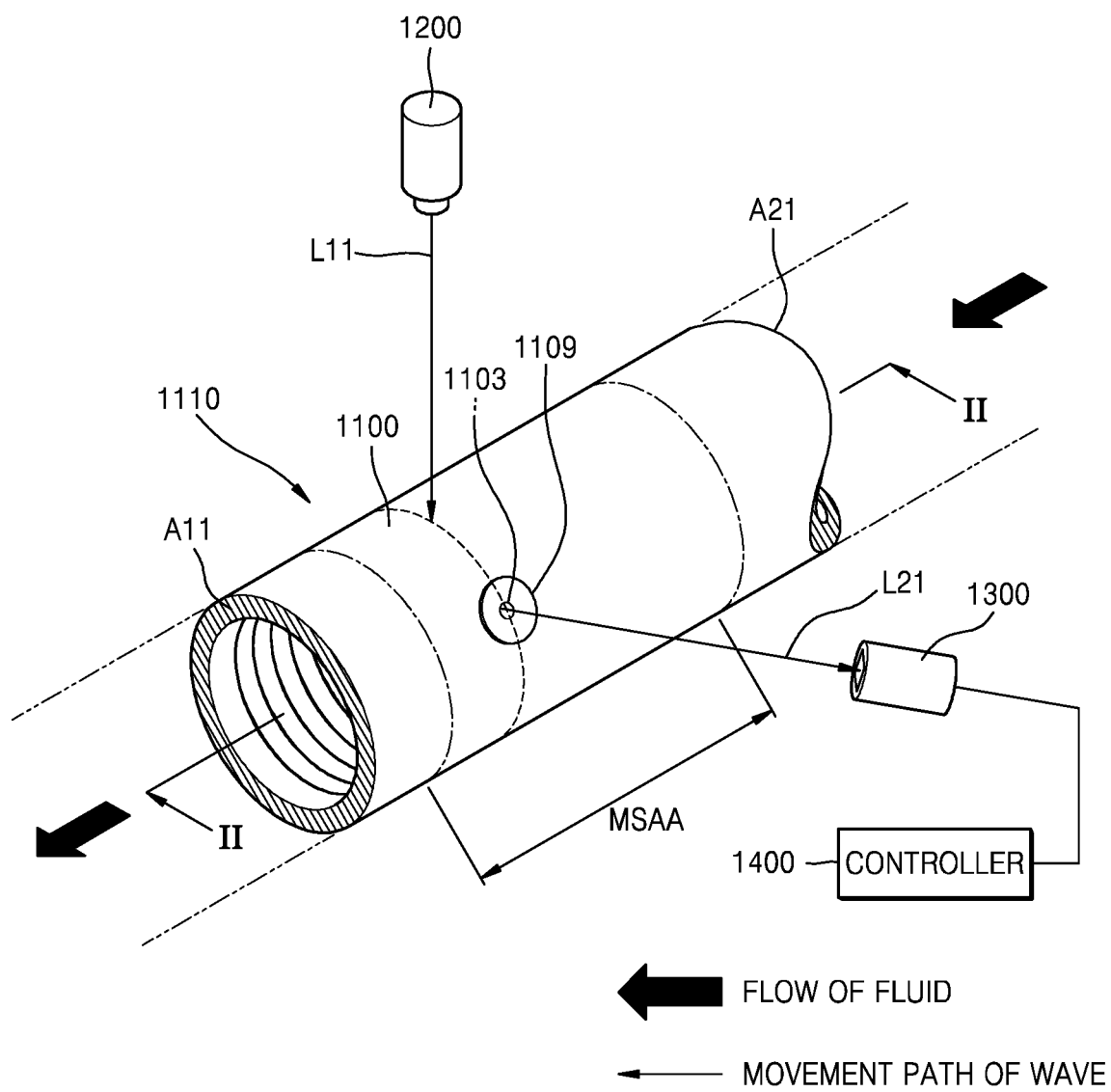
FIG. 2 is a conceptual diagram schematically illustrating an impurity detection system according to an embodiment of the present disclosure.
Figure 3:
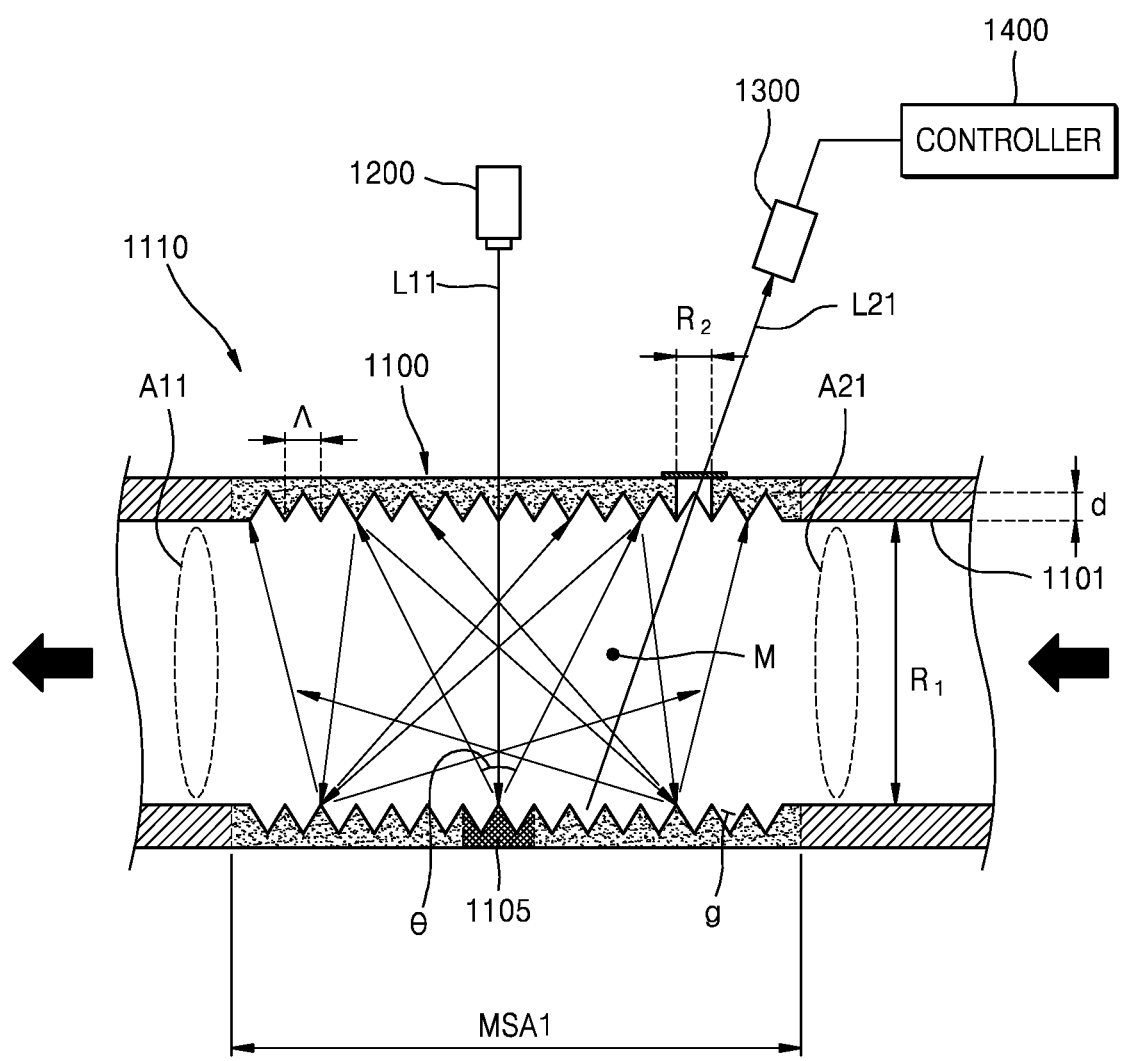
FIG. 3 is a cross-sectional view taken along a line II-II of FIG. 2.
Figure 4:
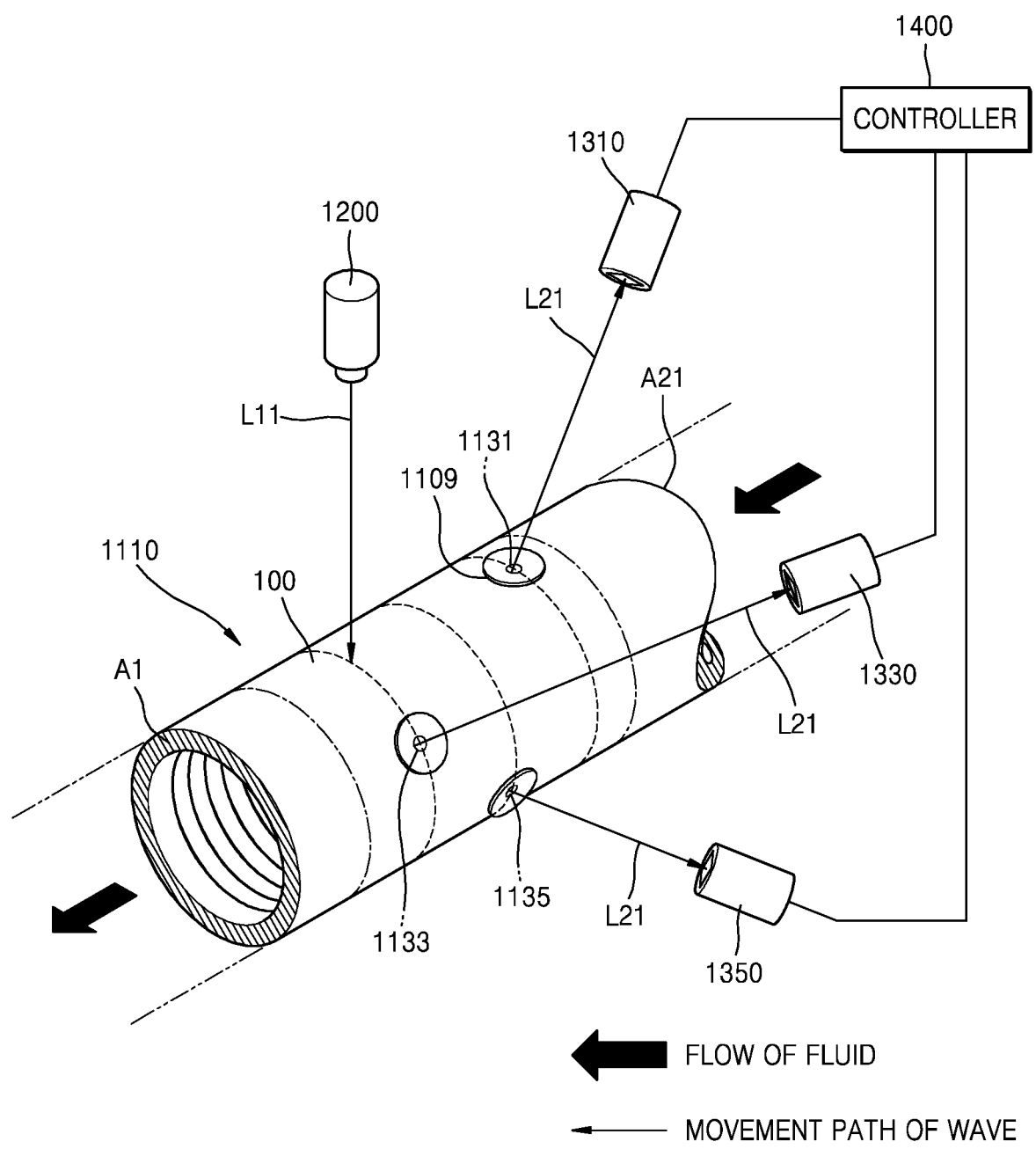
FIG. 4 is a conceptual diagram schematically showing an impurity detection system according to another embodiment of the present disclosure.

FIG. 2 is a conceptual diagram schematically illustrating an impurity detection system 10 according to an embodiment of the present disclosure, and FIG. 3 is a cross-sectional view taken along line II-II of FIG. 2. FIG. 4 is a conceptual diagram schematically showing an impurity detection system 10' according to another embodiment of the present disclosure.

Referring to FIGS. 2 and 3, an impurity detection system 10 in a fluid according to an embodiment of the present disclosure may include a pipe unit 1110, a wave source 1200, a detector 1300, and a controller 1400.

The pipe unit 1110 may include a first cross section A11 and a second cross section A21, and may include a body portion 1100 including an inner surface 1101 penetrating the first cross section A11 and the second cross section A21 to form an inner space. In this case, the first cross section A11 and the second cross section A21 may be disposed to face each other. The body portion 1100 may be formed, for example, in a cylindrical shape, but the present disclosure is not limited thereto.

A fluid may be introduced through the second cross section A21 of the pipe unit 1110 and may be discharged through the first cross section A11 via the inner space. In the present specification, the fluid may be a liquid or a gas, and may have a preset flow rate. The pipe unit 1110 may be disposed at any part of a production line of liquid such as bottled water or beverage, and the fluid may be introduced through the second cross section A21 to penetrate the inner space of the pipe unit 1110 and then may be discharged through the first cross section A11. For example, the flow rate of the fluid may range from 4 m/s to 5 m/s, which is a flow rate of an actual factory environment. However, the present disclosure is not limited thereto, and the flow rate of the fluid may have a flow rate of 1 m/s or less like a water pipe.

As another example, the flow rate of the fluid may be set based on the measurement conditions in the detector 1300. In other words, even if the flow rate of the actual factory environment is 4 m/s to 5 m/s, the impurity detection system 10 may reduce the flow rate of the fluid to a preset rate such that the flow rate of the fluid immediately before the pipe unit 1110 is a rate measurable by the detector 1300.

As used herein, an impurity may be a material of a small size, such as a microbe, that exceeds the visual limit of the human eye. In an embodiment, when the impurity is a microbe, the fluid may be a material to which the microbe may proliferate, for example, water that does not include a scattering material therein. However, the present disclosure is not limited thereto, and in another embodiment, the fluid may be a material such as milk including the scattering material therein. In another embodiment, the fluid may also be air.

Although not shown, the fluid may be introduced into the pipe unit 1110 through a fluid supply unit. The fluid supply unit may include a fluid storage tank and a supply means such as a hydraulic pump or a compressor for providing a flow force to the fluid include in the fluid storage tank. The fluid may pass through the pipe unit 1110 in one direction through the supply means.

In an embodiment, the pipe unit 1110 may introduce the fluid through the entire area of the second cross section A21, and discharge the fluid through the entire area of the first cross section A11. In other words, the fluid may move in a state in which the inside of the pipe unit 1110 is filled up. When the fluid moves in a state where the cross-sectional area of the pipe unit 1110 is not 100% filled, a wavefront may be generated in the fluid due to the flow of the fluid. Such a wavefront may act as a scatterer, and may act as a noise to detect impurities through the detector 1300. Accordingly, in order to minimize such noise, the pipe unit 1110 may discharge the fluid through the entire areas of the first cross section A11 and the second cross section A21.

Meanwhile, the body portion 1100 of the pipe unit 1110 may include a multiple scattering amplification region MSA1 formed on an inner surface 1101. A pattern for amplifying the number of times of multiple scattering of a first wave L11 incident between the first cross section A11 and the second cross section A21 in the fluid located in the inner space of the pipe unit 1110 may be formed in the multiple scattering amplification region MSA1.

The multiple scattering amplification region MSA1 may scatter at least a part of the first wave L11 that is incident into the inner space of the pipe unit 1110 and passes through the fluid and is emitted toward the inner surface 1101 into the fluid again. The first wave L11 scattered as described above may be emitted to the other side of the inner surface 1101 through the fluid and scattered, and through this process, the number of times of multiple scattering in the fluid may increase. In this case, the multiple scattering amplifier region MSA1 may amplify the number of multiple scattering due to patterns formed based on a wavelength A of the incident first wave L11.

The pattern may include a plurality of grooves g formed in a concave shape from the inner surface 1101 toward an outer surface of the pipe unit 1110. The pattern may be formed by arranging the plurality of grooves g having a preset depth d from the inner surface 1101 at a preset interval Λ. Here, the depth d and the interval Λ of the pattern may be determined based on the wavelength λ of the first wave.

Specifically, the depth d of the pattern may be determined to satisfy Equation 1 below, $$\frac{\lambda}{2*n} \leq d \qquad \text{[Equation 1]}$$

wherein n may be a refractive index of the fluid passing through the inner space of the pipe unit 1110. When the depth d of the pattern is smaller than $$\frac{\lambda}{2*n},$$

the first wave L11 incident on the inner surface 1101 has a high reflectance, making it difficult to increase the intended number of times of multiple scattering. The pipe unit 1110 may increase a scattering rate in the inner space by forming the pattern to satisfy Equation 1 above. In addition, the depths d of the pattern including the plurality of grooves g may not need to be the same, and even if they are formed irregularly, if the depth d of each of the grooves g satisfies the above Expression 1, a sufficient scattering rate may be secured. In this case, the depth d of the pattern may not exceed the cross-sectional thickness of the pipe unit 1110.

In addition, the interval Λ of the pattern may be determined to satisfy Equation 2 below, $$\frac{1}{\Lambda} = \frac{\sin\theta}{\lambda} \qquad \text{[Equation 2]}$$

wherein θ may denote a scattering angle of the first wave L11 scattered by the pattern. In addition, the interval Λ of the grooves g may be an interval between peaks of unevennesses formed by the grooves g. The scattering angle θ may be determined according to an area of the multiple scattering amplification region MSA1 and/or power of the first wave L11. When the scattering angle θ is large, the first wave L11 may be scattered over a larger area than that when the scattering angle θ is small, whereas the power of the first wave L11 after scattered may be reduced rather than when the the scattering angle θ is small. Using this relationship, the scattering angle θ may be determined according to the measurement conditions, for example, a diameter R1 of the pipe unit 1110 or the power of the first wave L11 emitted from the wave source 1200.

Meanwhile, the pattern may include the plurality of grooves g arranged in a predetermined direction. In an embodiment, as shown in the drawing, the pattern may be formed by arranging the grooves g extending in a direction perpendicular to a longitudinal direction of the pipe unit 1110 at the interval Λ. In another embodiment, although not shown, the pattern may be formed by arranging the grooves g extending in the longitudinal direction of the pipe unit 1110 at the interval Λ. In another embodiment, the pattern may include first grooves extending and arranged along the longitudinal direction of the pipe unit 1110 and second grooves formed to overlapping the first grooves and extending and arranged in the direction perpendicular to the longitudinal direction of the pipe unit 1110.

In this case, the multiple scattering amplification region MSA1 may be configured in a pattern formed in a lattice form. When the plurality of grooves g extending along the circumferential direction are arranged along the longitudinal direction of the pipe unit 1110, the incident first wave L11 is different depending on an incident angle, but the incident first wave L11 is mostly scattered in the longitudinal direction of the pipe unit 1110. In addition, when the plurality of grooves g extending in the longitudinal direction are arranged along the circumferential direction of the pipe unit 1110, the incident first wave L11 is mostly scattered in the circumferential direction of the pipe unit 1110. In other words, in the case where the first wave L11 is scattered to amplify the number of times of multiple scattering to the cross-section of the pipe unit 1110, the grooves g may be formed to be arranged along the circumferential direction, and in the case where the number of multiple scattering is amplified in the longitudinal direction of the pipe unit 1110, the grooves g may be formed to be arranged along the longitudinal direction. In addition, because the number of times of multiple scattering is amplified in various directions by forming the pattern in grooves crossing in different directions, the cross-section and the longitudinal direction of the pipe unit 1110 may be closely filled with the first wave L11. Through this, the impurity detection system 10 may increase a probability of detecting impurities in the fluid.

Meanwhile, in another embodiment, the multiple scattering amplification region MSA1 may include a multiple scattering material. For example, the multiple scattering material may include particles having a diameter of a micrometer having a large refractive index or less, for example, titanium oxide ($TiO_2$) nanoparticles. In this case, the multiple scattering amplification region MSA1 may be formed by coating the multiple scattering material on an outer surface of a main body of the pipe unit 1110. However, the present disclosure is not limited thereto, and in another embodiment, the multiple scattering amplification region MSA1 may be formed by including the multiple scattering material in the main body of the pipe unit 1110. Alternatively, in the case of an opaque pipe such as a metal pipe, the multiple scattering amplification region MSA1 may be formed by coating a multiple scattering material on an inner surface of the main body of the pipe unit 1110.

In another embodiment, the multiple scattering amplification region MSA1 may include a multiple scattering amplifier (not shown) disposed adjacent to the main body of the pipe unit 1110 to reflect at least a part of wave emitted from the fluid to the outside of the pipe unit 1110 to the inside of the pipe unit 1110. In this case, the multiple scattering amplifier (not shown) may cause the wave emitted from the pipe unit 1110 to reciprocate a space between the pipe unit 1110 and the multiple scattering amplifier (not shown) at least one or more times. Meanwhile, the multiple scattering amplification region MSA1 may be disposed in at least a partial region between the first cross section A11 and the second cross section A21 of the pipe unit 1110, for example, in the entire region.

Meanwhile, at least a part of the multiple scattering amplification region MSA1 may be a reflection region 1105 reflecting the entirety of the first wave L11 emitted from the fluid into the fluid. The reflection region 1105 may increase the impurity detection rate of the detector 1300 by minimizing the emission of the first wave L11 from the fluid to the outside of the pipe unit 1110. The reflection region 1105 may be disposed to face an incident region where the first wave L11 is incident from the wave source 1200. The reflection region 1105 may reflect the entirety of the first wave L11 irradiated from the wave source 1200 into the fluid, thereby increasing an amount of waves capable of being multiple scattered in the fluid, and accordingly amplifying the impurity detection rate in the detector 1300. In another embodiment, the entire region of the multiple scattering amplification region MSA1 except for an emission hole 1103 may be a reflection region.

Meanwhile, the pipe unit 1110 may include one or more emission holes 1103 guiding a second wave emitted by being multiple scattered in the fluid to the detector 1300 for detecting. The detector 1300, which will be described later, may be disposed adjacent to the emission hole 1103 to detect the second wave L21 emitted from the emission hole 1103. The emission hole 1103 may be configured as a hole penetrating the body portion 1100 as shown.

At this time, as shown, the pipe unit 1110 may further include a cover portion 1109 disposed at one side of the emission hole 1103. The cover portion 1109 may include a transparent or translucent material such that the second wave L21 may pass therethrough. For example, the cover portion 1109 may include a glass or plastic material, and may be formed in a plate shape having flexibility, but may also be manufactured in a film. In another embodiment, the cover portion 1109 may be formed to fill the inside of the emission hole 1103 rather than one side of the emission hole 1103.

Meanwhile, although in the drawing exaggerated for convenience of explanation, the emission hole 1103 may have a minimum diameter R2 by which the second wave L21 may be emitted while ensuring the scattering rate in the inner space of the pipe unit 1110 to the maximum.

Meanwhile, referring to FIG. 4, two or more emission holes 1103 may be formed in the body portion 1100 of the pipe unit 1110. When two or more emission holes 1103 are formed, the two or more emission holes 1103 may be disposed at different positions along the circumferential direction of the body portion 1100. Through this structure, the plurality of second waves L21 may be guided to a plurality of detectors 31, 33, and 35 that will be described later.

Hereinafter, the impurity detection system 10 including the pipe unit 1110 described above will be described in more detail.

Because a fluid such as water does not include a homogeneous substance that causes scattering therein as described above, a laser speckle may not be generated when a microbe M, which is an impurity, is not present. However, the system 10 for detecting the microbe M in a fluid according to an embodiment of the present disclosure may multiple scatter the first wave through the multiple scattering amplification region MSA1 of the pipe unit 1110 described above to generate a static laser speckle pattern. The system 10 for detecting the microbe M in the fluid L may change a path of the first wave by a movement of the microbe M when the microbe M is present in the fluid L that moves in the pipe unit 1110. A subtle change in a first wave path may cause a change in the speckle pattern. Accordingly, by measuring a temporal change of the speckle pattern, the presence of the microbe M in the fluid L may be rapidly detected.

Referring to FIGS. 2 and 3 again, the wave source 1200 may irradiate the first wave L11 toward the fluid of the pipe unit 1110. The wave source 1200 may apply all types of source device capable of generating a wave, and may be, for example, a laser capable of irradiating light of a specific wavelength band. Although the present disclosure is not limited to a type of a wave source, a case where the wave source is the laser will be described for convenience of description.

For example, laser with a good coherence may be used as the wave source 1200 to form speckle in the fluid. In this case, the shorter the spectral bandwidth of the wave source that determines the coherence of the laser wave source, the greater the measurement accuracy. That is, the longer the coherence length, the greater the measurement accuracy. Accordingly, a laser light whose spectral bandwidth of the wave source is less than a predetermined reference bandwidth may be used as the wave source 1200, and the measurement accuracy may increase as the spectral bandwidth of the wave source is shorter than the reference bandwidth. For example, the spectral bandwidth of the wave source may be set such that the condition of Equation 3 below is maintained.

$$\text{spectralbandwidth} < 5 \text{ nm} \quad \text{[Equation 3]}$$

According to Equation 3, in order to measure the pattern change of the laser speckle, the spectral bandwidth of the wave source 1200 may be maintained less than 5 nm when light is irradiated into the fluid every reference time.

In an embodiment, the wave source 1200 may be disposed outside the pipe unit 1110 to irradiate the first wave L11 toward the pipe unit 1110 as shown. In this case, an incidence hole (not shown) penetrating the body portion 1100 may be formed in the pipe unit 1110 to transmit the first wave L11 radiated from the wave source 1200 to the fluid. The incidence hole (not shown) may be formed to have the same diameter as the emission hole 1103 described above, and the cover portion 1109 may be disposed like the emission hole 1103. In another embodiment, the wave source 1200 may be disposed in the inner surface of the pipe unit 1110 or may be embedded in the body portion 1100 of the pipe unit 1110 to irradiate the first wave L11 toward the fluid. In the drawing, the wave source 1200 is illustrated as one, but a plurality of wave sources 1200 may be provided as necessary.

Meanwhile, the wave source 1200 may output the first wave L11 having a predetermined first power and the wavelength λ.

Figure 5:
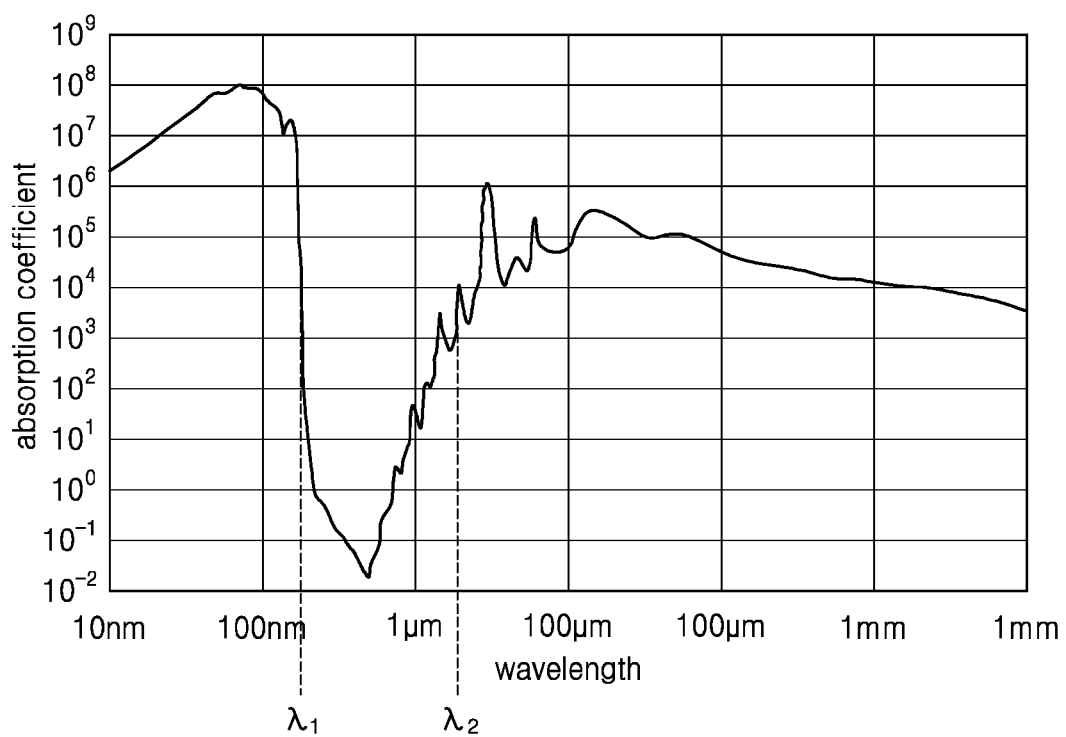
FIG. 5 is an absorbance diagram for each wavelength band when a fluid is water.

FIG. 5 is an absorbance diagram for each wavelength band when a fluid is water.

Referring to FIG. 5, the first wave L11 may have the wavelength λ in the range of a first wavelength λ1 to a second wavelength λ2. The fluid may absorb waves. Absorbance generally means that the energy of photons, such as electrons in an atom, is absorbed by a material, and the energy of such waves may be converted into the internal energy of the fluid, such as thermal energy. As the absorption occurs more, the fluid internal temperature increases, and the power of the first wave L11 decreases as much as the fluid internal temperature increases. If a degree of the power reduction of the first wave L11 is large while passing through the fluid, detection by the detector 1300 may be difficult.

Because the absorption in the fluid is different for each wavelength band as shown in FIG. 5, the first wave L11 may be set to have a wavelength range that may minimize absorption in the fluid. For example, when the fluid is water, the fluid may have an absorption coefficient for each wavelength band as shown in FIG. 5. The impurity detection system 10 according to an embodiment of the present disclosure may use the first wave L11 having a wavelength range in which the absorption coefficient of the fluid is equal to or less than a predetermined value in order to minimize absorption of waves in the fluid. For example, the first wave L11 may have a wavelength range of 200 nm to 1.8 mm such that an absorption coefficient of water has a value less than $1 \times 10^3$ to $1 \times 10^4$.

Referring to FIGS. 2 and 3 again, the detector 1300 may detect a laser speckle generated by multiple scattering the irradiated first wave L11 in the fluid for each preset time. Here, time means any moment in a continuous flow of time, and times may be set in advance at the same time interval, but are not limited thereto, and may be set in advance at any time interval.

The detector 1300 may include a sensing means corresponding to a type of the wave source 1200. For example, when a light source of a visible light wavelength band is used, a CCD camera which is an image capturing device may be used. The detector 1300 may detect a laser speckle at least at a first time, detect a laser speckle at a second time, and provide the detected laser speckles to the controller 1400. Meanwhile, the first point and the second time are merely one example selected for convenience of description, and the detector 1300 may detect laser speckles at a plurality of times more than the first point and the second time.

Specifically, when the first wave L11 is irradiated to the fluid, the incident first wave L11 may form a laser speckle by multiple scattering. Because the laser speckle is generated by the interference of light, if there is no microbe in the fluid, a multiple scattering amplification region may always show a constant interference pattern over time. In comparison, when the microbe M is present in the fluid, the laser speckle may change over time by a movement of the microbe M. The detector 1300 may detect the laser speckle that changes over time for each preset time and provide the laser speckle to the controller 1400. The detector 1300 may detect the laser speckle at a speed sufficient to detect the movement of the microbe M, and for example, may detect the laser speckle at the speed of 25 to 30 frames per second.

The detector 1300 may be disposed adjacent to the emission hole 1103 of the pipe unit 1110, and detect the second wave L21 emitted through the emission hole 1103 after the first wave L11 irradiated from the wave source 1200 is multiply scattered. In this case, the second wave L21 may have a power range of 1 mW/cm² or more such that the detector 1300 may detect the laser speckle at a measurement speed greater than or equal to a preset measurement speed. When the second power of the second wave L21 is smaller than 1 mW/cm², the detector 1300 which measures rapidly may not sufficiently detect the second wave L21. In addition, the detector 1300 should be capable of high speed measurement in order to detect the microbe M which is an impurity from the flowing fluid. Here, high speed measurement means detecting a laser speckle faster than a flow rate of the fluid. For example, the measurement speed of the detector 1300 may be set such that a time T1 at which the fluid passes the emission hole 1103 is greater than a time T2 between the first times for detecting the laser speckle.

$$\frac{T1}{T2} > 1$$

Meanwhile, the first wave L11 irradiated from the wave source 1200 has the first power, and the second wave L21 that is multiply scattered and emitted from the pipe unit 1110 has the second power. Ideally, the first power of the first wave L11 and the second power of the second wave L21 are equal to each other, and the wave source 1200 may irradiate waves with power of 1 mW/cm² or more but the first power of the first wave L11 is significantly reduced in a multiple scattering process. Therefore, the second power of the second wave L21 may be smaller than the first power of the first wave L11. The second power of the second wave L21 may be different according to the diameter R1 of the pipe unit 1110, the first power magnitude of the first wave L11, a degree of absorption of the fluid with respect to a wavelength of the first wave L11 and a diameter R2 of the emission hole 1103. For example, the second power of the second wave L21 may be proportional to the first power of the first wave L11, inversely proportional to the diameter R1 of the pipe unit 1110, and proportional to the diameter R2 of the emission hole 1103.

Meanwhile, when an image sensor is used as the detector 1300, the image sensor may be disposed such that a size d of one pixel of the image sensor is smaller than or equal to a grain size of a speckle pattern. For example, the image sensor may be disposed in an optical system included in the detector 300 to satisfy the condition of Equation 4 below.

$$d \leq \text{speckle grain size} \quad \text{[Equation 4]}$$

As shown in Equation 4, the size d of one pixel of the image sensor should be less than or equal to the grain size of the speckle pattern. However, if the size of the pixel becomes too small, undersampling may occur and there may be difficulties in utilizing pixel resolution. Accordingly, the image sensor may be disposed such that a maximum of five pixels or less are positioned at a speckle grain size to achieve an effective signal to noise ratio (SNR).

The controller 1400 may obtain a temporal correlation of the detected laser speckles using the detected laser speckles. The controller 1400 may estimate the presence of impurities in the fluid in real time based on the obtained temporal correlation. Real time in the present specification means estimating the presence of the microbe M within 3 seconds, preferably, it is possible to estimate the presence of the microbe M within 1 second.

In an embodiment, the controller 1400 may use a difference between first image information of the laser speckle detected at the first time and second image information of a second laser speckle detected at the second time to estimate the presence of the microbe M. Here, the first image information and the second image information may be at least one of pattern information of the laser speckle and intensity information of waves. Meanwhile, an embodiment of the present disclosure does not use only the difference between the first image information at the first time and the second image information at the second time but may extend this to use image information of a plurality of laser speckles at a plurality of times. The controller 1400 may calculate a temporal correlation coefficient between images using image information of laser speckles generated for a plurality of preset times, and estimate the presence of the microbe M in the fluid based on the temporal correlation coefficient. The detected temporal correlation of the laser speckle images may be calculated using Equation 5 below.

$$\overline{C}(x, y; \tau) = \frac{1}{T-\tau} \sum_{t=1}^{T-\tau} \overline{I}(x, y; t)\overline{I}(x, y; t+\tau)\delta t \quad \text{[Equation 5]}$$

In Equation 5, $\overline{C}$ denotes the temporal correlation coefficient, $\overline{I}$ denotes normalized light intensity, (x, y) denotes a pixel coordinate of a camera, t denotes a measured time, T denotes a total measurement time, and τ denotes a time lag.

The temporal correlation coefficient may be calculated according to Equation 5, and in an embodiment, the presence of the microbe may be estimated through an analysis in which the temporal correlation coefficient falls below a preset reference value. Specifically, it may be estimated that the microbe is present from that the temporal correlation coefficient falls below the reference value exceeding a preset error range.

Referring to FIG. 3 again, in another embodiment, the impurity detection system 10' may include a plurality of detectors 1310, 1330, and 1350. As described above, a plurality of emission holes 1103 may be formed in the body portion 1100 of the pipe unit 1110, and the detectors 1300 may be positioned at positions corresponding to the respective emission holes 1103.

The first wave L11 irradiated to the pipe unit 1110 may be multiply scattered in the fluid and then emitted through the emission hole 1103, and the second power of the emitted second wave L21 may be different according to the position of the emission hole 1103. The first wave L11 irradiated to the pipe unit 1110 is scattered according to the interval Λ and the depth d of the pattern in the multiple scattering amplification region MSA1. The pattern has irregularity due to tolerances or intentional patterning in a manufacturing process. Accordingly, the first wave L11 is not scattered regularly in the fluid of the multiple scattering amplification region MSA1 but is scattered irregularly, and the second power of the second wave L21 may be different according to the emission position. The impurity detection system 10' according to another embodiment of the present disclosure detects the laser speckle of the second wave L21 emitted by using the plurality of detectors 1310, 1330, and 1350 disposed at different positions, and thus a stable impurity detection is possible.

Specifically, the plurality of detectors 1310, 1330, and 1350 may detect the second wave L21 having different second powers. For example, the first detector 1310 may detect the second wave L21 having a 2-1th power, the second detector 1330 may detect the second wave L21 having a 2-2th power, and the third detector 1350 may detect the second wave L21 having a 2-3th power. The 2-1th power, the 2-2th power, and the 2-3th power may have different values. Ideally, because the irradiated first wave L11 is multiply scattered in the pipe unit 1110 in various directions and fills up the cross-section of the pipe unit 1110, the microbe M of a fine size may be effectively detected regardless of which direction the laser speckle is detected.

However, in an actual detection environment, the power of the emitted second wave L21 may be different according to the position due to factors such as a pattern degree of the pipe unit 1110 or a flow rate of the fluid. If only the first detector 1310 is provided, the second wave L21 of the 2-1th power is detected. In this case, a position corresponding to the first detector 1310 may be a shade region of the second wave L21, which may reduce detection power. The impurity detection system 10' may include a plurality of emission holes 1103, and the plurality of detectors 1310, 1330, and 1350 disposed in various directions, and thus complementary detection may be possible. The controller 1400 may detect impurities using values detected by the first to third detectors 1310, 1330, and 1350. For example, the controller 1400 may average information of laser speckles detected by the first to third detectors 1310, 1330, and 1350 and utilize the information to detect impurities.

In this case, when there are two or more emission holes 1103, the emission holes 1103 may be disposed at different positions of the body portion 1100, and the detectors 1310,

1330, and 1350 may be provided to correspond to the number of emission holes 1103. The impurity detection system 10' may allow the detectors 1310, 1330, and 1350 to be disposed at different positions on the same circumference, and thus when the impurity microbe M pass through the same cross section of the pipe unit 1110, the impurity microbe M may be detected at the same time. In addition, when a plurality of emission holes 1103 are provided, one of the emission holes 1103 may be disposed on the same circumference as an incidence position at which the first wave L11 is incident from the wave source 1200. The emission holes 1103 except for the one emission hole 1103 may be disposed on a circumference different from the wave source 1200. For example, as shown, the plurality of emission holes 1103 may be disposed on different circumferences so as not to overlap with respect to the longitudinal direction of the pipe unit 1110.

Meanwhile, the impurity detection system 10 may be capable of detecting impurities when the impurities in the fluid are present in a certain concentration range. The impurity detection system 10 may also perform a function of measuring an optical density (OD) of the fluid by estimating the concentration of impurities in the fluid. It is difficult for a general OD measuring device in measuring impurity concentration of $10^5$ cfu/ml or less. However, the impurity detection system 10 according to an embodiment of the present disclosure may also be capable of measuring the impurity concentration of $10^5$ cfu/ml or les through a method of determining the impurity concentration as follows. Here, impurities are not limited to microbes. The impurity detection system 10 may be capable of detecting impurities even at $1 \times 10^0$ cfu/ml by the number of times of multiple scattering of the amplified first wave L11. In addition, the impurity detection system 10 may be capable of detecting impurities even when the impurities of the range of $9 \times 10^9$ cfu/ml are present. When the range is converted into an OD range, the impurity detection system 10 may be capable of detecting impurities in the fluid with an OD in the range of 0 to 30.

Hereinafter, for convenience of description, a method, performed by the controller 1400, of determining the concentration of microbes by using a laser speckle will be described mainly on the case where impurities are microbes.

The controller 1400 may calculate a standard deviation of light intensity of the laser speckle on a laser speckle image measured at each reference time. As microbes included in the fluid continuously move, constructive interference and destructive interference may change in response to the movement. In this case, as the constructive interference and the destructive interference change, a degree of light intensity may change greatly. Then, the controller 1400 may detect the microbes by calculating the standard deviation indicating the degree of change in the light intensity, and measure the distribution of the microbes.

For example, the controller 1400 may synthesize the laser speckle image measured at a predetermined time and calculate the standard deviation of the light intensity of the laser speckle over time from the synthesized image. The standard deviation of light intensity of the laser speckle over time may be calculated based on Equation 6 below.

$$S(x, y) = \sqrt{\frac{1}{T}\sum_{t=1}^{T}(I_t(x, y) - \bar{I})^2} \quad \text{[Equation 6]}$$

In Equation 6, S may denote the standard deviation, (x, y) may denote camera pixel coordinates, T may denote the total measurement time, t may denote the measurement time, It may denote light intensity measured at the time t, and $\bar{I}$ may denote a mean light intensity over time.

Constructive and destructive interference patterns vary according to the movement of the microbes, and a standard deviation value calculated based on Equation 6 may become large, and thus the concentration of the microbes may be measured. However, the present disclosure is not limited to the method of measuring the concentration of the microbes by Equation 6 above, and may measure the concentration of the microbes by using any method using a difference of the detected laser speckle.

The controller 1400 may estimate a distribution, i.e., concentration, of the microbes included in the fluid based on a linear relationship between the magnitude of a standard deviation value of a light intensity of a second laser speckle and the microorganism concentration.

Figure 6A:
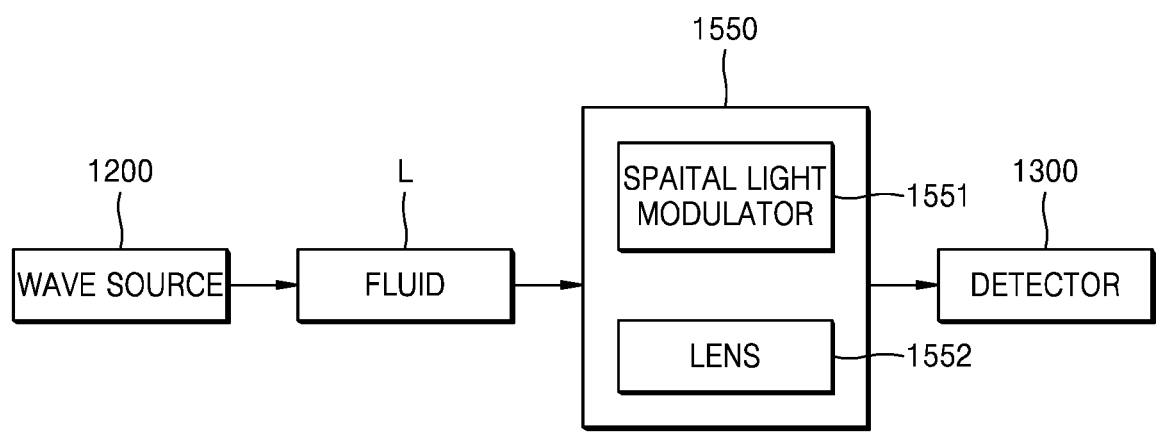
FIGS. 6A and 6B are conceptual diagrams schematically showing an impurity detection system according to another embodiment of the present disclosure.
Figure 6B:
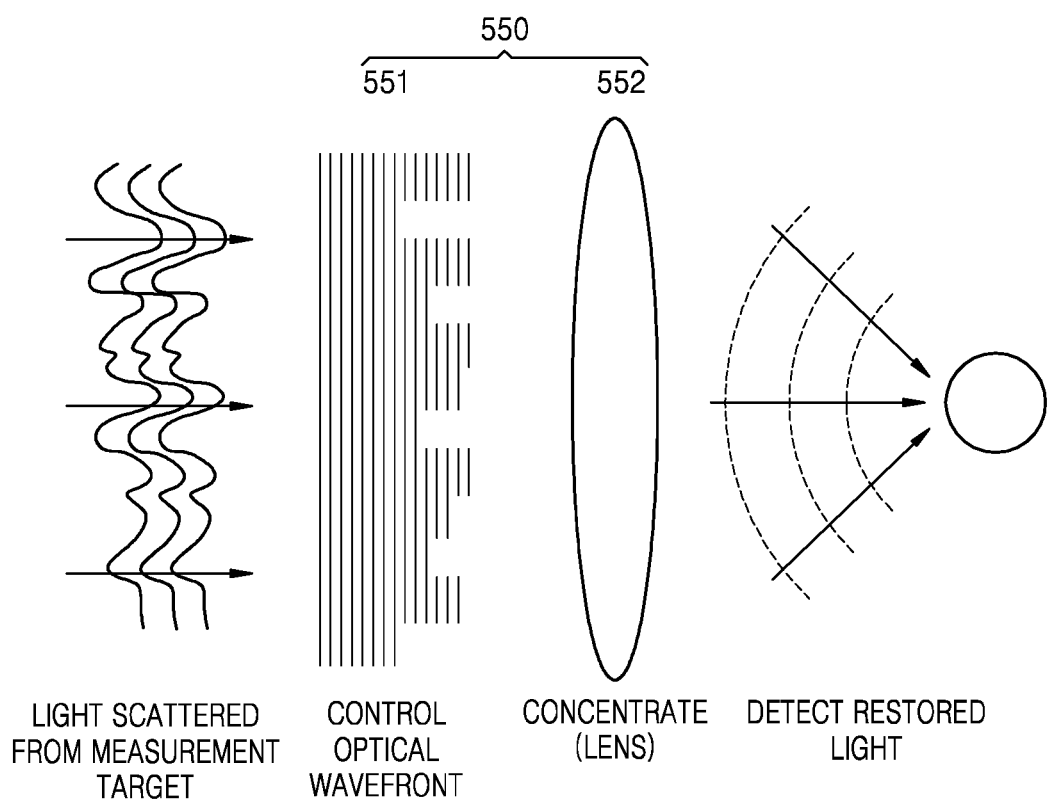

Meanwhile, FIGS. 6A and 6B are conceptual diagrams schematically showing an impurity detection system according to another embodiment of the present disclosure.

Referring to FIGS. 6A and 6B, the impurity detection system may further include an optical unit 1550 restoring and modulating a first wave signal scattered in a fluid into a second wave signal before a first wave of the wave source 1200 is scattered by the fluid. In this case, the optical unit 1550 may include a spatial light modulator (SLM) 1551 and the detector 1300. When a scattered wave is incident from a measurement target, the optical unit 1550 may control a wavefront of the scattered wave, restore the wave to a wave (light) before being scattered, and provide the wave to the detector 1300.

The wave (light) may be incident on the SLM 1551 from a sample. The SLM 1551 may control a wavefront of the wave scattered from the sample to provide the wave to a lens 1552. The lens 1552 may concentrate the controlled light and provide the light to the detector 1300 again. The detector 1300 may detect the wave concentrated by the lens and restore and output the wave output from an initial wave source to be scattered.

Here, when a microbe is not present in a stable medium, that is, the fluid, the optical unit 1550 may restore the first wave signal scattered from the fluid to the wave before scattered. However, when the microbe M is present in the fluid, because the first wave signal changes due to a movement of the microbe, a phase control wavefront may not be detected, and thus the first wave signal may not be modulated into the second wave signal having a phase conjugation wavefront. The impurity detection system including the optical unit 1550 described above may estimate the presence of impurities more finely by using a difference of the second wave signal.

Figure 7:
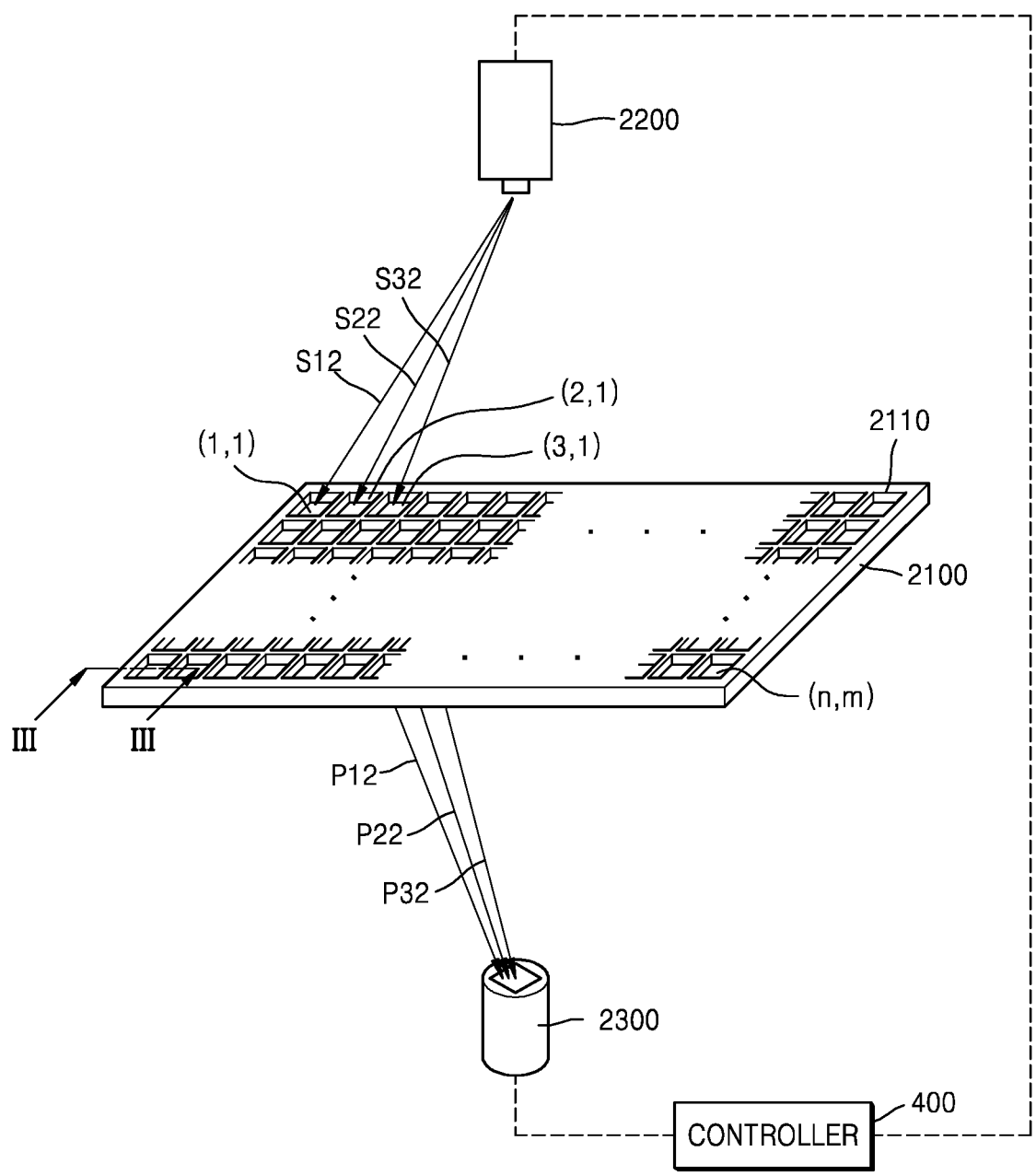
FIG. 7 is a conceptual diagram schematically showing a microbial population counting system according to an embodiment of the present disclosure.
Figure 8:
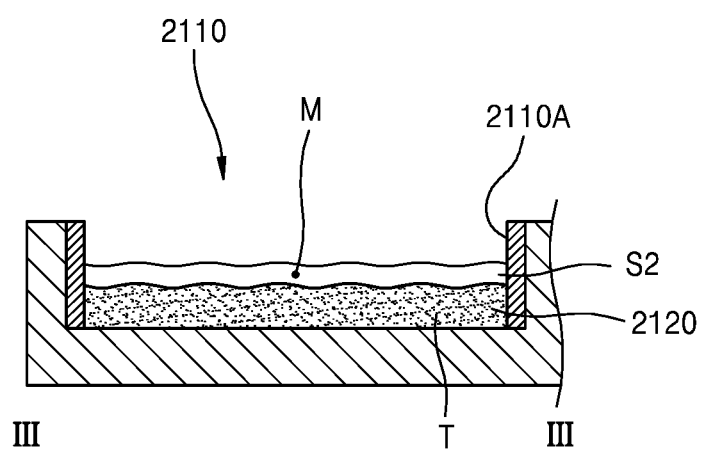
FIG. 8 is a cross-sectional view taken along a line III-III of FIG. 7.

FIG. 7 is a conceptual diagram schematically showing a microbial population counting system 20 according to an embodiment of the present disclosure. FIG. 8 is a cross-sectional view taken along line III-III of FIG. 7.

Referring to FIGS. 7 to 8, the microbial population counting system 20 according to an embodiment of the present disclosure may include a sample placement unit 2100, a wave source 2200, a detector 2300, and a controller 2400.

As used herein, the term "microbe" refers to a prokaryotic or eukaryotic microbe with the ability to produce useful target substances such as L-amino acids. For example, a microbe with an increased intracellular ATP concentration may be a microbe belonging to *Escherichia* sp., *Erwinia* sp.,

*Serratia* sp., *Providencia* sp., *Corynebacterium* sp., *Pseudomonas* sp., *Leptospira, Salmonella* sp., *Brevibacteria* sp., *Hypomononas.* sp., *Chromobacterium* sp., *Norcardia*, fungi, or yeast. Specifically, the microbe may be the *Escherichia* sp. microbe.

Alternatively, the microbe may include bacteria selected from the group consisting of *Staphylococcus*, staph Coagulase negative, *Staph. Aureus, Streptococcus* spp., *Streptococcus viridans* group, *Enterococcus* spp., *Corynebacterium* spp., *Aerococcus* spp., *Micrococcus* spp., *Peptostreptococcus* spp., *Lactococcus* spp., *Leuconostoc* spp.), *Tothia* spp. *Gemella* spp., *Alcaligenes* spp., *Alternaria* spp., *Flavobacterium* spp., *Bacillus* spp., *Achromobacter* spp., *Acinetobacter* spp., *Actinobacillus* spp., *Alcaligenes* spp., *Campylobacter* spp., *Edwardsiella* spp., *Ehrlichia* spp., *Enterobacter* spp., *Ewingella* spp., Flavobacteria, *Hafnia* spp., *klebsiella, Klebsiella* spp., *Kluyvera* spp., *Legionella* spp., *Morxella* spp., *Morganella* spp., *Neisseria* spp., *Pasteurella* spp., *Prevotella* spp., *Proteus* spp., *Providencia* spp., *Pseudomonas* spp., *Rahnella* spp., *Salmonella* spp., *serratia, Serratia* spp., *Shigella* spp., *Sphingobacterium* spp., *Vibrio* spp., *yersinia, Yersinia* spp., *Neisseria* spp., *Kingella* spp., *Cardiobacterium*, NTB:non-*Tuberculosis mycobacteria*), *Mycobacterium tuberculosis*, and *Mycobacterium avium*. More specifically, the microbe may be *E. coli*. However, the technical idea of the present disclosure is not limited thereto, and may further include other microbes.

The sample placement unit 2100 may include a plurality of split cells 2110 distributing and accommodating samples to be measured. In this case, each of the plurality of split cells 2110 may include a culture material 2120 for microbe culture. The culture material 2120 may include a material corresponding to a type of microbe to be counted to effectively culture the microbe.

A medium including the culture material 2120 used for culture should suitably meet the requirements of a specific microbe. Various microbe culture media are described, for example, in "Manual of Methods for General Bacteriology" by the American Society for Bacteriology, Washington D.C., USA, 1981.) These media include various carbon sources, nitrogen sources and trace element components. Carbon sources may include carbohydrates such as glucose, lactose, sucrose, fructose, maltose, starch and fiber; fats such as soybean oil, sunflower oil, castor oil and coconut oil; fatty acids such as palmitic acid, stearic acid and linoleic acid; alcohols such as glycerol and ethanol and organic acids such as acetic acid, and these carbon sources may be used alone or in combination, but are not limited thereto. Nitrogen sources may include organic nitrogen sources and urea, such as peptone, yeast extract, gravy, malt extract, corn steep liquor (CSL), and bean flour, and inorganic nitrogen sources such as ammonium sulfate, ammonium chloride, ammonium phosphate, ammonium carbonate, and ammonium nitrate, and these nitrogen sources may be used alone or in combination, but are not limited thereto. The medium may further include potassium dihydrogen phosphate, dipotassium hydrogen phosphate, and corresponding sodium-containing salts as phosphoric acid sources, but is not limited thereto. The medium may also include metals such as magnesium sulfate or iron sulfate, and amino acids, vitamins and suitable precursors may be added.

In addition, in order to maintain aerobic conditions of a culture solution, oxygen or a gas including oxygen (e.g., air) may be injected into the culture solution. A temperature of the culture may generally be 20-45° C., specifically 25-40° C.

Here, a sample S2 may be prepared by diluting according to the dilution ratio for counting the number of colonies. In general, the number of bacteria that may be deployed on a plate and measured separately is about 1000 as the number of colonies of *E. coli* in the case of the plate having a diameter of 10 cm. As will be described later, in the present disclosure, because after microbes are deployed on the plate, each of the microbes included in the plurality of divided cells 2110 may be detected without forming a colony, the number of countable bacteria may be different according to the dilution ratio of the sample S2 and/or the number of split cells 2110, and more bacteria may be counted than the bacteria described above.

Specifically, the plurality of split cells 2110 may be provided in the form of a matrix of (n, m), and the number thereof may be greater than a predicted microbial population included in the sample S2. As will be described later, the samples S2 may equally accommodated in the plurality of split cells 2110, and may be prepared generally by diluting according to a dilution ratio for counting the number of colonies. For example, when the plurality of split cells 2110 is provided in a matrix of (100, 100), the sample S2 may be diluted such that the microbial population does not exceed $10^4$. Alternatively, when the plurality of divided cells 2110 is provided in a matrix of (100, 100), the sample S2 may be diluted such that the microbial population does not exceed $10^6$.

Meanwhile, the sample placement unit 2100 may include a multiple scattering amplification region for amplifying the number of times a wave incident on the split cell 2110 is multiply scattered in the sample S2. For example, the sample placement unit 2100 may be formed by including a multiple scattering material in at least a lower region. For example, the multiple scattering material may include titanium oxide ($TiO_2$), and may reflect at least a part of the wave passing through the sample S2 and incident on the sample placement unit 2100. The multiple scattering amplification region may cause waves that are multiply scattered from the sample S2 to reciprocate a space between the sample S2 and the multiple scattering amplification region at least one time.

In another embodiment, the microbial population counting system 20 may be configured such that a multiple scattering material T2 the time T2 is included in the culture material 2120. In FIG. 2, the culture material 2120 and the sample S2 are separated from each other, but may be mixed with the culture material 2120 when the sample S2 is accommodated in the split cell 2110. At this time, the multiple scattering material T2 may be arranged to surround the microbe M to scatter the incident wave and increase the number of times of multiple scattering.

Meanwhile, in another embodiment, the microbial population counting system 20 may further include a separate multiple scattering amplifier (not shown). The multiple scattering amplifier (not shown) may be provided on a wave movement path between the wave source 2200 and the sample placement unit 2100 and/or between the sample placement unit 2100 and the detector 2300 to amplify the number of times of multiple scattering of waves. When the multiple scattering amplifier (not shown) is disposed between the wave source 2200 and the sample placement unit 2100, the multiple scattering amplifier may be formed in a detachable structure to distribute the sample S2 to the sample placement unit 2100. For example, the multiple scattering amplifier (not shown) may be configured in a structure such as a lid. In addition, the multiple scattering amplifier (not shown) may be provided to correspond to each of the split cells 2110, or may be formed in a structure covering the entirety of the plurality of split cells 2110.

Meanwhile, the sample placement unit 2100 may include a blocking region 2110A on a side surface of each split cell 2110 to block the wave incident to each split cell 2110 not to introduce into another split cell 2110. The microbial population counting system 20 according to an embodiment of the present disclosure sequentially irradiates waves to the plurality of split cells 2110 and detects laser speckles emitted correspondingly. As will be described later, such a process should accurately detect whether the microbe is present in each of the plurality of split cells 2110, and the accuracy thereof may be reduced due to a laser speckle emitted from the split cell 2110 other than the corresponding split cell 2110 during a rapid detection process. In order to prevent this, the sample placement unit 2100 may include the blocking region 2110A on the side surface of each split cell 2110, such that a wave incident on the corresponding split cell 2110 may be introduced into the other split cell 2110 so as not to cause interference. In an embodiment, the blocking region 2110A may include a metal material having a reflective characteristic.

Meanwhile, in FIG. 8, only the blocking region 2110A is disposed on the side surface of the split cell 2110, but the technical idea of the present disclosure is not limited thereto. In another embodiment, the blocking region 2110A may also be disposed on a lower surface of the split cell 2110. In this case, unlike that shown in FIG. 8, the detector 2300 may be disposed on an upper portion of the sample placement unit 2100 to detect an emitted laser speckle. Alternatively, the detector 2300 may be disposed to face the wave source 2200 with respect to the sample placement unit 2100 as shown in FIG. 7 but may detect a laser speckle emitted through a predetermined through region of the lower surface of the sample placement unit 2100 in which a blocking region is not formed.

Although not shown, the sample placement unit 2100 may further include a reference cell (not shown) formed in the same shape as the plurality of split cells 2110 and positioned on an irradiation path of wave. At this time, the reference cell (not shown) may have the same size as the plurality of split cells 2110 to include a culture material of the same type and capacity. However, unlike the split cells 2110, the sample S2 is not accommodated in the reference cell (not shown).

The culture material may have some degree of fluidity, which may act as noise to detect a laser speckle according to a subtle movement of a microbe. In this case, because the reference cell (not shown) provided in the sample placement unit 2100 together with the plurality of split cells 2110 does not accommodate the sample S2 but includes the culture material, when a subtle vibration occurs in the sample placement unit 2100 and thus the culture material of the plurality of split cells 2110 has fluidity, the culture material of the reference cell (not shown) also has the same fluidity. The microbial population counting system 20 may equally irradiate waves to the reference cell (not shown) and set a laser speckle detected therefrom as a reference value, thereby removing noise to correctly identify the presence of the microbe in the other split cells 2110.

Referring to FIGS. 7 and 8 again, the wave source 2200 may sequentially irradiate waves to the plurality of split cells 2110 of the sample placement unit 2100. The wave source 2200 may apply all kinds of source device capable of generating waves, and may be, for example, a laser capable of irradiating light of a specific wavelength band. Meanwhile, the wave source 2200 may be connected to a driving device such as a motor or an actuator to sequentially irradiate waves toward the respective split cells 2110 according to a preset time interval. Although the present disclosure is not limited to a type of a wave source, a case where the wave source is the laser will be described for convenience of description.

For example, laser with a good coherence may be used as the wave source 2200 to form speckle in the sample S2 accommodated in the plurality of split cells 2110. In this case, the shorter the spectral bandwidth of the wave source that determines the coherence of the laser wave source, the greater the measurement accuracy. That is, the longer the coherence length, the greater the measurement accuracy. Accordingly, a laser light whose spectral bandwidth of the wave source is less than a predetermined reference bandwidth may be used as the wave source 1200, and the measurement accuracy may increase as the spectral bandwidth of the wave source is shorter than the reference bandwidth.

Meanwhile, the detector 2300 may sequentially detect individual wave information emitted from the sample S2 accommodated in each split cell 2110 in association with sequentially irradiated waves. At this time, the individual wave information may be information obtained by detecting a laser speckle generated by multiple scattered from the sample S2 accommodated in each of the plurality of split cells 2110 for each preset time. Specifically, the individual wave information includes first image information of a laser speckle detected at a first time, second image information of a laser speckle detected at a second time, and third image information of a laser speckle detected at a third time among the laser speckles emitted from the corresponding split cell 2110, wherein the first to third times may be different times. The detector 2300 may provide the controller 2400 with information about the laser speckles detected at the first to third times with respect to the one split cell 2110. In this case, the first to third times are the minimum number of detections for the controller 2400 to analyze temporal correlation of the laser speckles, and the detector 2300 may detect the laser speckles at a plurality of times more than the times.

Here, time means any moment in a continuous flow of time, and times may be set in advance at the same time interval, but are not limited thereto, and may be set in advance at any time interval. The detector 2300 may include a sensing means corresponding to a type of the wave source 2200. For example, when a light source of a visible light wavelength band is used, a CCD camera which is an image capturing device may be used.

Specifically, when a wave is irradiated to the sample S2 accommodated in the one split cell 2110, the incident wave may form a laser speckle by multiple scattering.

Because the laser speckle is generated by the interference of light, if there is no microbe in the sample S2, a multiple scattering amplification region may always show a constant interference pattern over time. In comparison, when the microbe M is present in the sample S2, the laser speckle may change over time by a movement of the microbe M. The detector 2300 may detect the laser speckle that changes over time for each preset time and provide the laser speckle to the controller 2400. The detector 2300 may detect the laser speckle at a speed sufficient to detect the movement of the microbe M, and for example, may detect the laser speckle at the speed of 25 to 30 frames per second.

The controller 2400 may determine the presence of the microbe M in each split cell 2110 using the detected individual wave information, and calculate the microbial population in the sample S2 by using the number of split cells 2110 in which the microbe M is present. Specifically, the controller 2400 may obtain a temporal correlation of the detected laser speckles using the detected laser speckles and determine the presence of the microbe M in the corresponding split cell 2110 based on the obtained temporal correlation. The controller 2400 may estimate the presence of the microbe in each split cells 2110 in real time based on the obtained temporal correlation. Real time in the present specification means estimating the presence of the microbe M within 3 seconds, preferably, it is possible to estimate the presence of the microbe M within 1 second.

In an embodiment, the controller 2400 may estimate the presence of the microbe using the laser speckles emitted from the sample S2 at different times due to the wave irradiated to the one divided cell 2110. For example, in FIG. 7, when a first wave S12 is irradiated to a (1,1) split cell, the controller 2400 may estimate the presence of the microbe M in the (1,1) split cell by obtaining a temporal relation between first laser speckles P12 that are multiply scattered by the first wave S12 and emitted. At this time, the controller 2400 may estimate the presence of the microbe M by using a difference between using first image information of the first laser speckle P12 detected at the first time, second image information of a first laser speckle P22 detected at the second time, and third image information of a first laser speckle P32 detected at the third time.

Here, the first image information to the third image information may be at least one of pattern information of the laser speckle and intensity information of waves. Meanwhile, an embodiment of the present disclosure may use the difference between the at least three image information of the laser speckles detected at different times, but may extend this to use image information of a plurality of laser speckles at a plurality of times. The controller 2400 may calculate a temporal correlation coefficient between images using the image information of the laser speckles generated for a plurality of preset times, and estimate the presence of the microbe M in the corresponding split cell 2110 based on the temporal correlation coefficient.

Hereinafter, a method of counting the microbial population using the microbial population counting system 20 described above will be described in detail.

Figure 9:
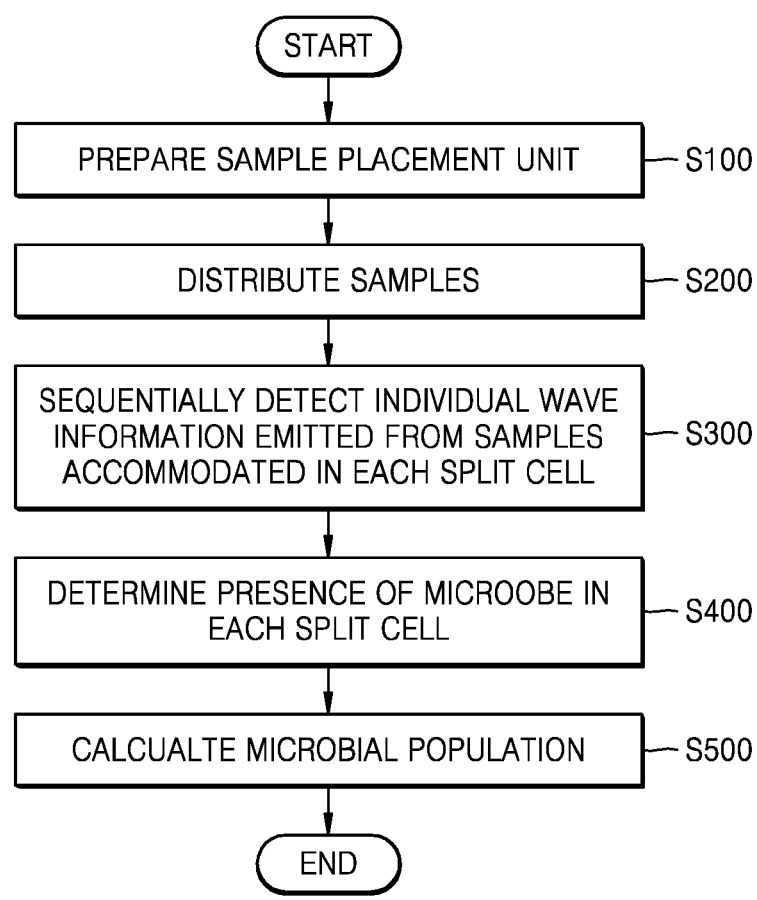
FIG. 9 is a flowchart sequentially showing a method of counting a microbial population according to an embodiment of the present disclosure.
Figure 10:
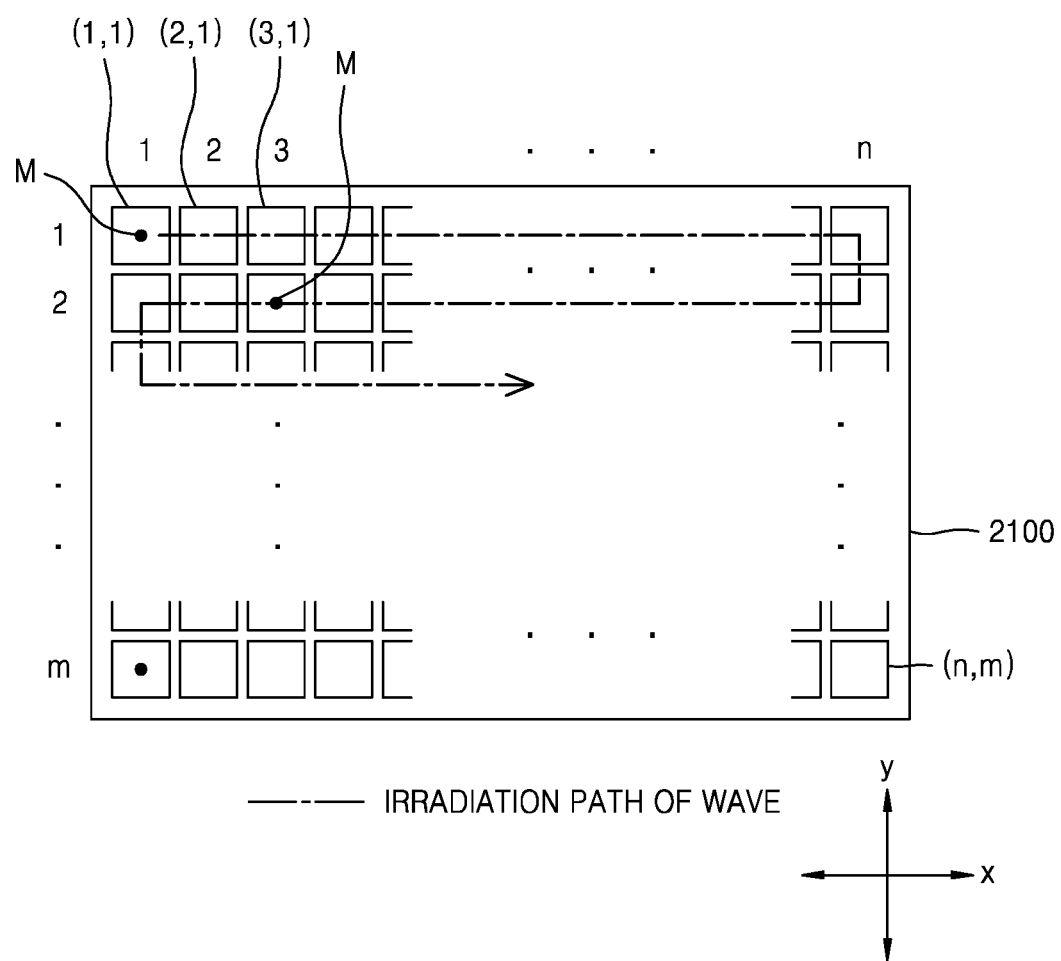
FIGS. 10 and 11 are diagrams for explaining a method of counting a microbial population.
Figure 11:
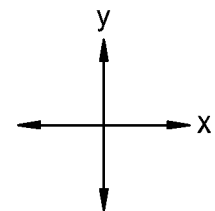

FIG. 9 is a flowchart sequentially showing a method of counting a microbial population according to an embodiment of the present disclosure, and FIGS. 10 and 11 are diagrams for explaining the method of counting the microbial population.

Referring to FIGS. 9 to 11, the method of counting the microbial population according to an embodiment of the present disclosure may, first, prepare the sample placement unit 2100 (S100). The sample placement unit 2100 may include the plurality of split cells 2110 each including a culture material.

Thereafter, the sample S2 to be measured is diluted at a predetermined dilution ratio and distributed to the plurality of split cells 2110 (S200). At this time, sizes of the plurality of split cells 2110 are equally configured, and the sample S2 may be uniformly distributed Because the sample S2 is diluted such that an expected microbe M population is smaller than the number of the plurality of split cells 2110, when the sample S2 is uniformly distributed, as shown in FIG. 4, the microbe M may be or may not be present in each split cell 2110.

Thereafter, waves may be sequentially irradiated to the plurality of split cells 2110 by the wave source 2200, and individual wave information emitted from the sample S2 accommodated in each split cell 2110 may be sequentially detected in association with sequentially irradiated waves (S300). For example, when the plurality of split cells 2110 are arranged in the form of an (n, m) matrix as shown, the waves may be irradiated in a sequentially scanning manner along each column. At this time, the detector 2300 detects individual wave information emitted from each split cell 2110 in association with the irradiated waves. As described above, the individual wave information may be a plurality of pieces of image information of laser speckles detected at different times in the corresponding split cell 2110.

The controller 2400 may determine the presence of the microbe M in each split cell 2110 using the detected individual wave information (S400).

For example, as shown in FIG. 4, when the microbe M is present in the (1,1) split cell and the microbe M is not present in a (2,1) split cell, the controller 2400 may define the (1,1) split cell as 1 and the (2,1) split cell as 0. Such determination of the presence of the microbe M may be performed from the (1,1) split cell to the (n, m) split cell according to an irradiation path of sequential waves.

When the determination of the presence of the microbe with respect to all the split cells 2110 is completed, the controller 2400 may calculate the microbial population in the entire samples S2 using the number of split cells in which the microbe M is present. In other words, by calculating the number of split cells defined as 1 in the entire split cells 2110, the microbial population included in the entire samples S2 may be calculated.

Figure 12:
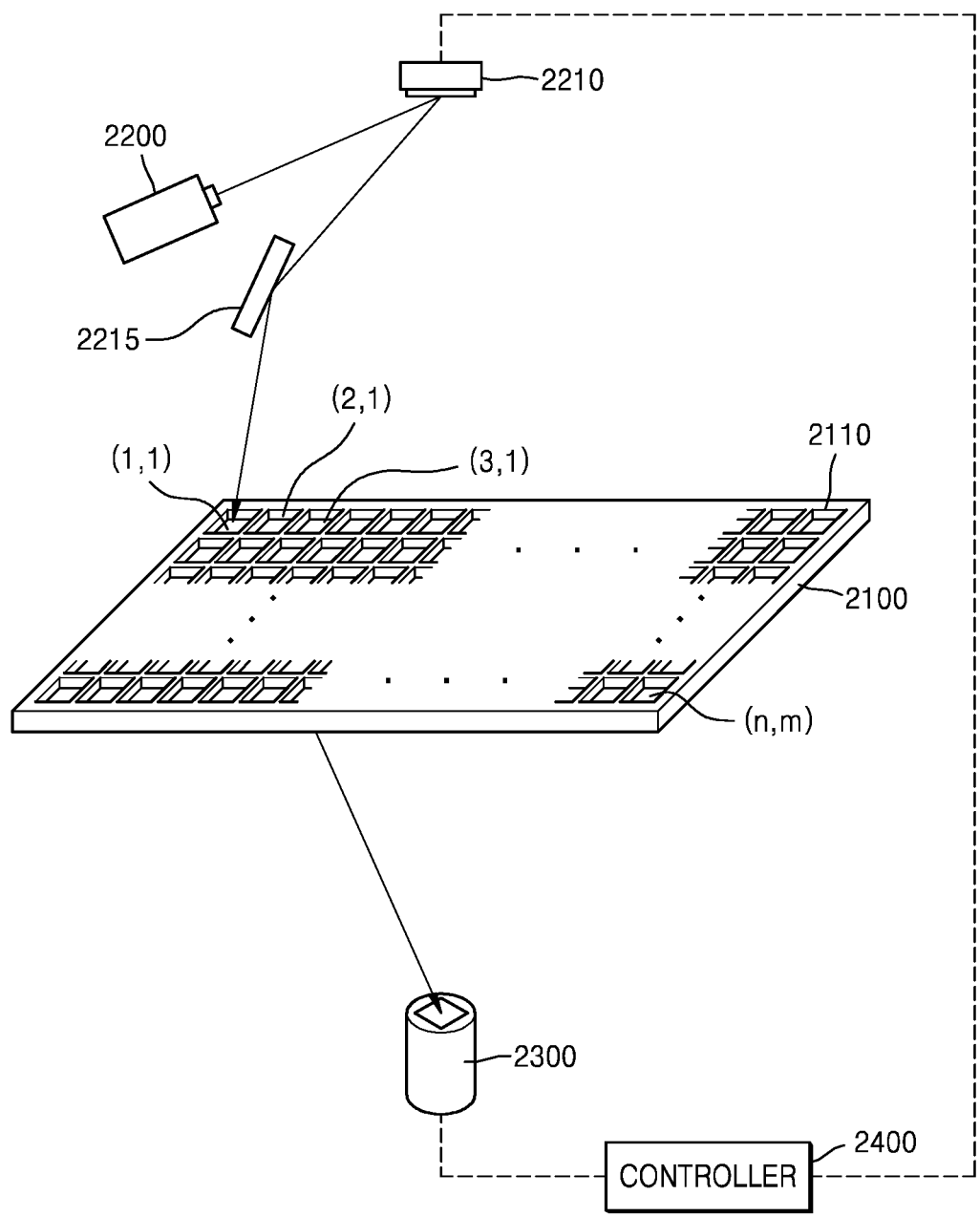
FIG. 12 is a conceptual diagram schematically showing a microbial population counting system according to another embodiment of the present disclosure.

FIG. 12 is a conceptual diagram schematically showing a microbial population counting system 20-1 according to another embodiment of the present disclosure.

Referring to FIG. 12, the microbial population counting system 20-1 according to another embodiment of the present disclosure may further include a wave path changer 2210 in order to sequentially irradiate waves irradiated from the wave source 2200 into the plurality of split cells 2110. In other words, the waves are not irradiated directly to the plurality of split cells 2110 from the wave source 2200, but the waves may be irradiated to the plurality of split cells 2110 using the wave path changer 2210. In another embodiment of the present disclosure, except for a method of irradiating waves, the other components are the same as those in an embodiment, and thus redundant descriptions will be omitted for the convenience of description.

The waves may be incident on the wave path changer 2210 from the wave source 2200. The wave path changer 2210 may be a micro mirror. The wave path changer 2210 may include a reflective surface to reflect the incident waves toward the plurality of split cells 2110. The reflective surface is shown as a flat surface without refractive power, but the present disclosure is not limited thereto. The wave path changer 2210 may be finely driven by a drive controller (not shown).

In another embodiment, the wave path changer 2210 may be finely driven by the controller 2400, and accordingly, may sequentially irradiate the waves to the plurality of split cells 2110. At this time, the controller 2400 may also control the detector 2300 to detect the laser speckle emitted from the corresponding split cell 2110 in association with a wave order irradiated by the wave path changer 2210.

The micro mirror constituting the wave path changer 2210 may employ various configurations in which mechanical displacement of the reflective surface may occur according to electrical control. For example, a generally known micro electromechanical system (MEMS) mirror, a digital micromirror device (DMD) element or the like may be employed.

The wave path changer 2210 is illustrated as one micro mirror, but this is exemplary and may be a configuration in which a plurality of micro mirrors are two-dimensionally arrayed.

Meanwhile, the wave path changer 2210 may further include a mirror 2215 disposed on the wave path to adjust angles of the waves irradiated to the plurality of split cells 2110 to be uniform. In other words, when the wave path changer 2210 irradiates the waves to the plurality of split cells 2110 using the micro mirror, the incident angles of the waves may be different according to positions of the split cells 2110. Accordingly, because a degree of multi-scattering in the sample S2 may be different according to positions of the plurality of split cells 2110, accurate comparison and evaluation may be difficult, and thus, the mirror 2215 may be further disposed such to adjust the angles of the waves irradiated to the split cells 2110 to be uniform. In the drawing, only the one mirror 2215 disposed on the (1,1) split cell is illustrated, but is schematically illustrated for convenience of description, and a mirror is disposed in an upper end of each of the split cells 2110 such that the angles of the waves irradiated to the split cells 2110 may be adjusted.

Figure 13:
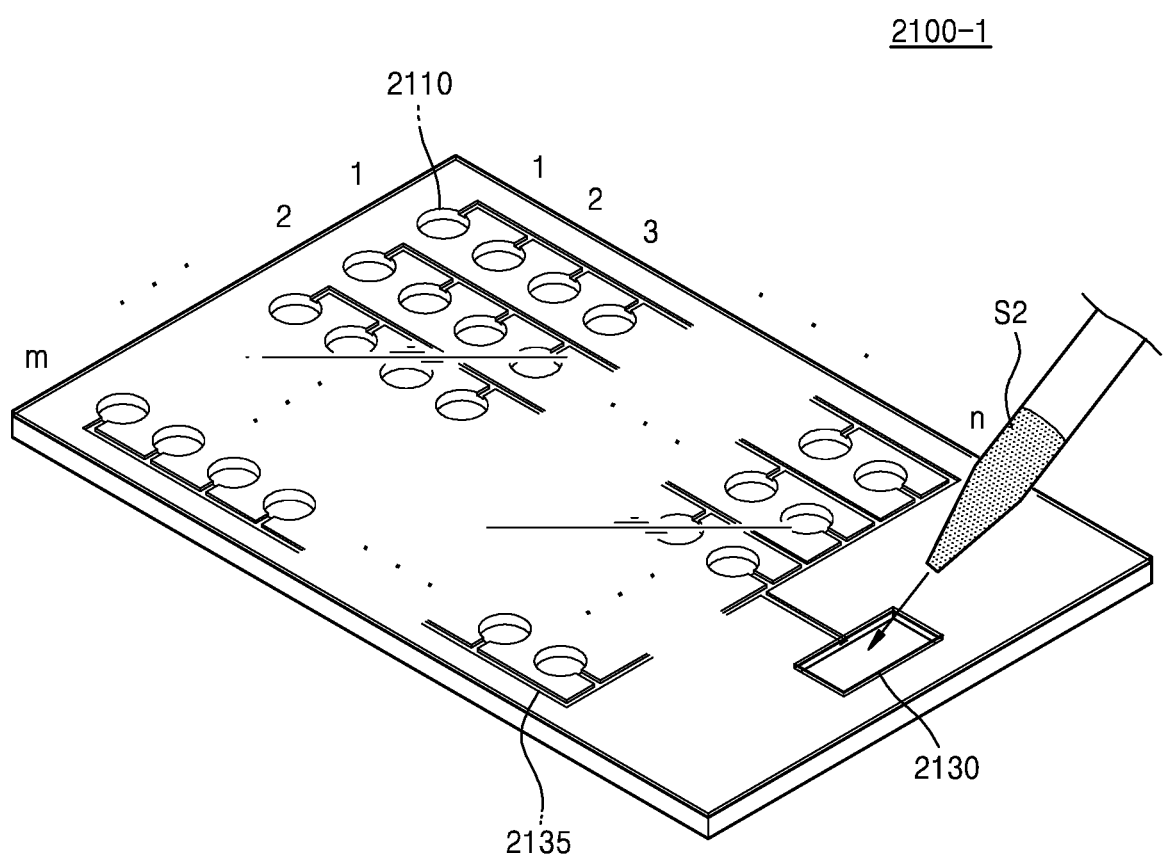
FIG. 13 is a conceptual diagram schematically showing a sample placement unit according to another embodiment of the present disclosure.

FIG. 13 is a conceptual diagram schematically showing a sample placement unit 2100-1 according to another embodiment of the present disclosure.

Referring to FIG. 13, unlike the sample placement unit 2100 of an embodiment which is formed in the form of a petri dish such as an agar plate, the sample placement unit 2100-1 according to another embodiment may be in the form of a multi-well based microfluidics chip connected to a microfluid channel 2135.

Specifically, the sample placement unit 2100-1 may include the plurality of split cells 2110 having a multi-well shape and an injector 2130 through which the samples S2 may be injected, and the plurality of split cells 2110 and the injector 2130 may connected to the microfluidics channel 2135. When the sample S2 is injected into the injector 2130, the sample placement unit 2100-1 may uniformly distribute the sample S2 to each split cell 2110 through the microfluidics channel 2135.

The sample placement unit 2100-1 according to another embodiment may include a culture material for culturing a microbe in each of the plurality of split cells 2110 in the same manner as in an embodiment. In addition, an upper surface of the sample placement unit 2100-1 may include a transparent material for optical imaging. However, the present disclosure is not limited thereto, and as described above, a multiple scattering amplifier may be disposed on the upper surface for multiple scattering amplification.

Meanwhile, the sample placement unit 2100-1 has a blocking region on at least a side surface of each split cell 2110 to block a wave incident to each split cell 2110 from entering another split cell 2110. Through the blocking region, the sample placement unit 2100-1 may minimize wave interference between the split cells 2110 to improve the accuracy of the population count. In addition, the sample placement unit 2100-1 may be provided as a disposable kit.

Figure 14:
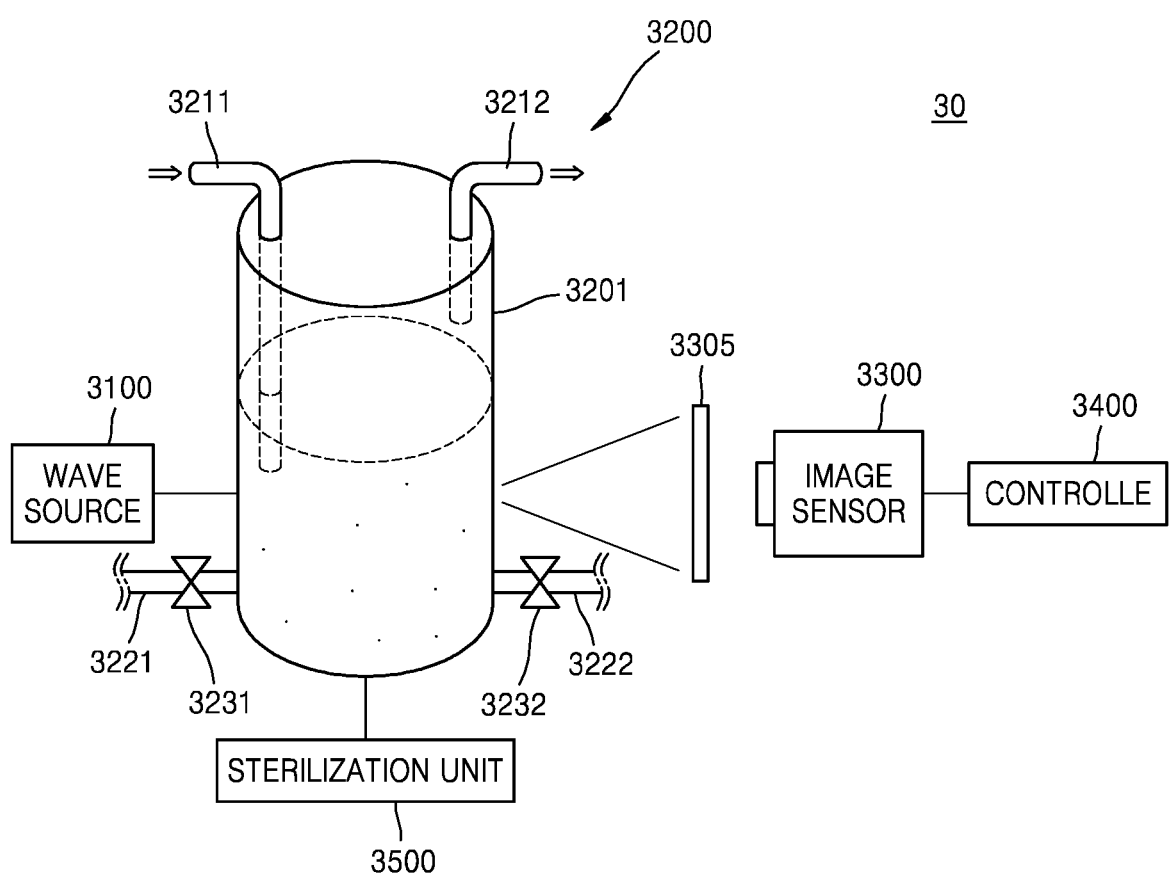
FIG. 14 is a diagram schematically showing an airborne bacteria measuring device according to an embodiment of the present disclosure.
Figure 15:
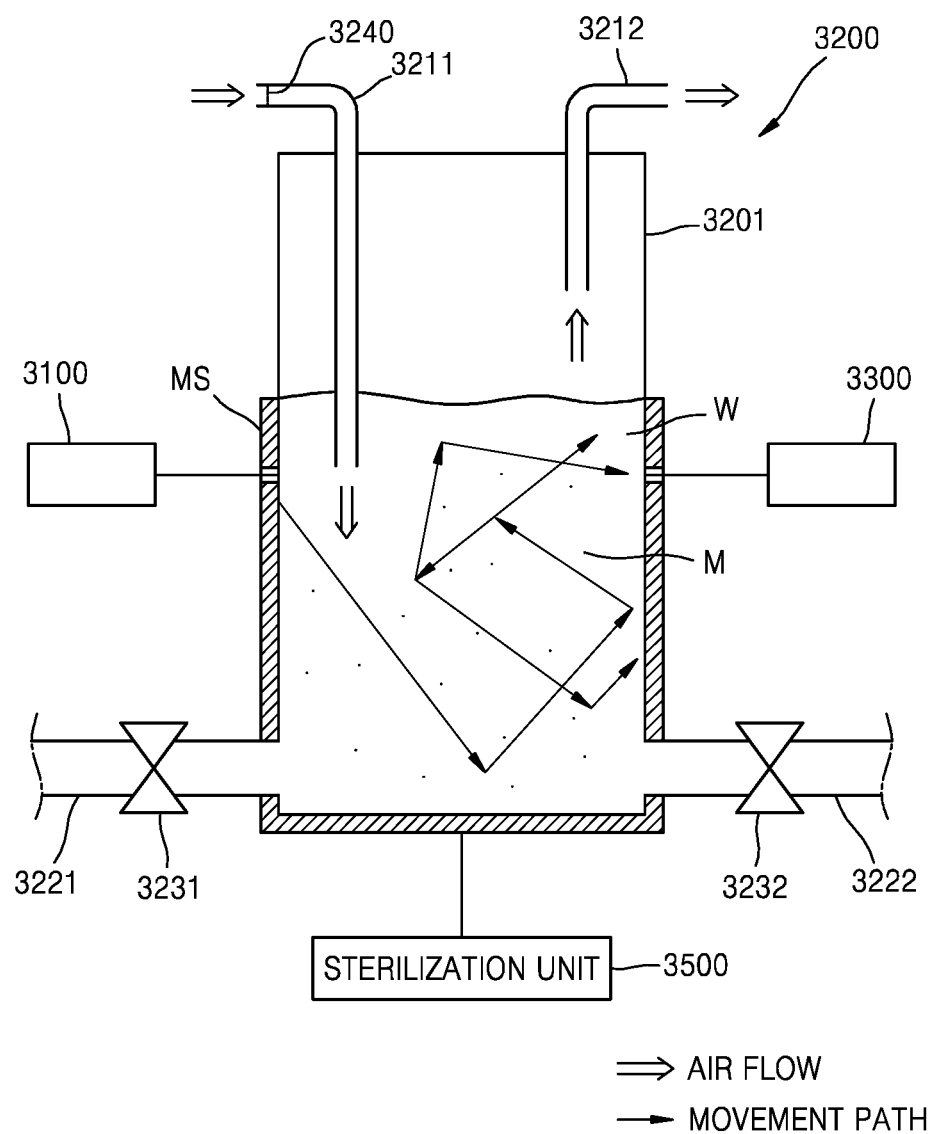
FIG. 15 is a conceptual diagram for explaining the sampling principle of the airborne bacteria measuring device of FIG. 14.
Figure 16:
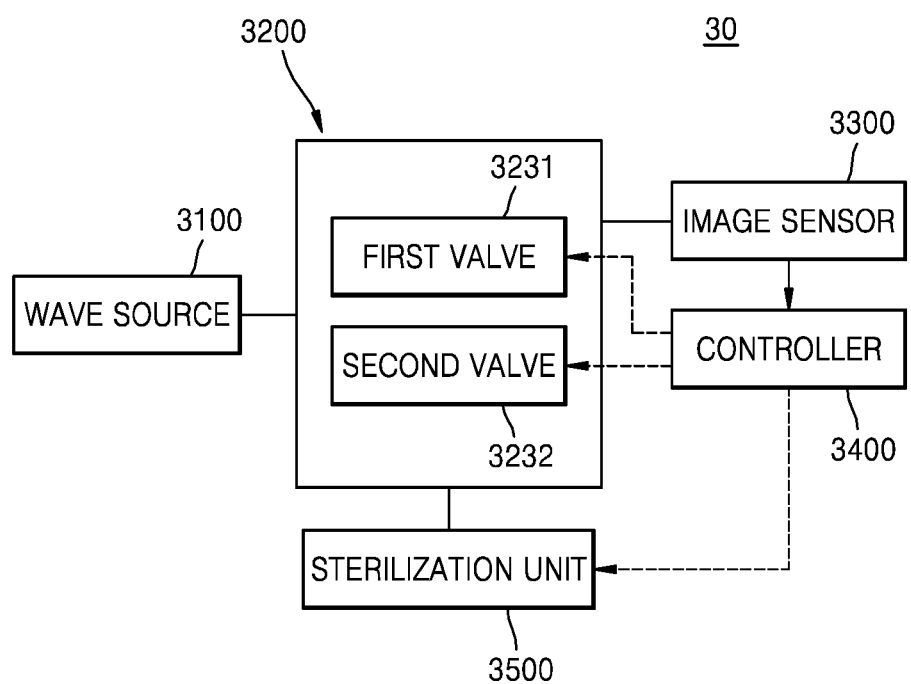
FIG. 16 is a block diagram of the airborne bacteria measuring device of FIG. 14.

FIG. 14 is a diagram schematically showing an airborne bacteria measuring device 30 according to an embodiment of the present disclosure, and FIG. 15 is a conceptual diagram for explaining the sampling principle of the airborne bacteria measuring device 30 of FIG. 14. FIG. 16 is a block diagram of the airborne bacteria measuring device 30 of FIG. 14, and FIGS. 17A to 17D are diagrams for explaining a process performed by the airborne bacteria measuring device 30 of FIG. 14 of sampling bacteria and then processing collection liquid.

The air sampler of the related art inhales air including airborne bacteria for airborne bacteria sampling and then grows the air by spreading the air in a medium to be a measurable amount. At this time, a culture time is long, which made it difficult to detect airborne bacteria quickly.

The present disclosure is to solve the above problem, and the airborne bacteria measuring device 30 according to an embodiment of the present disclosure allows air in which microbes such as bacteria and germs are floating to contact with the collection liquid, collecting the airborne bacteria in the collection liquid, and then detects the airborne bacteria using a wave speckle, and thus the airborne bacteria is detected within a short time.

First, referring to FIGS. 14 and 15, the airborne bacteria measuring device 30 according to an embodiment of the present disclosure may include a collection unit 3200, a wave source 3100, an image sensor 3300, and a controller 3400.

The collection unit 3200 performs a function of accommodating the collection liquid to collect the bacteria from the inhaled air. Specifically, the collection unit 3200 may include a storage tank 3201 for accommodating the collection liquid W therein, an inhalation flow path 3211 for inhaling external air to guide the external air to the collection liquid W in one side of the storage tank 3201, and an exhaust flow path 3212 for discharging the air of the storage tank 3201 to the outside in the other side of the storage tank 3201.

Here, the collection liquid W may be any kind of sample capable of collecting the bacteria through contact with the airborne bacteria. In other words, the collection liquid W may be a liquid or a sample in the form of a gel. However, in the present disclosure, in order to accurately detect the presence or concentration of the airborne bacteria, the collection liquid W may be prepared without including impurities such as microbes before contacting the air, or may be previously stored by in advance measuring concentration of microbes including impurities in the collection liquid W before contacting the air through a chaotic wave sensor that will be described later.

In an embodiment, the collection liquid W may include a liquid, and may include a culture material for culturing microbes. The collection liquid W may include various microbe culture materials and is described, for example, in "Manual of Methods for General Bacteriology" by the American Society for Bacteriology, Washington D.C., USA, 1981.) These media include various carbon sources, nitrogen sources and trace element components. Carbon sources may include carbohydrates such as glucose, lactose, sucrose, fructose, maltose, starch and fiber; fats such as soybean oil, sunflower oil, castor oil and coconut oil; fatty acids such as palmitic acid, stearic acid and linoleic acid; alcohols such as glycerol and ethanol and organic acids such as acetic acid, and these carbon sources may be used alone or in combination, but are not limited thereto. Nitrogen sources may include organic nitrogen sources and urea, such as peptone, yeast extract, gravy, malt extract, corn steep liquor (CSL), and bean flour, and inorganic nitrogen sources such as ammonium sulfate, ammonium chloride, ammonium phosphate, ammonium carbonate, and ammonium nitrate, and these nitrogen sources may be used alone or in combination, but are not limited thereto. The medium may further include potassium dihydrogen phosphate, dipotassium hydrogen phosphate, and corresponding sodium-containing salts as phosphoric acid sources, but is not limited thereto. The medium may also include metals such as magnesium sulfate or iron sulfate, and amino acids, vitamins and suitable precursors may be added.

In addition, in order to maintain aerobic conditions of the collection liquid W, oxygen or a gas including oxygen (e.g., air) may be injected into the collection liquid W. A temperature of the collection liquid W may generally be 20-45° C., specifically 25-40° C.

At least a part of the storage tank 3201 may include a material through which a wave may pass. For example, at least a region of the storage tank 3201 on which the wave is incident or from which the wave is emitted may include a material such as glass. In another embodiment, when the storage tank 3201 includes a material through which the wave may not pass, for example, a metal material, a through hole corresponding to the region on which the wave is incident or from which the wave is emitted may be formed. At this time, the storage tank 3201 may further include a cover portion (not shown) disposed at one side of the through hole. The cover portion (not shown) may include a transparent or translucent material such that the second wave L21 may pass therethrough. For example, the cover portion (not shown) may include a glass or plastic material, and may be formed in a plate shape having flexibility, but may also be manufactured in a film. In another embodiment, the cover portion (not shown) may be formed to fill the inside of the through hole rather than disposed in one side of the through hole.

Meanwhile, the collection unit 3200 may further include a multiple scattering amplifier MS for reflecting at least a part of the waves emitted from the collection liquid W to the collection liquid W to amplify the number of times of multiple scattering in the collection liquid W. For example, the multiple scattering amplifier MS may scatter at least a part of the waves incident to the storage tank 3201 and scattered due to bacteria in the collection liquid W, and then emitted from the storage tank 3201 into the collection liquid W again. The scattered waves may be scattered and emitted again due to the bacteria in the collection liquid W again, and the number of times of multiple scattering in the collection liquid W may increase through this process.

In an embodiment, the multiple scattering amplifier MS may be disposed between the storage tank 3201 and the wave source 3100, and disposed between the storage tank 3201 and the image sensor 3300 to reflect at least a part of waves multiple scattered and emitted from the collection liquid W. In other words, the multiple scattering amplifier MS may allow the waves multiple scattered and emitted from the collection liquid W to reciprocate a space between the collection liquid W and the multiple scattering amplifier MS at least once time. The multiple scattering amplifier MS may include a multiple scattering material, for example, the multiple scattering material may include titanium oxide ($TiO_2$).

In another embodiment, the collection unit 3200 may form a multiple scattering amplification region including the multiple scattering material in at least a part of the storage tank 3201. For example, the multiple scattering amplification region may be formed by coating, with the multiple scattering material, a region corresponding to at least a space in which the collection liquid W is accommodated in the storage tank 3201. However, the technical idea of the present disclosure is not limited thereto, and the multiple scattering amplification region may be disposed in the entire region of the storage tank 3201 except for the wave incidence part and emission part.

Meanwhile, the inhalation flow path 3211 may be disposed on one side of the storage tank 3201 and perform a function of inhaling external air to guide the external air to the collection liquid W, and the exhaust flow path 3212 mat be disposed on the other side of the storage tank 3201 and perform a function of discharging the air of the storage tank 3201 to the outside. As shown in the drawing, the inhalation flow path 3211 may be formed in which one end is immersed in the collection liquid W and the air is capable of directly contacting with the collection liquid W. However, the present disclosure is not limited thereto, and the inhalation flow path 3211 may be formed in any form capable of guiding the external air to the collection liquid W.

Meanwhile, a filter unit 3240 may be installed in the inhalation flow path 3211. The filter unit 3240 may perform a function of filtering a substance having a predetermined size or more included in the external air introduced into the inhalation flow path 3211.

The exhaust flow path 3212 may be disposed at one end of an accommodation space of the storage tank 3201 except for the collection liquid W so as to discharge the air of the storage tank 3201 to the outside. The external air is guided to the collection liquid W through the inhalation flow path 3211, and then the remaining air excluding the collected bacteria is discharged from the collection liquid W, and the exhaust flow path 3212 performs the function of discharging the air to the outside. Although not shown, the collection unit 3200 may connect the exhaust flow path 3212 with a means such as a pneumatic pump or a compressor to discharge the air in the storage tank 3201 to the outside. In addition, by generating a pressure difference of the storage tank 3201 through the above-described process, the collection unit 3200 may inhale the air into the storage tank 3201.

The collection unit 3200 may include a collection liquid flow pipe 3221 for flowing the collection liquid W stored in the outside into the storage tank 3201, and a collection liquid discharge pipe 3222 for discharging the completely detected collection liquid W from the storage tank 3201. The collection liquid flow pipe 3221 and the collection liquid discharge pipe 3222 may be installed at a lower portion of the storage tank 3201 as illustrated in the drawing to facilitate the introduction and discharge of the collection liquid W.

Meanwhile, the wave source 3100 may irradiate a wave toward the collection liquid W of the collection unit 3200. The wave source 3100 may apply all types of source device capable of generating a wave, and may be, for example, a laser capable of irradiating light of a specific wavelength band. Although the present disclosure is not limited to a type of a wave source, a case where the wave source is the laser will be described for convenience of description.

For example, laser with a good coherence may be used as the wave source 3100 to form speckle in the fluid.

The image sensor 3300 may time serially measure wave speckles generated by multiple scattered in the collection liquid W. In other words, the image sensor 3300 may be disposed on an emission path of the wave, and may time serially capture the waves emitted from the collection liquid W and obtain a plurality of images. The image sensor 3300 may include sensing means corresponding to the type of the wave source 3100. For example, when a light source of a visible light wavelength band is used, a CCD camera which is an image capturing device may be used.

Here, each of the plurality of images may include information of speckles multiple scattered and generated by the bacteria due to the waves incident on the collection liquid W. In other words, the image sensor 3300 may detect the wave speckles generated by the irradiated waves multiple scattered in the collection liquid W, at a preset time. Here, time means any moment in a continuous flow of time, and times may be set in advance at the same time interval, but are not limited thereto, and may be set in advance at any time interval.

The image sensor 3300 may detect a first image including first speckle information at least at a first time and capture a second image including second speckle information at a second time to control the first and second images to the controller 3400. Meanwhile, the first point and the second point are merely one example selected for convenience of description, and the image sensor 3300 may capture a plurality of images at a plurality of points more than the first point and the second point. The image sensor 3300 may include a polarizer 3305 in a path from which waves are emitted, thereby maximizing interference efficiency for speckle formation and removing unnecessary external reflected light, etc.

The controller 3400 may detect the presence of the bacteria, that is, microbes, in the collection liquid W based on a change in the measured wave speckles over time. In an embodiment, the controller 3400 may obtain a temporal correlation of the wave speckles and detect the presence of microbes in the collection liquid W based on the obtained temporal correlation.

Specifically, the controller 3400 may use a difference between first image information of a first wave speckle detected at the first time and second image information of a second wave speckle detected at the second time to detect the presence of the microbe M. Here, the first image information and the second image information may be at least one of pattern information of the wave speckle and intensity information of waves.

Meanwhile, an embodiment of the present disclosure does not use only the difference between the first image information at the first time and the second image information at the second time but may extend this to use image information of a plurality of wave speckles at a plurality of times. The controller 3400 may calculate a temporal correlation coefficient between images using image information of wave speckles generated for a plurality of preset times, and estimate the presence of the microbe M in the collection liquid W and furthermore the presence of the airborne bacteria based on the temporal correlation coefficient.

Referring to FIGS. 16 and 17, the airborne bacteria measuring device 30 according to an embodiment of the present disclosure may further include a sterilization unit 3500.

The sterilization unit 3500 may sterilize the collection liquid W in the storage tank 3201. The sterilization unit 3500 may be any means capable of removing microbes in the collection liquid W. For example, the sterilization unit 3500 may include at least one of an ultraviolet (UV) lamp or a laser having a predetermined or higher output. Alternatively, the sterilization unit 3500 may sterilize using electrolysis. Meanwhile, in another embodiment, the sterilization unit 3500 does not sterilize the collection liquid W in the storage tank 3201, but is disposed on the discharge path of the collection liquid discharge pipe 3222 to sterilize the discharged collection liquid W.

Meanwhile, the airborne bacteria measuring device 30 may further include a first valve 3231 installed in the collection liquid flow pipe 3221 and selectively opening and closing the collection liquid flow pipe 3221 and a second valve 3232 installed in the collection liquid discharge pipe 3222 and selectively opening and closing the collection liquid discharge pipe 3222. In this case, the controller 3400 may control an operation of the first valve 3231 or the second valve 3232 by a preset program.

Figure 17A:
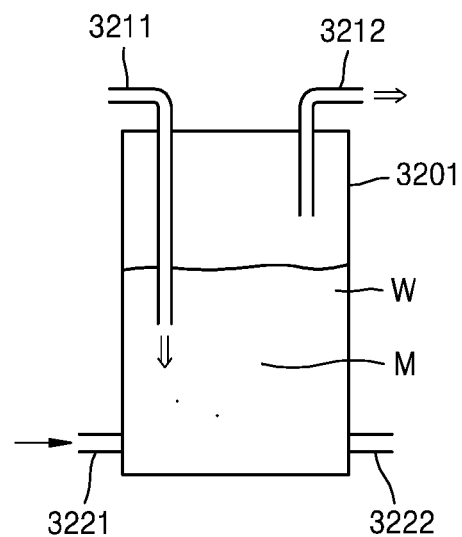
FIGS. 17A to 17D are diagrams for explaining a process performed by the airborne bacteria measuring device of FIG. 14 of sampling bacteria and then processing a collection liquid.

Specifically, referring to FIG. 17A, the airborne bacteria measuring device 30 may collect airborne bacteria M in the collection liquid W using the collection unit 3200. As described above, the airborne bacteria measuring device 30 may introduce the managed collection liquid W into the storage tank 3201 immediately before detection such that the collection liquid W does not include a microbe before inhaling the microbe M or previously measure the collection liquid W accommodated in the storage tank 3201 to store concentration of impurities including the microbes. When the collection liquid W stored outside is introduced into the storage tank 3201, the controller 3400 may control the first valve 3231 to be opened, after accommodating a predetermined amount of the collection liquid W, control the first valve 3231 to be closed. Thereafter, the airborne bacteria measuring device 30 may collect the bacteria M included in the external air by contacting the inhaled external air with the collection liquid W.

Figure 17B:
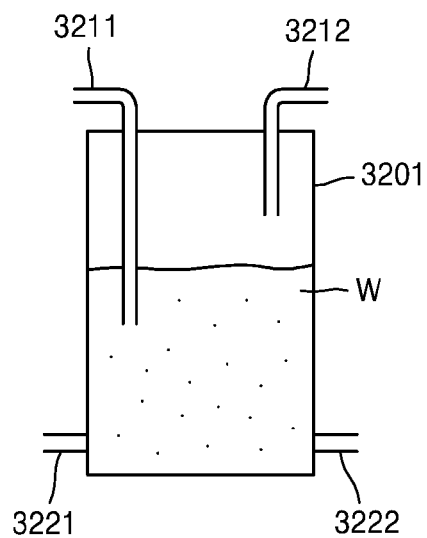
Figure 17C:
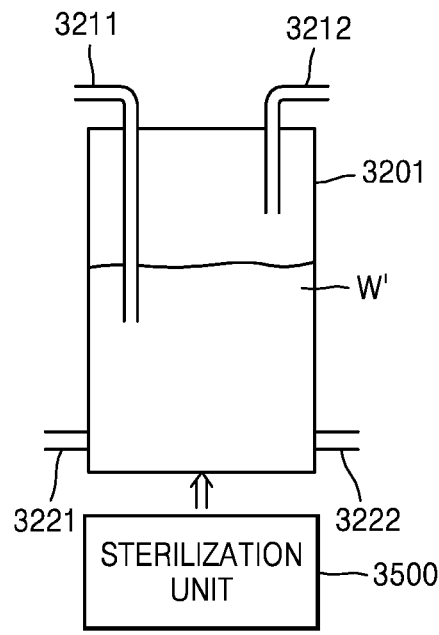

Referring to FIG. 17B, the airborne bacteria measuring device 30 may detect the presence or concentration of the microbe M in real time by irradiating waves in the collection liquid W, but in another embodiment, may culture the microbe M in the collection liquid W for a certain period of time and then detect the microbe M. When culturing the microbe M in the collection liquid W for a certain period of time and then measuring the microbe M, the airborne bacteria measuring device 30 may estimate an actual concentration of the airborne bacteria from the concentration of the microbe M detected in consideration of the above period of time.

Referring to FIG. 17B, the completely detected collection liquid W as described above may be sterilized by the sterilization unit 3500. Through this, the airborne bacteria measuring device 30 may not only minimize the generation of contaminants by sterilizing and then discharging the collection liquid W but also more ultimately increasing the accuracy of a repetitive detection process by removing microbes in the storage tank 3201.

Figure 17D:
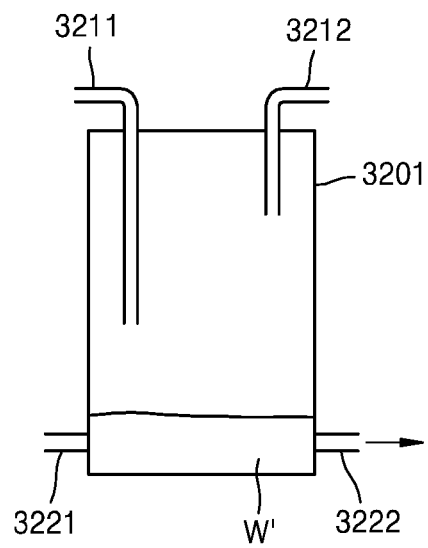

Referring to FIG. 17D, when the sterilization process is completed, the controller 3400 may control the second valve 3322 to be opened to discharge the collection liquid W in the storage tank 3201 to the outside. By repeating the above process, the airborne bacteria measuring device 30 may repeatedly measure the airborne bacteria, such data may be provided to an external server to be utilized as big data.

Hereinafter, a network environment including the airborne bacteria measuring device 30 having the above-described configuration will be described with reference to the drawings. In this regard, a method of identifying concentration or type of airborne bacteria as well as detecting the airborne bacteria through machine learning will be described.

Figure 18:
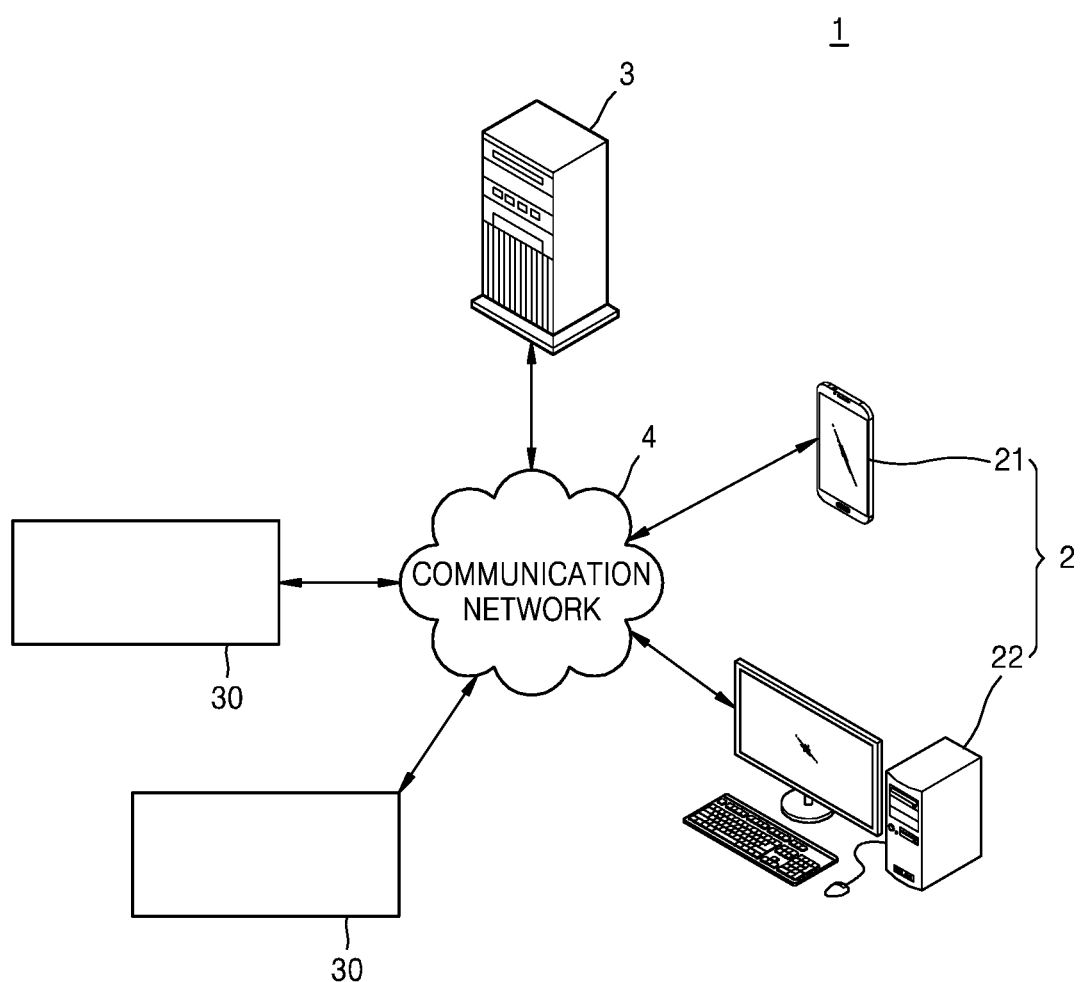
FIG. 18 is a diagram showing an example of a network environment according to an embodiment of the present disclosure.

FIG. 18 is a diagram showing an example of a network environment 1 according to an embodiment of the present disclosure.

The network environment 1 of FIG. 18 shows the example including one or more airborne bacteria measuring devices 30, a user terminal 2, a server 3, and a network 4. FIG. 18 is an example for describing the present disclosure, and the number of terminals of a user and the number of servers is not limited to that in FIG. 18.

The one or more airborne bacteria measuring devices 30 may be provided and disposed in different regions to detect airborne bacteria in each region through the above-described detection process. The airborne bacteria measuring device 30 may be provided to the server 3 or the user terminal 2 using the network 4 which is the communication network.

Using data provided in this way, the server 3 may generate airborne bacteria information according to a region, and more specifically, anti-bacterial information related to the bacteria, with a map and provide the same to the user terminal 2.

The user terminal 2 may be a fixed terminal 22 implemented as a computer device or a mobile terminal 21. The user terminal 2 may be a terminal of an administrator controlling the server 3. Examples of the user terminal 2 include a smart phone, a mobile phone, a navigation device, a computer, a notebook computer, a digital broadcasting terminal, a personal digital assistant (PDA), a portable multimedia player (PMP), a tablet PC, and the like. For example, the user terminal 1 21 may communicate with another user terminal 22 and/or the server 3 through the communication network 4 using a wireless or wired communication method.

The communication method is not limited and may include not only a communication method using a communication network (e.g., a mobile communication network, a wired internet, a wireless internet, and a broadcasting network) that the network 4 may include, but also a short range wireless communication between devices. For example, the network 4 may include any one or more of networks among a personal area network (PAN), a local area network (LAN), a campus area network (CAN), a metropolitan area network (MAN), a wide area network (WAN), a broadband network (BBN), and the Internet. The network 4 may also include any one or more of network topologies, including bus networks, star networks, ring networks, mesh networks, star-bus networks, tree or hierarchical networks but is not limited thereto.

The server 3 may communicate with the user terminal 2 or the airborne bacteria measuring device 30 through the network 4 to be implemented as a computer device or a plurality of computer devices providing command, code, file, content, service, etc.

The airborne bacteria measuring device 30 according to an embodiment of the present disclosure may perform a function of collecting the airborne bacteria through an independent configuration, measuring wave speckles emitted from a collection liquid, learning a microbial classification criteria using the wave speckles by the controller 3400, and detecting bacteria in the collection liquid using the learned microbial classification criteria.

However, the technical idea of the present disclosure is not limited thereto, the airborne bacteria measuring device 30 may transmit detection data to the external server 3, and the external server 3 may use the transmitted data to machine learn the microbial classification criteria and provide a learned algorithm to the airborne bacteria measuring device 30. The airborne bacteria measuring device 30 may detect the presence of airborne bacteria or identify the concentration or the type of the airborne bacteria using the provided algorithm and data about newly measured wave speckles. Hereinafter, for convenience of explanation, the case where the server 3 machine learns the microbial classification criteria will be mainly described.

Figure 19:
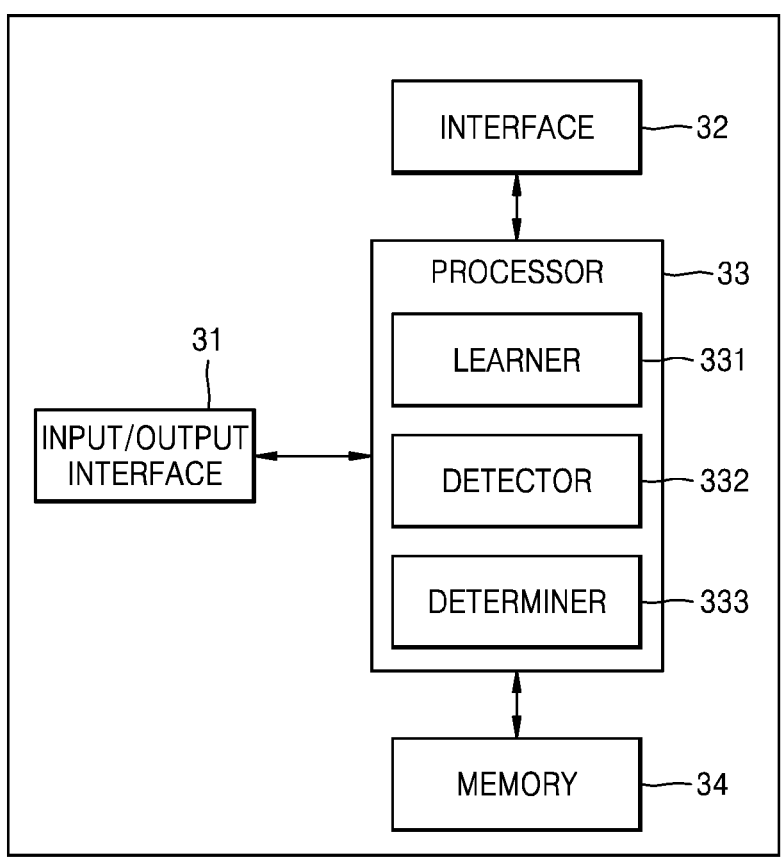
FIG. 19 is a block diagram schematically showing a server according to an embodiment of the present disclosure.

FIG. 19 is a block diagram schematically showing the server 3 according to an embodiment of the present disclosure.

The server 3 may correspond to at least one processor or may include at least one processor. Accordingly, the server 3 may be driven by included in a hardware device such as a microprocessor or a general purpose computer system. Here, the 'processor' may refer to, for example, a data processing unit embedded in hardware and including a circuit physically structured to perform a function represented in codes or commands included in a program. An example of the data processing unit embedded in the hardware may include a processing device such as a microprocessor, a central processing unit (CPU), a processor core, a multiprocessor, application-specific integrated circuit (ASIC), field programmable gate array (FPGA), and the like, but the scope of the present disclosure is not limited thereto.

The server 3 shown in FIG. 19 shows only the components related to the present embodiment in order to prevent the features of the present embodiment from being blurred. Accordingly, it will be understood by those skilled in the art that other general purpose components may be further included in addition to the components illustrated in FIG. 19.

Referring to FIG. 19, the server 3 according to an embodiment of the present disclosure may include an input/output interface 31, a receiver 32, a processor 33, and a memory 34.

The memory 34 is a computer readable recording medium, and may include a permanent mass storage device such as random access memory (RAM), read only memory (ROM), and a disk drive.

The input/output interface 31 may be means for interfacing with input/output devices. For example, the input device may include a device such as a keyboard or mouse, and the output device may include a device such as a display for displaying a communication session of an application. As another example, the input/output interface 31 may be means for interfacing with a device such as a touch screen in which functions for input and output are integrated into one.

The receiver 32 may receive a plurality of images from the airborne bacteria measuring device 30. At this time, the plurality of images may be images obtained by the image sensor 3300 of the airborne bacteria measuring device 30 by capturing waves emitted from the collection liquid W in the time series order. That is, the receiver 32 may function as a communication module using wired or wireless communication, and may receive the plurality of images. At this time, the receiver 32 may provide a function for the user terminal 1 21 and the server 3 to communicate with each other over the network 4, and may provide a function for communicating with another user terminal (e.g., the user terminal 2 22) or another server.

The processor 33 may be configured to process commands of a computer program by performing basic arithmetic, logic, and input/output operations. The command may be provided to the processor 33 by the memory 34 or the receiver 32. For example, the processor 33 may be configured to execute a command received according to a program code stored in a recording device such as the memory 34. The processor 33 may include a learner 331, a detector 332, and a determiner 333.

The detector 322 may extract a feature of change over time from a plurality of learning images received by the receiver 32. Here, the plurality of learning images are images continuously captured at a time interval, and include time information between the plurality of learning images captured in the time series order. The detector 322 may extract the feature of change over time from the plurality of learning images.

The learner 331 may learn the microbial classification criteria for identifying the type or the concentration of microbes present in the collection liquid W based on the extracted feature. The learner 331 learns the microbial classification criteria based on deep learning, and deep learning is defined as a set of machine learning algorithms that attempt high level abstractions (a job of summarizing core content or function in a large amount of data or complex data) through a combination of several non-linear transformation methods. The learner 331 may use any one of models of deep learning, for example, deep neural networks (DNNs), convolutional neural networks (CNNs), recurrent neural networks (RNNs), and deep belief networks (DBNs).

In an embodiment, the learner 331 may machine learn a classification criterion based on temporal correlation of the received plurality of learning images.

As described above, the plurality of learning images may include information of wave speckles multiple scattered and generated from the microbe M in the collection liquid W. As described above with reference to FIG. 3, when bacteria are present in the collection liquid W, a speckle may change over time due to the life activity of microbes. In addition, because a change of the speckle over time is different according to the type or the concentration of the microbe, the learner 331 may learn the microbial classification criteria for classifying the type or concentration of the microbe using the change of the speckle over time.

Figure 20:
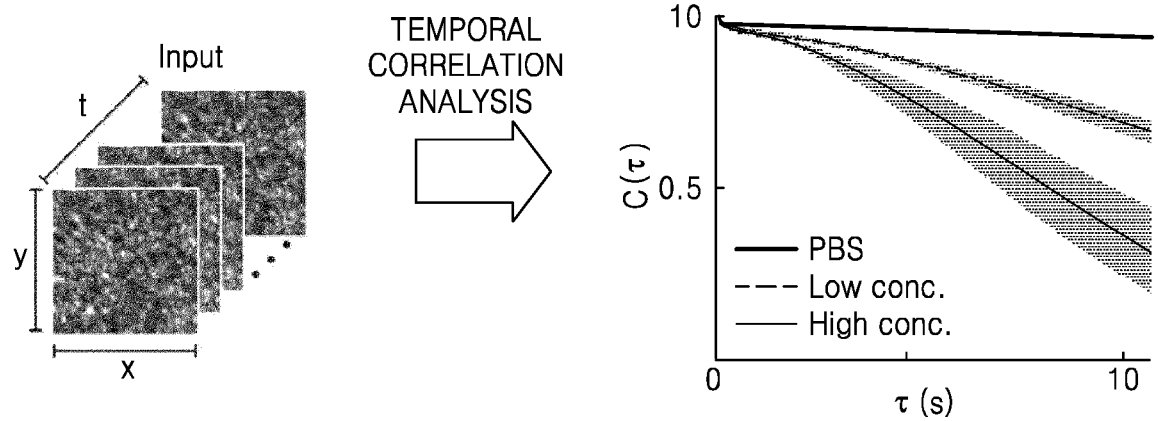
FIG. 20 is a diagram for describing a method, performed by a learner, of analyzing a temporal correlation of speckles according to an embodiment of the present disclosure.

FIG. 20 is a diagram for describing a method, performed by the learner 331, of analyzing a temporal correlation of speckles according to an embodiment of the present disclosure.

Referring to FIG. 20, the learner 331 may calculate temporal correlation coefficients between images as shown in Equation 3 by using image information of speckles generated at a plurality of preset times, and may learn a microbial classification criteria based on the temporal correlation coefficients. As shown in FIG. 20, as the concentration of microbe increases, a time that the temporal correlation coefficients fall below a reference value decreases. Using this, the concentration of the microbe may be analyzed through inclination values of a graph representing the temporal correlation coefficients. The learner 331 may learn the microbial classification criteria for identifying the concentration of the microbe by analyzing the inclination values of the temporal correlation coefficients.

Figure 21:
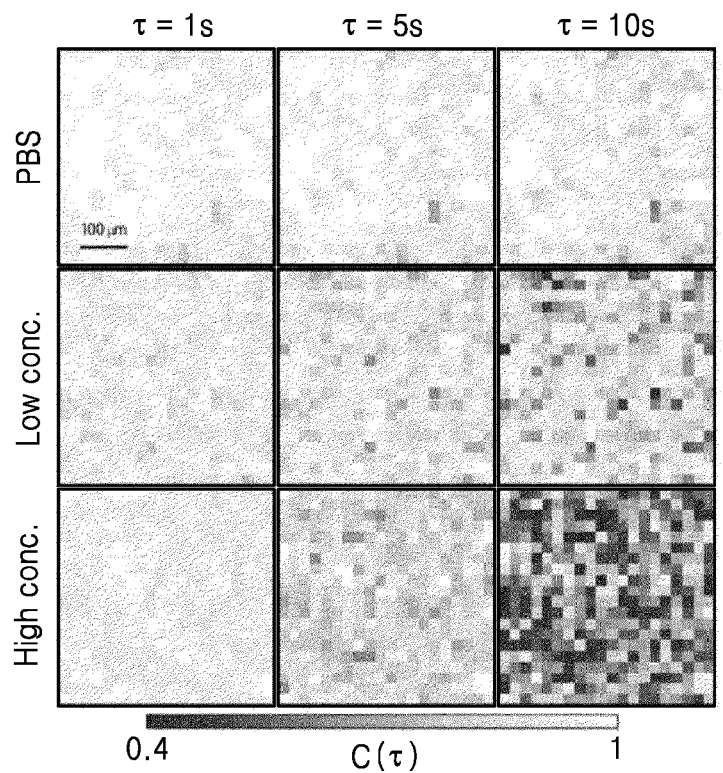
FIG. 21 is a diagram showing a standard deviation distribution of the light intensity of wave speckles measured over time.

FIG. 21 is a diagram showing a standard deviation distribution of the light intensity of wave speckles measured over time.

Referring to FIG. 21, the learner 331 may calculate a standard deviation of the light intensity of speckle patterns using a plurality of learning images measured for each reference time. As germs and microbes present in a sample continuously move, constructive interference and destructive interference may change in response to the movement. At this time, as the constructive interference and the destructive interference change, a degree of light intensity may change. The learner 331 may calculate the standard deviation indicating the degree of change of the light intensity, analyze locations of the germs and the microbes in the sample, and learn the distribution of the germs and the microbes.

For example, the learner 331 may calculate the standard deviation of the light intensity of the speckle pattern detected in each of the plurality of learning images over time. The standard deviation of the light intensity of the speckle over time may be calculated based on Equation 6 described above.

Because constructive and destructive interference change according to movements of germs and microbes, and a value of the standard deviation calculated based on Equation 6 is different, concentrations of germs and microbes may be measured based on this. The learner 331 may learn the classification criteria based on the linear relationship between the magnitude of the standard deviation value of the light intensity of the speckle pattern and the concentrations of germs and microbes.

Hereinafter, the case where the learner 331 learns the classification criteria using a CNN will be mainly described.

Here, the CNN is a type of multilayer perceptrons designed to use minimal prepocessing. The CNN may include a convolutional layer that performs convolution on input data, and may further include a subsampling layer that performs subsampling on an image to extract a feature map from the corresponding data. Here, the subsampling layer is a layer that increases the contrast between neighboring data and reduces an amount of data to be processed and may use max pooling, average pooling, etc.

Figure 22:
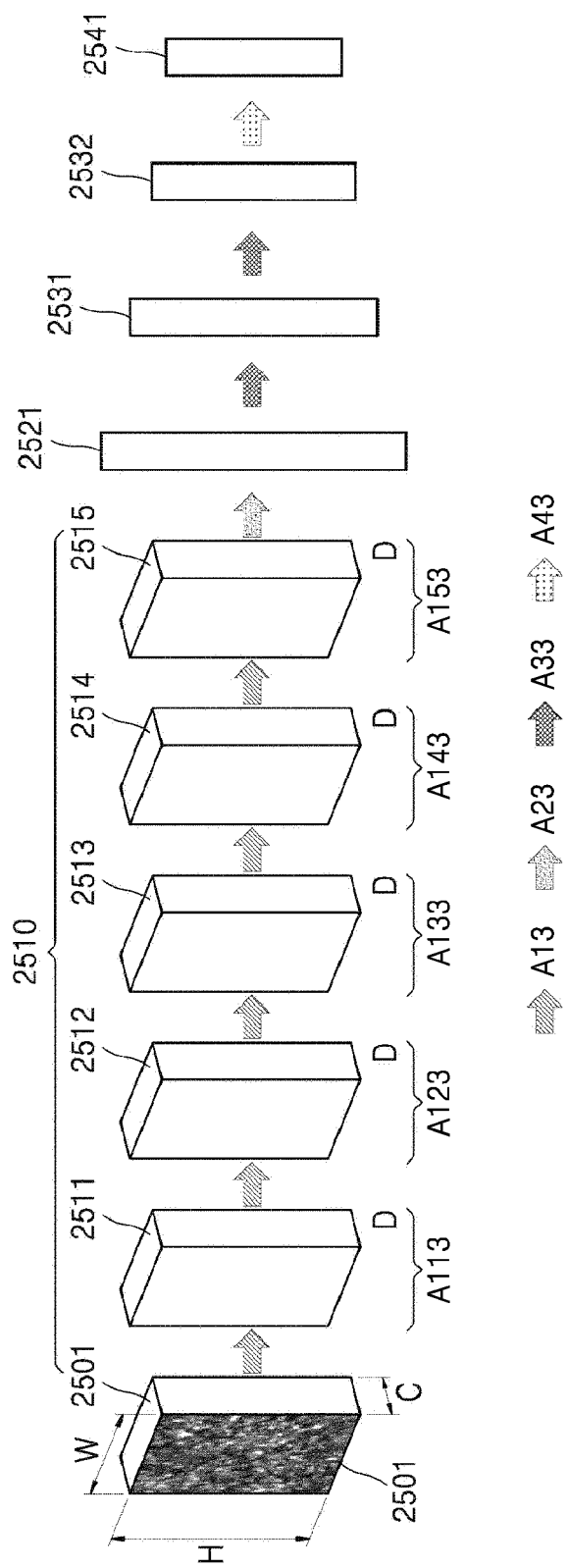
FIG. 22 is a diagram showing a convolutional neural network (CNN) according to an embodiment of the present disclosure.
Figure 23:
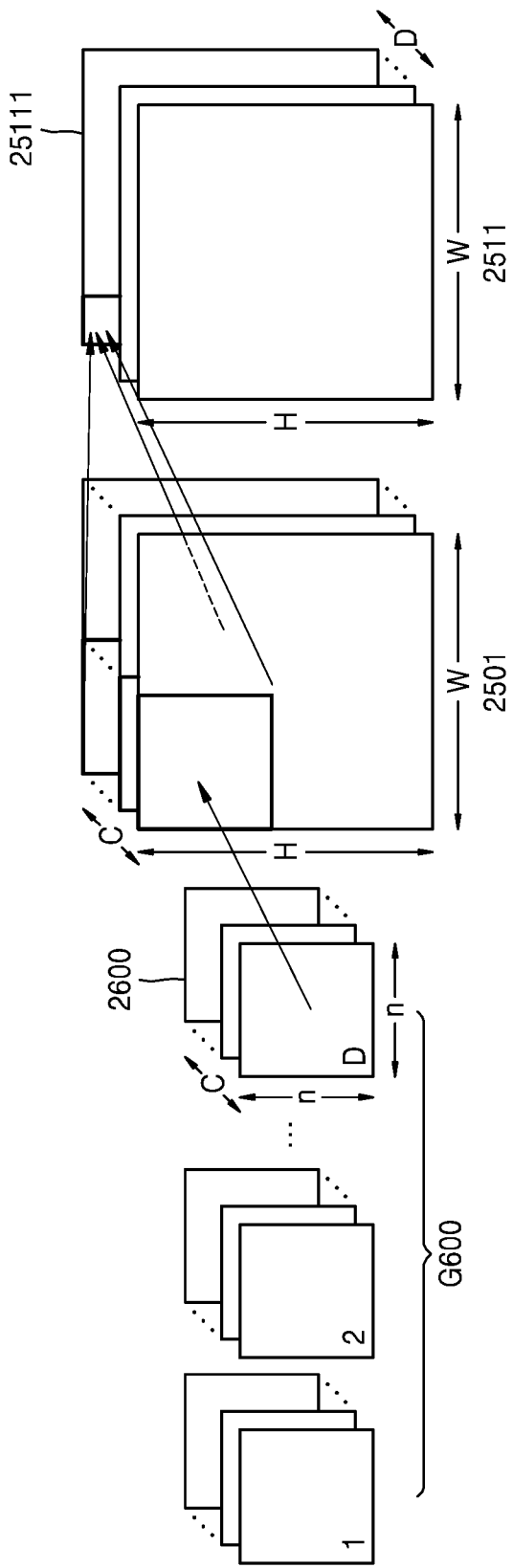
FIGS. 23 and 24 are diagrams for describing a convolution operation of FIG.
Figure 24:
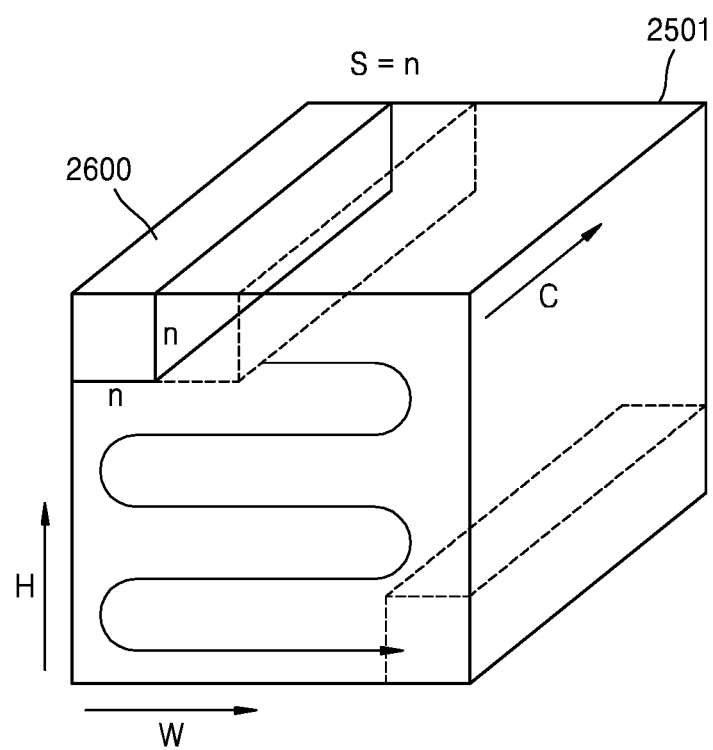

FIG. 22 is a diagram showing a CNN 2510 according to an embodiment of the present disclosure, and FIGS. 23 and 24 are diagrams for describing a convolution operation of FIG. 22.

Referring to FIGS. 22 to 24, the CNN 2510 according to an embodiment of the present disclosure used by the learner 331 may include a plurality of convolutional layers A1. The learner 331 may generate an output by performing the convolution operation between kernels and inputs of the convolution layers.

The input of the convolutional layer is data employed as an input of the corresponding convolutional layer and includes at least one input feature map corresponding to initial input data or an output generated by a previous layer. For example, an input of the convolutional layer 1 A113 shown in FIG. 8 may be a plurality of images 2501 which are initial inputs of the CNN 2510, and an input of a convolutional layer 2 A123 may be an output 2511 of the convolutional layer 1 A113.

The input 2501 of the CNN 2510 is the plurality of C images 2501 received by the receiver 32, and a temporal correlation may be established between images that are input feature maps. Each image, that is, each input feature map may have a plurality of pixels including previously set width W and height H. Because there are C input feature maps, the size of the input 2501 may be expressed as W×H×C. The learner 331 may perform the convolution operation corresponding to the input 2501 by using one kernel corresponding to a convolution layer A1.

At least one kernel of a convolutional layer A13 is data employed for the convolution operation corresponding to the corresponding convolutional layer A1, and may be defined based on, for example, an input and an output of the corresponding convolutional layer. At least one kernel may be designed for each convolutional layer A13 constituting the CNN 2510. At least one kernel corresponding to each convolutional layer may be referred to as a kernel set G600.

Here, the kernel set G600 may include kernels corresponding to output channels D. For example, in order to obtain a desired output of the convolutional layer A13, the kernel set G600 of the corresponding convolutional layer may be defined such that an input and a convolution operation of the corresponding convolutional layer are performed. The output of the convolutional layer A13 is data based on a result of the convolution operation between the input of the corresponding convolutional layer and the kernel set, and may include at least one output feature map and be employed as an input of a next layer.

The learner 331 may generate an output 2511 by performing the convolution operation between the kernel set G600 corresponding to the convolution layer A13 and the input 2501. The output 2511 of the convolutional layer A13 may include output feature maps 25111 corresponding to the D output channels, and the size of each output feature map 25111 may be W×H. Here, the width, height, and number (depth) of the output 2511 are W, H, and D, respectively, and the size of the output 2511 may be expressed as W×H×D.

For example, the kernel set G600 corresponding to the convolutional layer A1 may include convolutional kernels corresponding to the D output channels. The learner 331 may generate the output feature maps 25111 corresponding to the D output channels based on operation results between the input 2501 and the kernels corresponding to the D output channels.

The learner 331 may include the plurality of convolution layers A13, and in an embodiment, may include the 4 to 7 convolution layers A13. For example, as shown in the figure, the learner 331 may include 5 convolution layers A113, A123, A133, A143, and A153. Through the plurality of convolution layers A113, A123, A133, A143, and A153, the learner 331 may increase a learning capacity that may imply a complex non-linear relationship. However, the present disclosure is not limited thereto, and the more convolutional layers A13 may be used to learn.

Meanwhile, each of the convolution layers A13 may include an activation function. The activation function may be applied with respect to layers of each layer to perform a function that allows respective inputs to have a complex non-linear relationship. The activation function may use a sigmoid function, a tanh function, a rectified linear unit (ReLU), a leaky ReLU, etc., which may convert an input into a normalized output.

The learner 331 according to an embodiment of the present disclosure may completely initialize the kernels by using values of −1 to 1 during first learning using the CNN 2510. In the case of using the activation function that outputs all of data having a negative value as 0, output values including valid information may not be transferred to a next convolution layer, which may reduce learning efficiency. Therefore, in an embodiment of the present disclosure, the learner 331 may add a leaky ReLU layer after the convolutional layer A13 and output a positive value as it is, but may output input data of a negative value to have a constant inclination. Through this, the learner 331 may prevent the convergence speed degradation and local minimization problems while learning.

The input 2501 may be a set of input feature maps to which padding is applied, wherein padding refers to a technique of filling a partial region of an input with a specific value. Specifically, applying padding to the input with the pad size of 1 means an operation of filling an edge of the input feature map with the specific value and zero padding refers to setting the specific value to 0. For example, when zero padding with the pad size of 1 is applied to the size input of X×Y×Z, the input to which padding is applied is data in which the edge is 0 and the size is ((X+1)×(Y+1)×Z and may include (X+1)×(Y+1)×Z input elements.

Meanwhile, the learner 331 learns using temporal correlations of a plurality of images in performing the convolution operation with the plurality of images including speckle information as input. At this time, each image may include a plurality of speckles that are grain shape patterns. At this time, the learner 331 may learn the classification criteria based on a temporal correlation of each speckle. In other words, the learner 331 learns the classification criteria using three-dimensional information including information of time other than two-dimensional information of an image.

The learner 331 should concentrate on information about one speckle, and in order to accurately obtain three-dimensional information about one speckle, should learn the classification criteria by identifying the one speckle and surrounding speckles. Therefore, the learner 331 may perform the convolution operation using a convolution kernel having a size smaller than that of one speckle. That is, when the size of one speckle corresponds to m pixels, the learner 331 performs the convolution operation using a convolution kernel of a size of n×n smaller than m. In an embodiment, as described above, because the image sensor 3300 is arranged such that at most 5 pixels are located in a speckle grain size, m may be 5, where n may have a value of 1. That is, the learner 331 may perform the convolution operation using a 1×1 convolution kernel. However, the technical idea of the present disclosure is to perform the convolution operation using a kernel having a size smaller than that of a speckle, but the present disclosure is not limited thereto.

The kernel set G600 may include convolution kernels corresponding to the D output channels, and each convolution kernel may include kernel feature maps corresponding to a plurality of image number. Because the size of each kernel feature map is n×n, the kernel set G600 includes n×n×C×D kernel elements. Here, the size of the convolution kernel is n×n×C, where C may be the number of a plurality of images, that is, the number of image frames. The number of convolution kernels may be equal to the number C of the plurality of images. In this case, the number of convolution kernels may be used for Fourier transformation of the same condition or analysis using Fourier transformation using an output result of each layer.

As shown in FIG. 21, the learner 331 may perform an operation between a convolution kernel corresponding to a first output channel of the kernel set G600 and the input 2501 to generate the output feature map 25111 corresponding to the first output channel. In this way, the learner 331 may generate the output feature maps 25111 corresponding to the D output channels by performing operations between the D kernels of the kernel set G600 and the input 2501 and generate an output 252511 including the generated output feature maps 25111.

For example, the learner 331 may perform an operation between a convolution kernel 600 corresponding to a D-th output channel having the size of n×n× C and the input 501 having the size of W×H×C to generate the output feature map 25111 of the size of W×H, and the generated output feature map 25111 corresponds to the D-th output channel. Specifically, the convolution kernel 600 corresponding to the D-th output channel includes C kernel feature maps, and the size of each kernel feature map is n×n. The learner 331 may slide each kernel feature map having the size of n×n on each input feature map having the size of W×H included in the input 501 by a specific stride to generate the output feature map 25111 that is the operation result between the convolution kernel 2600 correspond to the D-th output channel and the input 2501.

Here, the stride means an interval for sliding the kernel feature map during the convolution operation. As described above, in order to concentrate on the information about one speckle, because the learner 331 needs to learn the classification criteria by identifying the one speckle and the surrounding speckles, the slid s that is the sliding interval may have a value corresponding to the size of the convolution kernel such that each convolution kernel and its corresponding region do not overlap. In other words, when using the convolution kernel of the size n×n, the stride s may have a value of n. For example, in the case of the 1×1 convolution kernel, the stride s may be 1. Through this, the learner 331 may learn the classification criteria based on only the time information of one speckle by non-overlapping one speckle and other surrounding speckles.

In an embodiment, the learner 331 may perform the convolution operation to have the same output channel number D as the plurality of image number C in learning the classification criteria using the CNN 2510. In other words, the kernel set G600 may include D convolution kernels including C kernel feature maps, where C and D may be the same.

Meanwhile, the learner 331 may reduce the size of the output 2515 using a pooling operation after the convolution operation using the convolution layers A1. For example, the learner 331 may reduce the size of the output 2515 using subsampling A2. For example, the subsampling may be global average pooling which is an operation of setting an average value within a range of a predetermined size as a representative of the range. However, the present disclosure is not limited thereto, and may use max pooling, min pooling, etc.

Thereafter, the learner 331 may obtain a final output 2541 by applying a predetermined operation and a weight to the feature maps 2521 extracted through a filter of the subsampling A23, using a fully connected layer. For example, the learner 331 may further apply A33 a leaky reLU to the fully connected layer after performing the subsampling A23, and then obtain the final output by applying A43 a softmax layer to the fully connected layer. Here, the final output 2541 may be microbial classification criteria for identifying a type or a concentration of microbe by the temporal correlation of the speckle.

Thereafter, the server 3 may receive an image related to a wave speckle obtained by irradiating a wave to the new collection liquid W from the airborne bacteria measuring device 30, and the determiner 333 may identify a type or a concentration of bacteria included in the new collection liquid W based on the obtained microbial classification criteria. However, the determiner 333 does not necessarily need to be included in the server 3, and when the microbial classification criteria learned from the server 3 is provided to the controller 3400 of the airborne bacteria measuring device 30, the controller 340 may identify the type or the concentration of bacteria included in the new collection liquid W based on the microbial classification criteria, like a function of the determiner 333.

FIG. 25 is a graph comparing predicted microbe information (prediction) obtained by measuring airborne bacteria through machine learning according to an embodiment of the present disclosure and actual microbe information (ground truth).

Referring to FIG. 25, it may be seen that a matching rate between the predicted microbe information obtained through an airborne bacteria measuring technology according to an embodiment of the present disclosure and the actual microbe information is very high. It may be confirmed through a result of FIG. 25 that the airborne bacteria measuring device 30 may use microbial classification criteria to identify a type (*B. subtilis, E. Coli, P. aeruginosa, S. aureus*) of microbe included in the collection liquid W, etc., as well as identify each concentration.

As described above, the airborne bacteria measuring device according to the embodiments of the present disclosure may collect airborne bacteria in a collection liquid, and then detect the presence of microbe in the collection liquid using a wave speckle, thereby detecting the airborne bacteria quickly and accurately without a separate chemical method. In addition, the airborne bacteria measuring device may obtain the classification criteria for classifying types or concentrations of microbes using a change in a temporal correlation of a speckle through machine learning, thereby quickly and accurately identifying a type or a concentration of the airborne bacteria. Through this, it is possible to identify the presence of pathogens in the air within a region, and effectively determine regional prevention information through a network environment.

Figure 26:
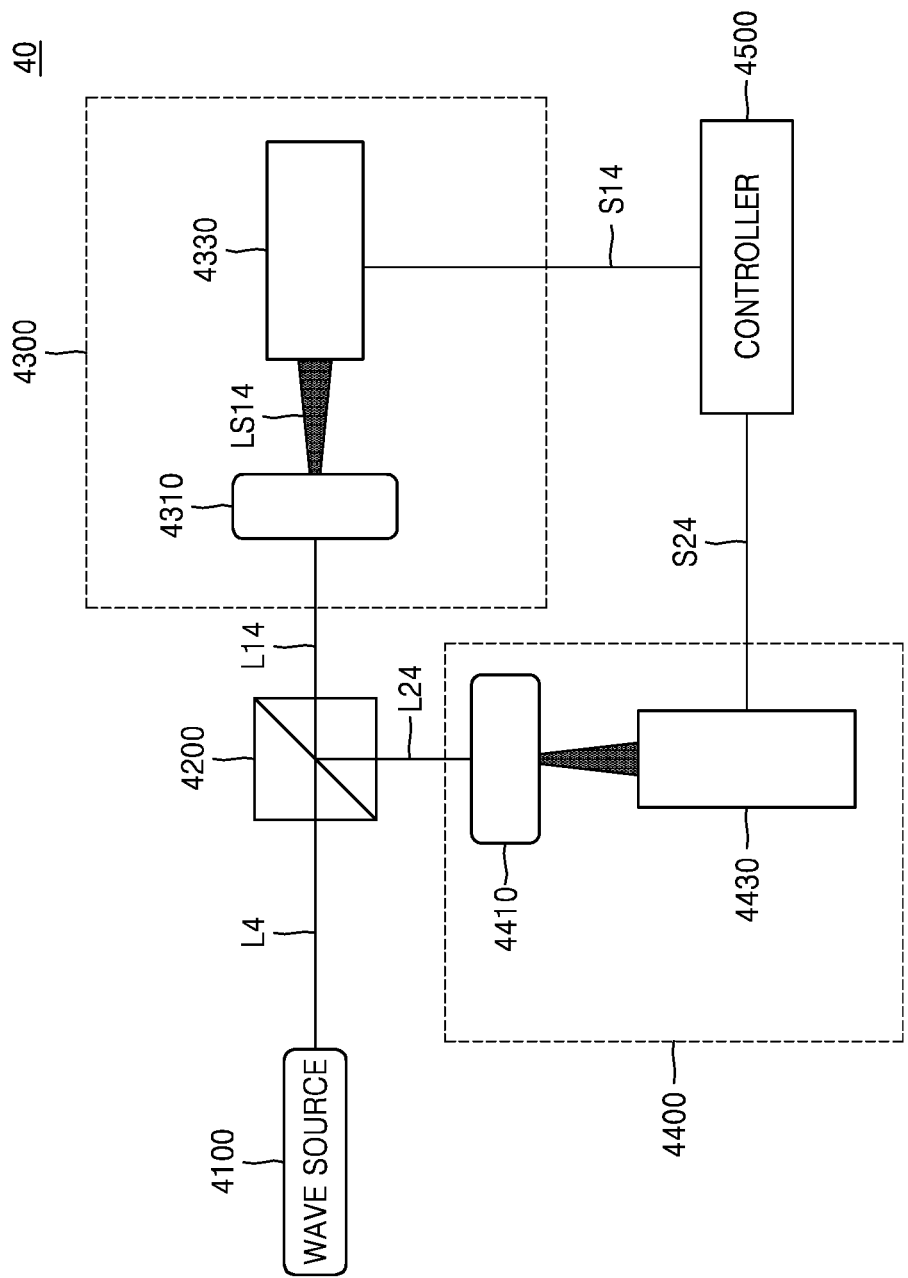
FIG. 26 is a diagram schematically showing an optical detection system according to an embodiment of the present disclosure.
Figure 27:
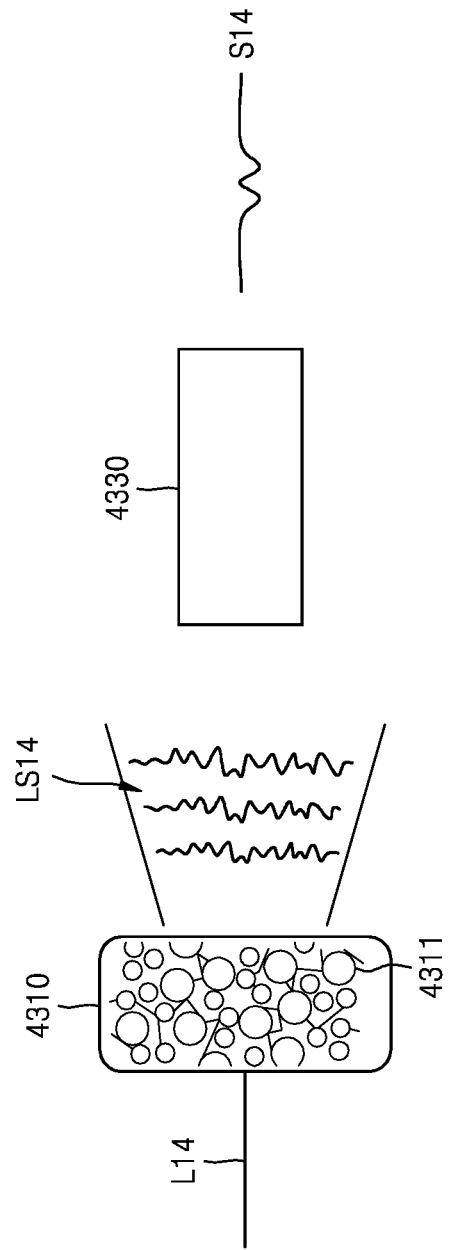
FIG. 27 is a diagram for explaining a process, performed by a first speckle generation unit of generating a first speckle.
Figure 28:
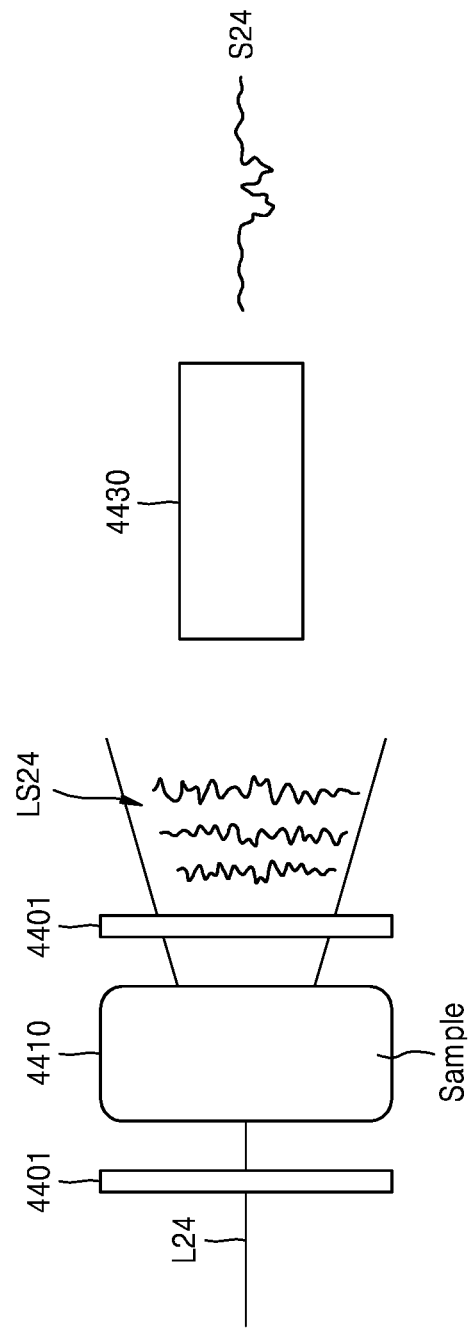
FIG. 28 is a diagram for explaining a process, performed by a second speckle generation unit of generating a second speckle.

FIG. 26 is a diagram schematically showing an optical detection system 40 according to an embodiment of the present disclosure, FIG. 27 is a diagram for explaining a process, performed by a first speckle generation unit 4310 of generating a first speckle LS14, and FIG. 28 is a diagram for explaining a process, performed by a second speckle generation unit 4410 of generating a second speckle LS24.

Referring to FIG. 26, the optical detection system 40 according to an embodiment of the present disclosure may include a wave source 4100, an optical unit 4200, a first speckle generator 4300, a sample measurer 4400, and a controller 4500.

The wave source 4100 may generate a wave L4. The wave source 4100 may apply all types of source device capable of generating a wave L, and may be, for example, a laser capable of irradiating light of a specific wavelength band. Although the present disclosure is not limited to a type of a wave source, a case where the wave source is the laser will be described for convenience of description.

For example, laser with a good coherence may be used as the wave source 4100 to form speckle in a sample to be measured. In this case, the shorter the spectral bandwidth of the wave source that determines the coherence of the laser wave source, the greater the measurement accuracy. That is, the longer the coherence length, the greater the measurement accuracy. Accordingly, a laser light whose spectral bandwidth of the wave source is less than a predetermined reference bandwidth may be used as the wave source 1200, and the measurement accuracy may increase as the spectral bandwidth of the wave source is shorter than the reference bandwidth.

However, in an actual measurement environment, various environmental variables such as temperature exist, and properties of the wave L4 generated from the wave source 4100 may change due to minute vibrations or external factors. As an example, a wavelength of the wave L4 may change by an ambient temperature. The change in the wave L4 may cause a change in the measurement data output from the sample. In particular, as in the present disclosure, when a change of speckle over time is detected and is used to detect a minute life activity of microbe, it must be sensitive to even a small change in the wave L4.

The technical idea of the present disclosure is to accurately detect the property change in the wave L4 due to external environmental factors, to measure only when it is stable using detection results, or to correct measurement data, thereby improving the accuracy of microbe detection.

To this end, embodiments of the present disclosure may provide the one wave L4 generated from the wave source 4100 by changing a path of the wave L4 to a first path or a second path by using the optical unit 4200 or by splitting the wave L4 into a first wave L14 and a second wave L24.

At this time, the optical detection system 40 merely splits the first wave L14 and the second wave L24 by the optical unit 4200 or changes paths but provides the same environmental condition, and thus the properties of the first wave L14 and the second wave L24 are the same. The first wave L14 may be used as an incident wave for generating a reference signal, and the second wave L24 may be used as an incident wave for generating a measurement signal.

The optical unit 4200 may include one or more optical elements to perform a function of transferring the wave L4 generated by the wave source 4100 to the first path or the second path. In an embodiment, the optical unit 4200 may include an optical path changing means for providing the wave L4 to the first path and then changing the wave L4 to the second path. In this case, as the optical path changing means, a generally known micro electromechanical system (MEMS) mirror, a digital micromirror device (DMD) element, or the like may be employed. In another embodiment, the optical unit 4200 may include an optical element that performs a function of splitting into the first wave L14 and the second wave L24. As shown in the drawing, the optical unit 4200 may include a beam splitter that splits the incident wave L4 into the first wave L14 and the second wave L24 to the first path and the second path which are different paths. However, the present disclosure is not limited thereto.

In another embodiment, the optical unit 4200 may further include a multiple beam reflector. The multiple beam reflector may split the wave incident from the wave source 4100 to provide the wave to a plurality of wave paths. The multiple beam reflector may reflect waves at front and rear surfaces to provide the parallel and split first wave L14 and second wave L24. At this time, the beam splitter may be disposed on the plurality of wave paths provided from the multiple beam reflector and provide the first wave L14 and the second wave L24 to the first speckle generation unit 4310 and the sample measurer 4400, more specifically, the second speckle generation unit 4410, respectively.

In addition, the optical unit 4200 may further include a mirror for changing the wave path provided from the wave source 4100.

Hereinafter, for convenience of description, the case where the optical unit 4200 splits and provides the wave L4 into the first wave L14 and the second wave L24 will be mainly described.

Referring to FIGS. 26 and 27, the first speckle generator 4300 may detect the first speckle LS14 which is a reference signal generated using the first wave L14. The first speckle generator 4300 may include a first speckle generation unit 4310 and a first image sensor 4330.

The first speckle generation unit 4310 may be disposed on a path of the first wave L14. The first speckle generation unit 4310 may include a static scattering medium 311 to scatter the first wave L14 when the first wave L14 is incident and generate the first speckle LS14. As shown in FIG. 27, the scattering medium 311 included in the first speckle generation unit 4310 may include scattering materials disposed in a spatially uniform position. The scattering materials may be arranged without limitations on the intervals spaced apart from each other or positions, but maintain a static state without moving in an arrangement state. At this time, there is no limitation on a type of the scattering material 311, for example, titanium oxide ($TiO_2$) may be used as the scattering material.

When the first wave L14 is incident on the first speckle generation unit 4310, the first wave L14 may be multiply scattered by the scattering medium 311 maintaining the static state, and some of the waves scattered in a complicated path through multiple scattering may be emitted from the first speckle generation unit 4310. Waves emitted by passing through various points of the first speckle generation unit 4310 cause constructive interference or destructive interference with each other, and the constructive/destructive interferences of the waves generate a pattern (a speckle) in grain shape.

At this time, when the first wave L14 has a uniform characteristic without a change in the property over time, the first speckle LS14 generated by the first speckle generation unit 4310 may also form a uniform pattern or pattern by the static scattering medium 311 over time. However, when the property of the wave L4 generated from the wave source 4100, that is, the first wave L14, changes due to the surrounding environment, the pattern or pattern of the first speckle LS14 changes.

The first image sensor 4330 may be disposed on a path from which the first speckle LS14 is emitted to detect the first speckle LS14 in time series order. The first image sensor 4330 may include sensing means corresponding to the type of the wave source 4100. For example, when a light source of a visible light wavelength band is used, a CCD camera which is an image capturing device may be used. When the first image sensor 4330 is the CCD camera, the first image sensor 4330 may time serially capture the first speckle LS14 and obtain a plurality of images.

Here, each of the plurality of images includes information of first speckles multiple scattered and generated by the scattering medium 311 due to the first wave L14 incident on the first speckle generation unit 4310. In other words, the first image sensor 4330 may detect the first speckles generated by the irradiated first wave L14 multiple scattered in the scattering medium 311 at a preset time. Here, time means any moment in a continuous flow of time, and times may be set in advance at the same time interval, but are not limited thereto, and may be set in advance at any time interval.

The first image sensor 4330 may detect a first image at least at a first time and capture a second image at a second time to control the first and second images to the controller 4500. Meanwhile, the first point and the second point are merely one example selected for convenience of description, and the first image sensor 4330 may capture a plurality of images at a plurality of points more than the first point and the second point.

Meanwhile, referring back to FIGS. 26 and 28, the sample measurer 4400 may detect a measurement signal generated using the second wave L24. Here, the measurement signal may be applicable to any kind of measurement signal that may be generated using the second wave L24. In an embodiment, the measurement signal may be a signal having the same intensity of an emitted wave. In another embodiment, the measurement signal may be a signal including speckle information. In other words, the sample measurer 4400 may detect the second speckle LS24 which is a measurement signal generated using the second wave L24. Hereinafter, for convenience of description, a case where the sample measurer 4400 is a second speckle generation unit for detecting the second speckle LS24 will be mainly described. Same reference numerals are provided to the sample measurer and the second speckle generation unit.

The second speckle generation unit 4400 may include the second speckle generation unit 4410 and a second image sensor 4430. The second speckle generation unit 4410 may be disposed on a path of the second wave L24. The second speckle generation unit 4410 may include a sample to be measured to scatter the incident second wave L24 and generate the second speckle LS24. The sample may be any sample for detecting microbes or impurities. For example, the sample may be a sample such as saliva, blood, or tissue collected from an individual to be measured, or may be a sample such as feces, urine, or dead skin discharged to the outside of the individual. Alternatively, the sample may include an organic sample collected from an individual such as food. Meanwhile, the sample may mean the individual to be measured itself. In other words, when the food is an individual and the presence of microbes are measured without damaging the food, the food itself may be a sample. For example, an individual such as meat packaged for sale may be a sample.

The second speckle generation unit 4410 may accommodate only the sample described above, or may accommodate the sample by including a material for culturing microbes such as an agar plate. Alternatively, the second speckle generation unit 4410 may accommodate a collection means of a sample together. For example, the collecting means may be prepared using a means by which microbes may move such as a tape, a membrane, or the like.

In another embodiment, the second speckle generation unit 4410 may accommodate a sample such as a fluid. At this time, the second speckle generation unit 4410 may be a container for accommodating the fluid, or may be a pipe unit through which the fluid may flow.

Meanwhile, the second speckle generation unit 4410 may include a multiple scattering amplification region for amplifying the number of times an incident second wave is multiply scattered in the sample. For example, the multiple scattering amplification region may be formed by including a multiple scattering material in a partial region on which the second wave is incident and a partial region from which the second wave is emitted. For example, the multiple scattering material may include titanium oxide (TiO$_2$), and may be formed by coating a partial region of the second speckle generation unit 4410 on the partial region on or from which the second wave is incident or emitted. The multiple scattering amplification region may reflect at least a part of the second wave emitted by passing through the sample.

In another embodiment, the second speckle generation unit 4410 may further include a separate multiple scattering amplifier 4401 other than the multiple scattering amplification region which is coated on a surface of the second speckle generation unit 4410 and integrated. The multiple scattering amplifier 4401 may be provided on a movement path of the second wave L24 between the wave source 4100 and the second speckle generation unit 4410 and/or between the second speckle generation unit 4410 and the second image sensor 4430 to amplify the number of times of multiple scattering. The multiple scattering amplifier 4401 reflects at least a part of the second wave L24 emitted from the sample to be incident on the sample again, such that the second wave L24 may reciprocate a space between the sample and the multiple scattering amplifier 4401 at least one time, thereby effectively amplifying the number of times of multiple scattering of the second wave L24 in the sample.

In addition, as another embodiment, the multi-scattering amplification region or the multi-scattering amplifier to perform the above function is not provided only in the second speckle generating unit 4410, but also provided in the first speckle generating unit 4310 as well. Of course, the same scattering conditions can be given to the first speckle generation and the second speckle generation.

Meanwhile, the first image sensor 4430 may be disposed on a path from which the second speckle LS24 is emitted to detect the second speckle LS24 in time series order. The second image sensor 4430 may include sensing means corresponding to a type of the wave source 4100, and should detect speckle using the same second wave L24 as the first wave L14, and thus the second image sensor 4430 may be the same type of sensing means as the first image sensor 4330. The second image sensor 4430 may be a CCD camera, and may obtain a plurality of images by capturing the second speckle LS24 in time series order. At this time, a principle for the second image sensor 4430 of obtaining the plurality of images is the same as that of the first image sensor 4330, and thus redundant descriptions thereof will be omitted for convenience of description.

The second image sensor 4430 detects the second speckle LS24 caused by the second wave L24, and the first image sensor 4330 detects the first speckle LS14 caused by the first wave L14. Here, the first wave L14 and the second wave L24 are split from the wave L4 irradiated from the one wave source 4100 and may have the same wave properties when the surrounding environment is the same. Therefore, when a wavelength of the first wave L14 changes, because a wavelength of the second wave L24 also changes, the present disclosure may determine a change in the properties of the first wave L14 and proceed with measurement by utilizing the second wave only in a stable state. In particular, a bacteria detection sensor using the speckle may detect the second speckle LS24 only in a state where the first wave L14 is stable, and thus accurate measurement may be possible.

Figure 29:
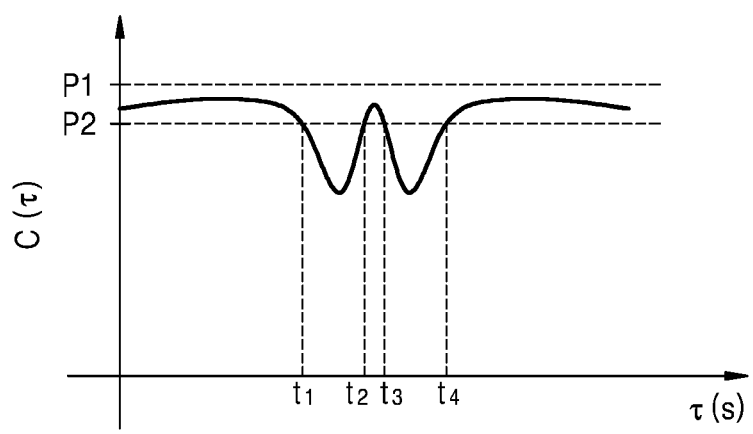
FIG. 29 is a diagram for explaining a method, performed by a controller of the present disclosure, of controlling an operation of a second image sensor due to a first speckle.

FIG. 29 is a diagram for explaining a method, performed by the controller 4500 of the present disclosure, of controlling an operation of the second image sensor 4430 due to the first speckle LS14.

Referring to FIG. 29, the controller 4500 may obtain a temporal correlation of the first speckle LS14 using the detected first speckle LS14, and control the operation of the second image sensor 4430 based on the obtained temporal correlation of the first speckle LS14. More specifically, the controller 4500 may determine a change in the property of the first wave L14 based on the temporal correlation of the first speckle LS14, and control the operation of the second image sensor 4430 according to the change in the property of the first wave L14.

The controller 4500 may obtain the temporal correlation of the first speckle LS14 by using a plurality of images obtained from the first image sensor 4330. At this time, a first image obtained at a first time and a second image obtained at a second time may include at least one of speckle pattern information and intensity information of waves. Meanwhile, an embodiment of the present disclosure does not use only the difference between the first image information at the first time and the second image information at the second time but may extend this to use image information of a plurality of laser speckles at a plurality of times.

The controller 4500 may calculate a temporal correlation coefficient of the first speckle LS14 using the plurality of images generated for a plurality of preset times. When the first wave L14 is stable without a change, because the first speckle LS14 generated by the static scattering medium 311 included in the first speckle generation unit 4310 has a uniform pattern, the temporal correlation coefficient of the first speckle LS14 may have a uniform first value. However, when the first wave L14 is unstable due to a change in the surrounding environment, because the first speckle LS14 also changes, the temporal correlation coefficient changes to a second value different from the first value. The controller 4500 may determine a change in the property of the first wave L14 by using the change in the temporal correlation coefficient.

In an embodiment, the detected temporal correlation of the first wave L14 may be calculated using Equation 5 described above.

The temporal correlation coefficient may be calculated according to Equation 5, and in an embodiment, the temporal correlation coefficient of the first speckle LS14 may be expressed in a graph over time as shown in FIG. 29. As described above, when the first wave L14 is stable, for example, as shown in the graph up to a first time t1, the temporal correlation coefficient maintains a preset range P1 to P2. Unlike this, when the first wave L14 is unstable, for example, as shown in the graph of the first time t1 to a fourth time t4, the temporal correlation coefficient may be beyond the preset range.

The controller 4500 may operate the second image sensor 4430 to detect the second speckle LS24 only when the temporal correlation coefficient corresponds to the preset range. In other words, as shown in FIG. 29, the controller 4500 may control the second image sensor 4430 not to operate during the first time t1 to the fourth time t4 at which the temporal correlation coefficient of the first speckle LS14 is beyond the preset range P1 to P2. Meanwhile, when the first wave L14 is in an unstable state, the temporal correlation coefficient may be included in the preset range such as a second time t2 to a third time t3 of FIG. 29.

Even though the temporal correlation coefficient is temporarily included in the preset range, because the first wave L14 is actually unstable, in this case, the controller 4500 may calculate the temporal correlation coefficient to a ratio at which the temporal correlation coefficient is beyond the preset range within a predetermined time such that the second image sensor 4430 does not operate and determine the change in the property of the first wave L14.

In another embodiment, the controller 4500 may calculate the temporal correlation coefficient of the first speckle LS14 and use the temporal correlation coefficient of the first speckle LS14 to calibrate a detection signal of the second image sensor 4430. For example, the controller 4500 may calculate the temporal correlation coefficient of the first speckle LS14 and calibrate the detection signal through an equation formula such as subtraction or division, etc. of the temporal correlation coefficient from the detection signal provided from the second image sensor 4430. The controller 4500 may detect microbes more accurately by using the calibrated detection signal, that is, the calibrated second speckle LS24.

The controller 4500 may obtain a temporal correlation of the second speckle LS24 detected using the second speckle LS24 detected by the second image sensor 4430, and estimate the presence or concentration of microbe in a sample based on the obtained temporal correlation of the second speckle.

Principle of estimating the presence or the concentration of the microbe based on the temporal correlation of the second speckle LS24 may be also the same as the principle of determining the change in the property of the first wave L14 by using the temporal correlation of the first speckle LS14.

Specifically, a temporal correlation coefficient of the second speckle LS24 may be calculated according to Equation 3, and in an embodiment, the presence or the concentration of microbe may be estimated through an analysis in which the temporal correlation coefficient falls below a preset reference value. Specifically, it may be estimated that microbe is present from that the temporal correlation coefficient falls below the reference value exceeding a preset error range. Also, as the concentration of microbe increases, a time that the temporal correlation coefficients fall below a reference value decreases. Using this, the concentration of microbe may be estimated through inclination values of a graph representing the temporal correlation coefficient. The reference value may be different according to a type of microbe.

Figure 30:
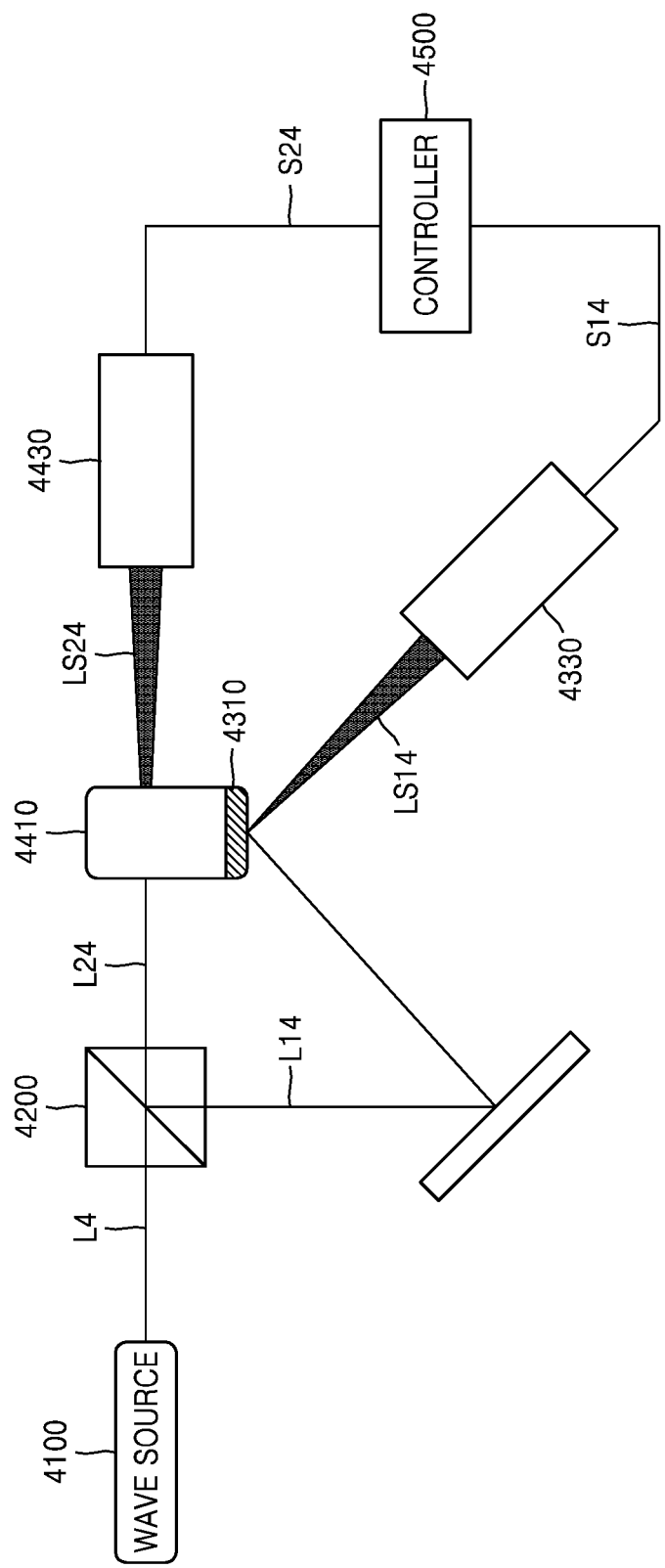
FIG. 30 is a diagram schematically showing an optical detection system of another embodiment.

FIG. 30 is a diagram schematically showing an optical detection system 40-2 of another embodiment.

Referring to FIG. 30, the optical detection system 40-2 may include the wave source 4100, the first optical unit 4200, the first speckle generation unit 4310, the second speckle generation unit 4410, the first image sensor 4330, the second image sensor 4430, and the controller 4500.

In another embodiment, the first speckle generation unit 4310 of the optical detection system 40-2 may be integrally formed with the second speckle generation unit 4410. Specifically, the second speckle generation unit 4410 may be an accommodation container for accommodating a sample to be measured, and the first speckle generation unit 4310 may be provided in one side of the accommodation container. For example, the first speckle generation unit 4310 may be formed in a container of a predetermined shape including a static scattering medium, and may be mounted on one side of the second speckle generation unit 4310. However, the present disclosure is not limited thereto, and in another embodiment, the first speckle generation unit 4410 may be formed by coating the scattering medium fixed to one side of the second speckle generation unit 4310.

In the optical detection system 40-2, because the first speckle generation unit 4310 and the second speckle generation unit 4410 are integrally formed, the first speckle LS14 measured through the first speckle generation unit 4310 may include information about mechanical vibration of the integrally formed second speckle generation unit 4410. Therefore, the optical detection system 40-2 may remove noise due to the mechanical vibration of the second speckle generation unit 4410 through a reference signal by the first speckle LS14.

Figure 31:
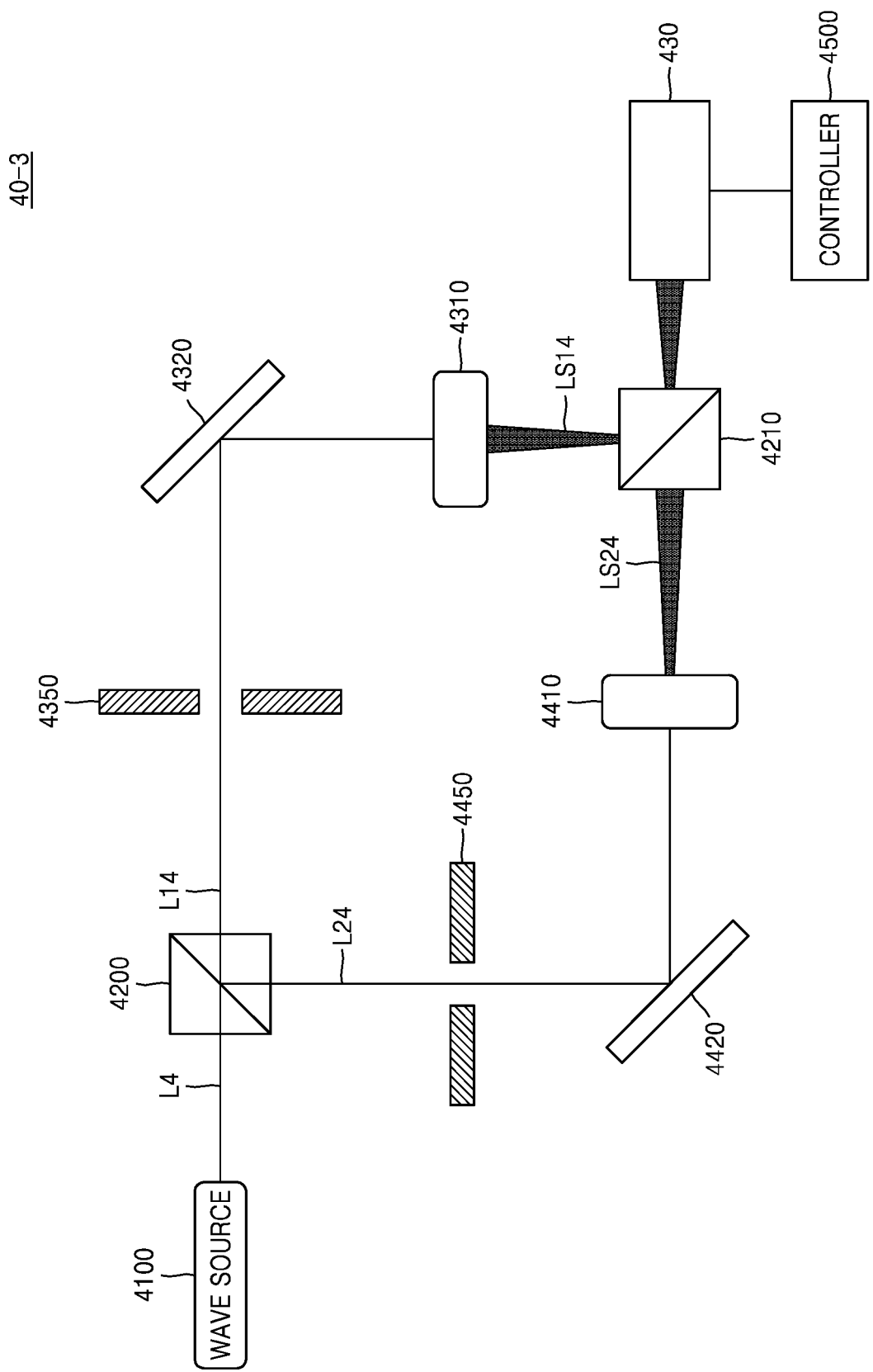
FIG. 31 is a diagram schematically showing an optical detection system according to another embodiment of the present disclosure.

FIG. 31 is a diagram schematically showing an optical detection system 40-3 according to another embodiment of the present disclosure.

Referring to FIG. 31, the optical detection system 40-3 according to another embodiment of the present disclosure may include the wave source 4100, the first optical unit 4200, the first speckle generation unit 4310, the second speckle generation unit 4410, the image sensor 430, and the controller 4500. In addition, the optical detection system 40-3 according to another embodiment of the present disclosure may include a first shutter 4350 and a second shutter 4450. Except that the optical detection system 40-3 according to another embodiment of the present disclosure controls detection of the second speckle LS24 using the second shutter 4450, the remaining components of the optical detection system 40-3 according to another embodiment of the present disclosure are the same as those of the optical detection system 40 according to an embodiment, and thus the same reference numerals are used for convenience of description, and redundant descriptions will be omitted.

The wave source 4100 may generate the wave L4. The wave source 4100 may apply all kinds of source device capable of generating the wave L, and may be, for example, a laser capable of irradiating light of a specific wavelength band.

The first optical unit 4200 may include one or more optical elements to perform a function of splitting the wave L4 generated by the wave source 4100 into the first wave L14 and the second wave L24. In an embodiment, as shown in the drawing, the optical unit 4200 may include a beam splitter that splits the incident wave L4 into the first wave L14 and the second wave L24 to the first path and the second path which are different paths.

A path of the first wave L14 provided from the first optical unit 4200 may be changed to the first speckle generation unit 4310 through a first mirror 4320. In addition, a path of the second wave L24 provided from the first optical unit 4200 may be changed to the second speckle generation unit 4410 through a second mirror 4420. However, the present disclosure is not limited thereto and may use any means capable of changing a light path.

The first speckle generation unit 4310 may be disposed on the path of the first wave L14. The first speckle generation unit 4310 may include a static scattering medium 311 to scatter the first wave L14 when the first wave L14 is incident and generate the first speckle LS14.

The second speckle generation unit 4410 may be disposed on the path of the second wave L24. The second speckle generation unit 4410 may include a sample to be measured to scatter the incident second wave L24 and generate the second speckle LS24.

The image sensor 430 may detect the first speckle LS14 generated from the first speckle generation unit 4310 or the second speckle LS24 generated from the second speckle generation unit 4410 in time series order. The image sensor 430 may be provided in an independently driven component like the optical detection system 40 according to an embodiment, but the first speckle LS14 or the second speckle LS24 may be detected by using one. To this end, the optical detection system 40-2 according to another embodiment, as shown in FIG. 31, may further include a second optical unit 4210 that changes paths of the first speckle LS14 and the second speckle LS24 and provide the first speckle LS14 and the second speckle LS24 to the image sensor 430.

Meanwhile, the second shutter 4450 may be disposed between the first optical unit 4200 and the second speckle generation unit 4410 and may operate under the control of the controller 4500.

The controller 4500 may obtain a temporal correlation of the first speckle LS14 by using the first speckle LS14 detected by the image sensor 430 and control an operation of the second shutter 4450 based on the obtained temporal correlation of the first speckle LS14. Specifically, the controller 4500 may calculate a temporal correlation coefficient of the first speckle LS14 and open the second shutter 4450 such that the second speckle LS24 is detected only when the temporal correlation coefficient corresponds to a preset range. That is, the controller 4500 may detect the second speckle LS24 by opening the second shutter 4450 only when it is determined that the first wave L14 is stable.

In this case, the optical detection system 40-2 may further include the first shutter 4350 disposed between the first optical unit 4200 and the first speckle generation unit 4310. Because the optical detection system 40-2 according to another embodiment detects the first speckle LS14 or the second speckle LS24 using the one image sensor 430, the controller 4500 may close the first shutter 4350 such that the first speckle LS14 is not detected while the image sensor 430 detects the second speckle LS24.

The controller 4500 may calculate the temporal correlation coefficient of the first speckle LS14, use the same to open the second shutter 4450, detect the second speckle LS24 for a predetermined time, and then periodically monitor a change in the first wave L14 by closing the second shutter 4450 again and opening the first shutter 4350.

Figure 32A:
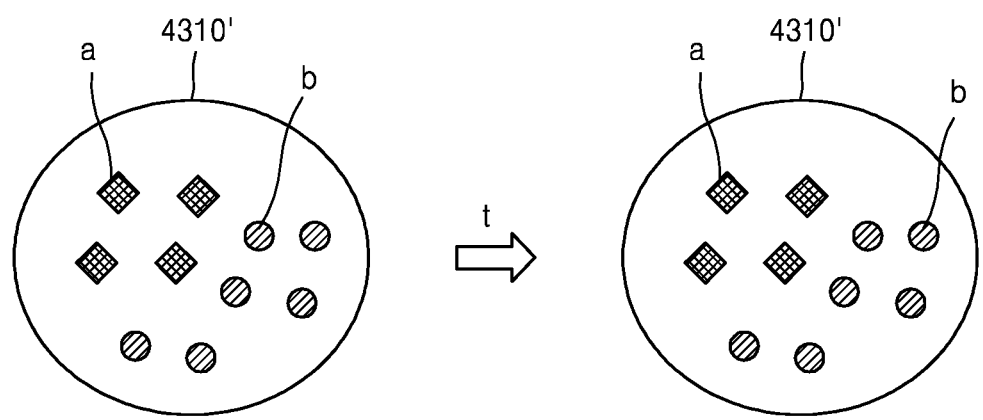
FIGS. 32A and 32B are diagrams for explaining a method of determining the presence of live bacteria in a measurement sample using an optical detection system according to embodiments of the present disclosure.
Figure 32B:
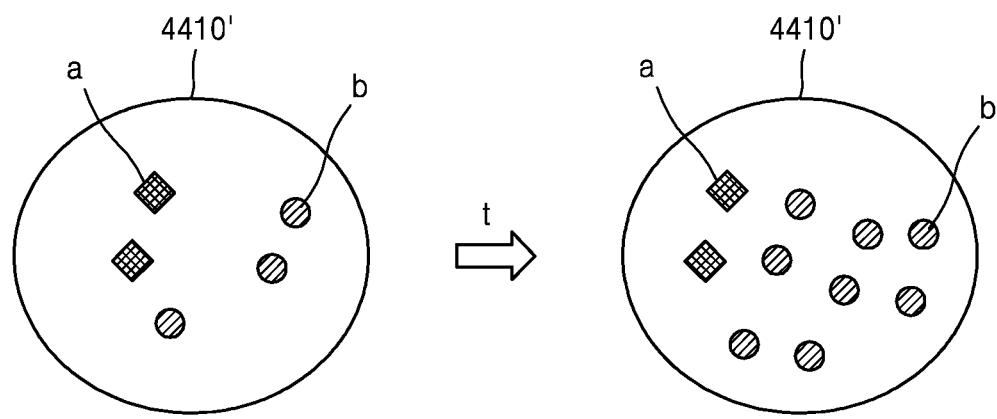

FIGS. 32A and 32B are diagrams for explaining a method of determining the presence of live bacteria in a measurement sample using an optical detection system according to embodiments of the present disclosure.

In the optical detection system according to an embodiment of the present disclosure, a control group sample may be placed in a first speckle generation unit 4310' and a measurement group sample may be placed in a second speckle generation unit 4410' to derive the presence of live bacteria in a sample or a ratio of live and dead bacteria by using detected speckle information.

Specifically, the first speckle generation unit 4310' may include the control group sample. Here, the control group sample may be a sample prepared by injecting a sample to be measured into phosphate buffered saline (PBS). The control group sample may include microbes having a first concentration, and is injected into the PBS, and thus both live and dead bacteria in microbes do not grow over time.

The second speckle generation unit 4410' may include the measurement group sample and a medium. Here, the medium may include a culture material for culturing microbes, and the culture material may include a material corresponding to a type of microbe to be identified and capable of effectively culturing the microbe.

The medium including the culture material used for culturing should suitably meet the requirements of a specific microbe. Various microbe culture media are described, for example, in "Manual of Methods for General Bacteriology" by the American Society for Bacteriology, Washington D.C., USA, 1981.) These media include various carbon sources, nitrogen sources and trace element components. Carbon sources may include carbohydrates such as glucose, lactose, sucrose, fructose, maltose, starch and fiber; fats such as soybean oil, sunflower oil, castor oil and coconut oil; fatty acids such as palmitic acid, stearic acid and linoleic acid; alcohols such as glycerol and ethanol and organic acids such as acetic acid, and these carbon sources may be used alone or in combination, but are not limited thereto. Nitrogen sources may include organic nitrogen sources and urea, such as peptone, yeast extract, gravy, malt extract, corn steep liquor (CSL), and bean flour, and inorganic nitrogen sources such as ammonium sulfate, ammonium chloride, ammonium phosphate, ammonium carbonate, and ammonium nitrate, and these nitrogen sources may be used alone or in combination, but are not limited thereto. The medium may further include potassium dihydrogen phosphate, dipotassium hydrogen phosphate, and corresponding sodium-containing salts as phosphoric acid sources, but is not limited thereto. The medium may also include metals such as magnesium sulfate or iron sulfate, and amino acids, vitamins and suitable precursors may be added.

In an embodiment, the measurement group sample may be the same sample as the control group sample, and may be a sample having the same concentration as the control group sample. At this time, because the measurement group sample is injected to the medium including the culture material, population of live bacteria may increase due to the culture material over time. In other words, as time passes, because the control group sample is injected into the PBS, the population of live and dead bacteria remains constant, whereas the measurement group sample is injected into the medium and the population of live bacteria increases, and thus the concentration of the measurement group sample is higher than the concentration of the control group sample.

The controller 4500 may use the first speckle LS14 and the second speckle LS24 detected from the first speckle generation unit 4310' and the second speckle generation unit 4410' to estimate a first concentration of the control group sample and a second concentration of the measurement group sample, and determine the presence of live bacteria in the measurement group sample using the first concentration and the second concentration. Specifically, the controller 4500 may obtain a temporal correlation of the first speckle LS14 using the detected first speckle LS14, and then estimate the first correlation of the control group sample by using the temporal correlation of the first speckle. In addition, the controller 4500 may obtain a temporal correlation of the second speckle LS24 using the detected second speckle LS24, and then estimate the second correlation of the measurement group sample by using the temporal correlation of the second speckle. The controller 4500 may compare the estimated first concentration and second concentration to determine the presence of live bacteria in the measurement group sample.

On the other hand, in another embodiment, the measurement group sample may be a sample diluted m times the control group sample. In other words, the measurement group sample may have a concentration of 1/m of the control group sample when the measurement group sample is initially injected. As shown in FIG. 32A, the control group sample is included in the PBS, even if a certain time passes, the population of live bacteria b and dead bacteria a of the control group sample does not change. However, as shown in FIG. 32B, in the measurement group sample included in the medium, if a certain time passes, the population of the dead bacteria a of the measurement group sample does not change, but the population of the live bacteria b increases.

The controller 4500 may estimate the first concentration of the control group sample using the continuously detected first speckle LS14, and estimates the second concentration of the measurement group sample using the detected second speckle LS24, and obtain a growth time t at which the second concentration is equal to the first concentration. The controller 4500 may derive the ratio of the live bacteria b and the dead bacteria a in the measurement group sample using the growth time t.

In other words, when the live bacteria b and the dead bacteria a are present in the control group sample at the first concentration as shown in FIG. 32A, the live bacteria b and the dead bacteria a are present at a concentration of 1/m in the measurement group sample obtained by diluting this by m times, and then may be expressed as shown in Equation 7 below after the growth time t.

$$\frac{a - (1 - \alpha t)b}{m} \quad [\text{Equation 7}]$$

Here, α denotes a growth rate of the corresponding microbe and may be a previously known value.

The controller 4500 may obtain the growth time t at which the first concentration of the control group sample and the second concentration of the measurement group sample are equal to each other. Thus, a ratio b/a of the live bacteria b and the dead bacteria a may be derived through a process of Equation 8 below.

$$a - b = \frac{a - (a - \alpha t)b}{m} \quad [\text{Equation 8}]$$
$$\frac{b}{a} = \frac{m - 1}{(1 - \alpha t - m)}$$

As described above, the optical measuring device according to the embodiments of the present disclosure may split a wave generated from a wave source, irradiate a split first wave to a static scattering medium to generate a first speckle that is a reference signal, and then calculate a temporal correlation of the first speckle, thereby accurately determining a change in properties of the first wave. By using this, the optical measuring device may check and calibrate noise caused by the surrounding environment, thereby more accurately detecting microbe in a sample to be measured. In addition, the optical measuring device has the advantage of deriving the presence of live bacteria or a ratio of live bacteria and dead bacteria in a sample by comparing the concentration of a control group sample and a measurement group sample.

The embodiments have been described above. It will be understood by those of ordinary skill in the art that various changes in form and details may be made therein without departing from the spirit and scope of the present disclosure as defined by the appended claims. Therefore, it should be understood that the embodiments are to be considered in an illustrative rather than a restrictive sense. The scope of the present disclosure is set forth in the appended claims rather than the foregoing description and should be interpreted as including all differences within the equivalent range thereto.

INDUSTRIAL APPLICABILITY

According to an embodiment of the present disclosure, an optical detection system using a chaotic wave sensor is provided. In addition, embodiments of the present disclosure may be applied to an industrially used impurity or microbe detection device.

The invention claimed is:

1. An airborne bacteria measuring device comprising:
   a collection unit including
   a storage tank to receive a collected liquid therein,
   a gas-intake flow path placed on one side of the storage tank and configured to suck external air and guide the air to the collected liquid, and
   a gas-exhaust flow path placed another side of the storage tank and configured to discharge the air of the storage tank to an outside;
   a wave source to emit a wave toward the collected liquid of the collection unit;
an image sensor to measure, in time series, a wave speckle generated by multiple scattering of the wave in the collected liquid; and
a control unit to detect the presence of microorganisms in the collected liquid based on a change in the measured wave speckle over time.

2. The airborne bacteria measurement device of claim 1, wherein the control unit acquires a temporal correlation of the wave speckle, and detects the presence of microorganisms in the collected liquid based on the acquired temporal correlation.

3. The airborne bacteria measurement device of claim 1, wherein the collection unit further includes a collected liquid discharge pipe for discharging the collected liquid for which detection is completed, and a collected liquid inlet pipe for introducing a new collected liquid into the storage tank.

4. The airborne bacteria measurement device of claim 3, further comprising:
a first valve installed on the collected liquid inlet pipe and selectively opening and closing the collected liquid inlet pipe; and
a second valve installed on the collected liquid discharge pipe and selectively opening and closing the collected liquid discharge pipe,
wherein the control unit controls the operation of the first valve or the second valve according to a preset program.

5. The airborne bacteria measurement device of claim 4, further comprising a sterilization unit to sterilize, in the storage tank, the collected liquid for which detection is completed, wherein the control unit controls the operation of the second valve to discharge the collected liquid after the collected liquid is completely sterilized.

6. The airborne bacteria measurement device of claim 1, further comprising a filter unit installed in the gas-intake flow path and filtering a substance having a predetermined size or more contained in the external air introduced into the gas-intake flow path.

7. The airborne bacteria measurement device of claim 1, wherein the collection unit further includes a multiple scattering amplification unit for amplifying the number of multiple scatterings in the collected liquid by reflecting at least a part of the wave emitted from the collected liquid to the collected liquid.

8. The airborne bacteria measurement device of claim 1, wherein the control unit distinguishes types or concentrations of the microorganisms present in the collected liquid based on the change in the wave speckle over time.

9. The airborne bacteria measurement device of claim 8, wherein the control unit machine-learns classification criteria for microorganisms based on the change in the wave speckle measured in the order of time series over time, and distinguishes types or concentrations of the microorganisms present in the collected liquid using the classification criteria for microorganisms.

* * * * *